(12) United States Patent
Hood et al.

(10) Patent No.: US 6,632,930 B2
(45) Date of Patent: Oct. 14, 2003

(54) METHOD OF INCREASING RECOVERY OF HETEROLOGOUS ACTIVE ENZYMES PRODUCED IN PLANTS

(75) Inventors: Elizabeth Hood, College Station, TX (US); John A. Howard, College Station, TX (US); Michele Bailey, College Station, TX (US); Franciscus J. C. van Gastel, Union City, CA (US); Michael Ward, San Francisco, CA (US); Huaming Wang, Fremont, CA (US); Susan Woodard, College Station, TX (US)

(73) Assignees: Prodigene, Inc., College Station, TX (US); Genencor International Inc., Palo Alto, CA (US)

( * ) Notice: Subject to any disclaimer, the term of this patent is extended or adjusted under 35 U.S.C. 154(b) by 0 days.

(21) Appl. No.: 09/881,165

(22) Filed: Jun. 14, 2001

(65) Prior Publication Data

US 2002/0039772 A1 Apr. 4, 2002

Related U.S. Application Data

(60) Provisional application No. 60/211,732, filed on Jun. 15, 2000.

(51) Int. Cl.$^7$ .............................. A23J 1/00; C12N 9/02; C12N 9/14; C07H 21/04; A01H 1/00
(52) U.S. Cl. ........................ 530/412; 435/18; 435/25; 435/189; 435/195; 536/23.2; 800/278
(58) Field of Search .................... 530/412; 435/189, 435/18, 25, 195; 536/23.2; 800/278

(56) References Cited

FOREIGN PATENT DOCUMENTS

| WO | WO 90/02719 | 3/1990 |
| WO | WO 99/49020 | 9/1999 |
| WO | WO 00/20615 | 4/2000 |

OTHER PUBLICATIONS

Call, H. P., et al.; "History, overview and applications of mediated lignolytic systems, especially laccase–mediator––systems (Lignozyme–process)", Journal of Biotechnology 53, p. 163–202 (1997).

Hood, E.E., et al.; "The hypervirulence of *Agrobacterium tumefaciens* A281 is encoded in a region of pTiBo542 outside of T–DNA", J Bacteriol. 168:1291–1301 (1986).

Hood, E.E., et al.; "Commercial production of avidin from transgenic maize: Characterization of transformant, production, processing, extraction and purification", Molecular Breeding 3:291–306 (1997).

Hood, E.E., et al.; "Protein products form transgenic plants", Agro–food industry Hi–Tech, 3, vol. 10, May/Jun. 1999, p. 35–36.

Hood, E.E., et al.; "Plant based production of xenogenic Proteins.", Current opinion in Biotechnology, 10:4, p. 382–386 (1999).

Voss, Regis, "Nutrient Deficiencies and toxicities in Crop plants: corn", chapter 2, 11–14. APS Press, Minn. 2:11–14 (1993).

Rains, D.W., "Mineral Metabolism", Chapt. 18 p. 561–597 *Plant Biochemistry*, Third Edit. Bonner and Varner, eds., Academic Press (1976).

Collins, P.J. and Dobson, A.D., "Regulation of Laccase Gene Transcription in *Trametes versicolor*" Appl. AndEnviron. Micro. Sep. 1997, p. 3444–3450.

Palmieri, G. et al., "Copper Induction of Laccase Isoenzymes in the Ligninolytic Fungus *Pleurotus ostreatus*" Appl. And Environ. Micro. Mara. 2000 p. 920–924.

*Primary Examiner*—Tekchand Saidha
(74) *Attorney, Agent, or Firm*—Patricia A. Sweeney

(57) ABSTRACT

A method of increasing recovery of active enzyme produced in a plant is provided where the enzyme requires a transitional metal cofactor for activation. The metal cofactor is supplied to the enzyme during plant development, during extraction, or after extraction. Recovery of active enzyme is also provided by incubating the extracted enzyme at a non-enzyme degrading temperature. Addition of a negative ion salt further improves active enzyme recovery. Optimum salt concentrations for recovery of laccase from plants using copper solutions is provided.

37 Claims, 37 Drawing Sheets

```
      gccatcgggccggtggcgagcctcgtcgtcgcgaacgcccccgtctcgcccgacggcttc
  1   ---------+---------+---------+---------+---------+---------+   60
      cggtagcccggccaccgctcggagcagcagcgcttgcggggcagagcgggctgccgaag
      A  I  G  P  V  A  S  L  V  V  A  N  A  P  V  S  P  D  G  F cttcgggatgccatcgtggtcaacggcgtggtcccttccccgctcatcaccgggaagaag
 61   ---------+---------+---------+---------+---------+---------+  120
      gaagccctacggtagcaccagttgccgcaccagggaaggggcgagtagtggcccttcttc
      L  R  D  A  I  V  V  N  G  V  V  P  S  P  L  I  T  G  K  K ggagaccgcttccagctcaacgtcgtcgacaccttgaccaaccacagcatgctcaagtcc
121   ---------+---------+---------+---------+---------+---------+  180
      cctctggcgaaggtcgagttgcagcagctgtggaactggttggtgtcgtacgagttcagg
      G  D  R  F  Q  L  N  V  V  D  T  L  T  N  H  S  M  L  K  S actagtatccactggcacggcttcttccaggcaggcaccaactgggcagacggacccgcg
181   ---------+---------+---------+---------+---------+---------+  240
      tgatcataggtgaccgtgccgaagaaggtccgtccgtggttgacccgtctgcctgggcgc
      T  S  I  H  W  H  G  F  F  Q  A  G  T  N  W  A  D  G  P  A ttcgtcaaccagtgccctattgcttccgggcattcatttctgtacgacttccatgtgccc
241   ---------+---------+---------+---------+---------+---------+  300
      aagcagttggtcacgggataacgaaggcccgtaagtaaagacatgctgaaggtacacggg
      F  V  N  Q  C  P  I  A  S  G  H  S  F  L  Y  D  F  H  V  P gaccaggcaggaacgttctggtaccacagtcatctgtctacgcaatactgtgacgggctg
301   ---------+---------+---------+---------+---------+---------+  360
      ctggtccgtccttgcaagaccatggtgtcagtagacagatgcgttatgacactgcccgac
      D  Q  A  G  T  F  W  Y  H  S  H  L  S  T  Q  Y  C  D  G  L cgaggaccgttcgtcgtgtacgaccccaaggatccgcacgccagccgctacgatgttgac
361   ---------+---------+---------+---------+---------+---------+  420
      gctcctggcaagcagcacatgctggggttcctaggcgtgcggtcggcgatgctacaactg
      R  G  P  F  V  V  Y  D  P  K  D  P  H  A  S  R  Y  D  V  D aacgagagcacggtcatcacgttgaccgactggtaccacaccgctgcccggctcggtccc
421   ---------+---------+---------+---------+---------+---------+  480
      ttgctctcgtgccagtagtgcaactggctgaccatggtgtggcgacgggccgagccaggg
      N  E  S  T  V  I  T  L  T  D  W  Y  H  T  A  A  R  L  G  P aggttcccactcggcgcggacgccacgctcatcaatggtcttggcggtcggcctccact
481   ---------+---------+---------+---------+---------+---------+  540
      tccaagggtgagccgcgcctgcggtgcgagtagttaccagaacccgccagccggaggtga
      R  F  P  L  G  A  D  A  T  L  I  N  G  L  G  R  S  A  S  T
```

FIG. 1A

```
     cccaccgccgcgcttgctgtgatcaacgtccagcacggaaagcgctaccgcttccgtctc
541  ---------+---------+---------+---------+---------+---------+  600
     gggtggcggcgcgaacgacactagttgcaggtcgtgcctttcgcgatggcgaaggcagag
      P  T  A  A  L  A  V  I  N  V  Q  H  G  K  R  Y  R  F  R  L gtttcgatctcgtgcgacccgaactacacgttcagcatcgacgggcacaatctgaccgtc
601  ---------+---------+---------+---------+---------+---------+  660
     caaagctagagcacgctgggcttgatgtgcaagtcgtagctgcccgtgttagactggcag
      V  S  I  S  C  D  P  N  Y  T  F  S  I  D  G  H  N  L  T  V atcgaggtcgacggtatcaacagccagcctctccttgtcgactctatccagatcttcgcc
661  ---------+---------+---------+---------+---------+---------+  720
     tagctccagctgccatagttgtcggtcggagaggaacagctgagataggtctagaagcgg
      I  E  V  D  G  I  N  S  Q  P  L  L  V  D  S  I  Q  I  F  A gcgcagcgctactcctttgtgttgaatgcgaaccaaacggtcggcaactactgggtccgc
721  ---------+---------+---------+---------+---------+---------+  780
     cgcgtcgcgatgaggaaacacaacttacgcttggtttgccagccgttgatgacccaggcg
      A  Q  R  Y  S  F  V  L  N  A  N  Q  T  V  G  N  Y  W  V  R gcgaacccgaacttcggaacggttgggttcgccggggggatcaactccgccatcctgcgc
781  ---------+---------+---------+---------+---------+---------+  840
     cgcttgggcttgaagccttgccaacccaagcggccccctagttgaggcggtaggacgcg
      A  N  P  N  F  G  T  V  G  F  A  G  G  I  N  S  A  I  L  R taccaaggcgcaccagtcgccgagcccactacgacccagacgacgtcggtgatcccgctt
841  ---------+---------+---------+---------+---------+---------+  900
     atggttccgcgtggtcagcggctcgggtgatgctgggtctgctgcagccactagggcgaa
      Y  Q  G  A  P  V  A  E  P  T  T  T  Q  T  T  S  V  I  P  L atcgagacgaacttgcacccccctcgctcgcatgcctgtgcctggcagcccgacacccggg
901  ---------+---------+---------+---------+---------+---------+  960
     tagctctgcttgaacgtgggggagcgagcgtacggacacggaccgtcgggctgtgggccc
      I  E  T  N  L  H  P  L  A  R  M  P  V  P  G  S  P  T  P  G ggcgtcgacaaggcgctcaacctcgcgtttaacttcaacggcaccaacttcttcatcaac
961  ---------+---------+---------+---------+---------+---------+  1020
     ccgcagctgttccgcgagttggagcgcaaattgaagttgccgtggttgaagaagtagttg
      G  V  D  K  A  L  N  L  A  F  N  F  N  G  T  N  F  F  I  N aacgcgactttcacgccgccgaccgtcccggtactcctccagattctgagcggtgcgcag
1021 ---------+---------+---------+---------+---------+---------+  1080
     ttgcgctgaaagtgcggcggctggcagggccatgaggaggtctaagactcgccacgcgtc
      N  A  T  F  T  P  P  T  V  P  V  L  L  Q  I  L  S  G  A  Q
```

FIG. 1B

```
       accgcacaagacctgctccctgcaggctctgtctacccgctcccggcccactccaccatc
1081   ---------+---------+---------+---------+---------+---------+   1140
       tggcgtgttctggacgagggacgtccgagacagatgggcgagggccgggtgaggtggtag
        T  A  Q  D  L  L  P  A  G  S  V  Y  P  L  P  A  H  S  T  I gagatcacgctgcccgcgaccgccttggccccgggtgcaccgcaccccttccacctgcac
1141   ---------+---------+---------+---------+---------+---------+   1200
       ctctagtgcgacgggcgctggcggaaccggggcccacgtggcgtggggaaggtggacgtg
        E  I  T  L  P  A  T  A  L  A  P  G  A  P  H  P  F  H  L  H ggtcacgccttcgcggtcgttcgcagcgcggggagcaccacgtataactacaacgacccg
1201   ---------+---------+---------+---------+---------+---------+   1260
       ccagtgcggaagcgccagcaagcgtcgcgccctcgtggtgcatattgatgttgctgggc
        G  H  A  F  A  V  V  R  S  A  G  S  T  T  Y  N  Y  N  D  P atcttccgcgacgtcgtgagcacgggcacgcccgccgcgggcgacaacgtcacgatccgc
1261   ---------+---------+---------+---------+---------+---------+   1320
       tagaaggcgctgcagcactcgtgcccgtgcgggcggcgcccgctgttgcagtgctaggcg
        I  F  R  D  V  V  S  T  G  T  P  A  A  G  D  N  V  T  I  R ttccagacggacaaccccgggccgtggttcctccactgccacatcgacttccacctcgac
1321   ---------+---------+---------+---------+---------+---------+   1380
       aaggtctgcctgttggggcccggcaccaaggaggtgacggtgtagctgaaggtggagctg
        F  Q  T  D  N  P  G  P  W  F  L  H  C  H  I  D  F  H  L  D gcgggcttcgcgatcgtgttcgcagaggacgttgcggacgtgaaggcggcgaacccggtt
1381   ---------+---------+---------+---------+---------+---------+   1440
       cgcccgaagcgctagcacaagcgtctcctgcaacgcctgcacttccgccgcttgggccaa
        A  G  F  A  I  V  F  A  E  D  V  A  D  V  K  A  A  N  P  V ccgaaggcgtggtcggacctgtgcccgatctacgacgggctgagcgaggctaaccagtga
1441   -------+---------+---------+---------+---------+---------+    1500
       ggcttccgcaccagcctggacacgggctagatgctgcccgactcgctccgattggtcact
        P  K  A  W  S  D  L  C  P  I  Y  D  G  L  S  E  A  N  Q  *
```

FIG. 1C

1 - 10 ng LACCASE STANDARD
2 - 1 ng LACCASE STANDARD
3 - NEGATIVE CONTROL CORN SEED EXTRACT
4 - LCB CORN SEED EXTRACT
5 - LCC CORN SEED EXTRACT
6 - LCG CORN SEED EXTRACT

1 - EXTRACT WAS PREPARED WITH SAT, NO COOPER TREATMENT
2 - EXTRACT WAS PREPARED WITH SAT + 10 mM CuSO$_4$
3 - EXTRACT WAS PREPARED WITH SAT, THEN TREATED WITH 10 mM CuSO$_4$

1 - EXTRACT WAS PREPARED IN SA, THEN TREATED WITH 10 mM $CuSO_4$ FOR 1 H @ RT
2 - EXTRACT WAS PREPARED IN SA, THEN TREATED WITH 10 mM $CuSO_4$ + 0.5 M NaCl FOR 1 H @ RT
3 - EXTRACT PREPARED IN SA + 0.5 M NaCl, THEN TREATED WITH 10 mM $CuSO_4$ FOR 1 H @ RT

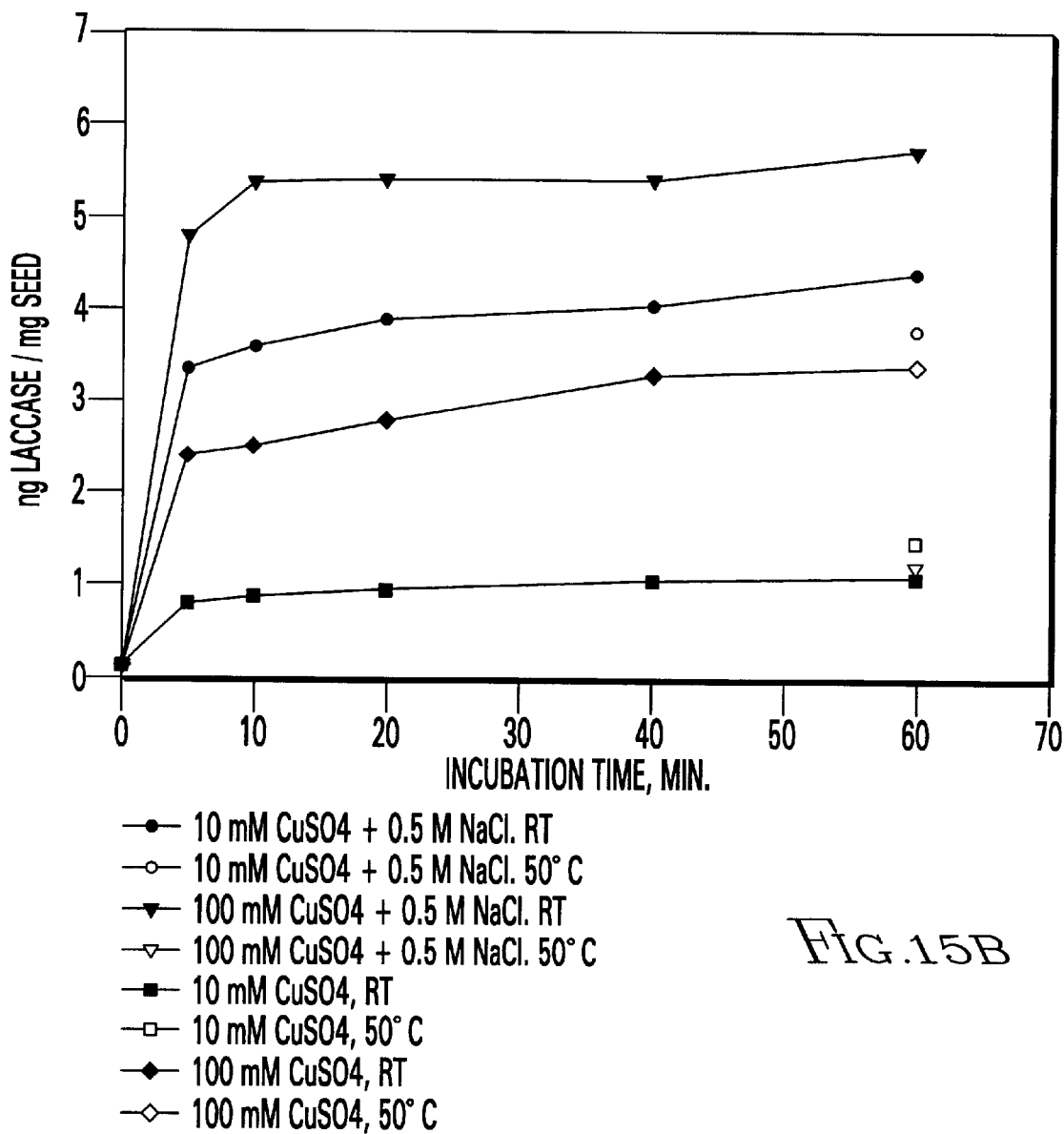

TTCTCCCTTCGGGAAGCGTGGCGCTTTCTCATAGCTCACGCTGTAGGTATCTCAGTTCGGTGTAGGTCGT
TCGCTC
CAAG
CTGGGCTGTGTGCACGAACCCCCCGTTCAGCCCGACCGCTGCGCCTTATCCGGTAACTATCGTCTTGAGT
CCAACC
CGGT
AAGACACGACTTATCGCCACTGGCAGCAGCCACTGGTAACAGGATTAGCAGAGCGAGGTATGTAGGCG
GTGCTACA
GAGT
TCTTGAAGTGGTGGCCTAACTACGGCTACACTAGAAGGACAGTATTTGGTATCTGCGCTCTGCTGAAGC
CAGTTAC
CTTC
GGAAAAAGAGTTGGTAGCTCTTGATCCGGCAAACAAACCACCGCTGGTAGCGGTGGTTTTTTTGTTTGC
AAGCAGC
AGAT
TACGCGCAGAAAAAAGGATCTCAAGAAGATCCTTTGATCTTTTCTACGGGGTCTGACGCTCAGTGGAA
CGAAAAC
TCAC
GTTAAGGGATTTTGGTCATGAGATTATCAAAAAGGATCTTCACCTAGATCCTTTTAAATTAAAAATGAA
GTTTTAA
ATCA
ATCTAAAGTATATATGAGTAAACTTGGTCTGACAGTTACCAATGCTTAATCAGTGAGGCACCTATCTCA
GCGATCT
GTCT
ATTTCGTTCATCCATAGTTGCCTGACTCCCCGTCGTGTAGATAACTACGATACGGGAGCGCTTACCATCT
GGCCCC
AGTG
CTGCAATGATACCGCGAGACCCACGCTCACCGGCTCCAGATTTATCAGCAATAAACCAGCCAGCCGGA
AGGGCCGA
GCGC
AGAAGTGGTCCTGCAACTTTATCCGCCTCCATTCAGTCTATTAATTGTTGCCGGGAAGCTAGAGTAAGT
AGTTCGC
CAGT
TAATAGTTTGCGCAACGTTGTTGGCATTGCTACAGGCATCGTGGTGTCACTCTCGTCGTTTGGTATGGCT
TCATTC
AGCT
CCGGTTCCCAACGATCAAGGCGAGTTACATGATCCCCCATGTTGTGCAAAAAAGCGGTTAGCTCCTTCG
GTCCTCC
GATC
GTTGTCAGAAGTAAGTTGGCCGCAGTGTTATCACTCATGGTTATGGCAGCACTGCATAATTCTCTTACTG
TCATGC
CATC
CGTAAGATGCTTTTCTGTGACTGGTGAGTACTCAACCAAGTCATTCTGAGAATAGTGTATGCGGCGACC
GAGTTGC
TCTT
GCCCGGCGTCAATACGGGATAATAGTGTATCACATAGCAGAACTTTAAAAGTGCTCATCATTGGAAAAC
GTTCTTC
GGGG
CGAAAACTCTCAAGGATCTTACCGCTGTTGAGATCCAGTTCGATGTAACCCACTCGTGCACCCAACTGA
TCTTCAG
CATC
TTTTACTTTCACCAGCGTTTCTGGGTGAGCAAAAACAGGAAGGCAAAATGCCGCAAAAAAGGGAATAA
GGGCGACACGGA

FIG. 16A

AATGTTGAATACTCATACTCTTCCTTTTTCAATGGGTAATAACTGATATAATTAAATTGAAGCTCTAATTTGTGAG
TTTA
GTATACATGCATTTACTTATAATACAGTTTTTTAGTTTTGCTGGCCGCATCTTCTCAAATATGCTTCCCAGCCTGC
TTTT
CTGTAACGTTCACCCTCTACCTTAGCATCCCTTCCCTTTGCAAATAGTCCTCTTCCAACAATAATAATGTCAGATC
CTGT
AGAGACCACATCATCCACGGTTCTATACTGTTGACCCAATGCGTCTCCCTTGTCATCTAAACCCACACCGGGTGTC
ATAA
TCAACCAATCGTAACCTTCATCTCTTCCACCCATGTCTCTTTGAGCAATAAAGCCGATAACAAAATCTTTGTCGCT
CTTC
GCAATGTCAACAGTACCCTTAGTATATTCTCCAGTAGATAGGGAGCCCTTGCATGACAATTCTGCTAACATCAAAA
GGCC
TCTAGGTTCCTTTGTTACTTCTTCTGCCGCCTGCTTCAAACCGCTAACAATACCTGGGCCCACCACACCGTGTGCA
TTCG
TAATGTCTGCCCATTCTGCTATTCTGTATACACCCGCAGAGTACTGCAATTTGACTGTATTACCAATGTCAGCAAA
TTTT
CTGTCTTCGAAGAGTAAAAAATTGTACTTGGCGGATAATGCCTTTAGCGGCTTAACTGTGCCCTCCATGGAAAAAT
CAGT
CAAGATATCCACATGTGTTTTTAGTAAACAAATTTTGGGACCTAATGCTTCAACTAACTCCAGTAATTCCTTGGTG
GTAC
GAACATCCAATGAAGCACACAAGTTTGTTTGCTTTTCGTGCATGATATTAAATAGCTTGGCAGCAACAGGACTAGG
ATGA
GTAGCAGCACGTTCCTTATATGTAGCTTTCGACATGATTTATCTTCGTTTCCTGCAGGTTTTTGTTCTGTGCAGTT
GGGT
TAAGAATACTGGGCAATTTCATGTTTCTTCAACACTACATATGCGTATATATACCAATCTAAGTCTGTGCTCCTTC
CTTC
GTTCTTCCTTCTGTTCGGAGATTACCGAATCAAAAAAATTTCAAAGAAACCGAAATCAAAAAAAAGAATAAAAAAA
AAAT
GATGAATTGAATTGAAAAGCTAGCTTATCGATGATAAGCTGTCAAAGATGAGAATTAATTCCACGGACTATAGACT
ATAC
TAGATACTCCGTCTACTGTACGATACACTTCCGCTCAGGTCCTTGTCCTTTAACGAGGCCTTACCACTCTTTTGTT
ACTC
TATTGATCCAGCTCAGCAAAGGCAGTGTGATCTAAGATTCTATCTTCGCGATGTAGTAAAACTAGCTAGACCGAGA
AAGAGACTAGAAATGCAAAAGGCACTTCTACAATGGCTGCCATCATTATTATCCGATGTGACGCTGC

FIG. 16B

```
AGCTTCTCAATGA
TATT
CGAATACGCTTTGAGGAGATACAGCCTAATATCCGACAAACTGTTTTACAGATTTACGATCGTACTTGT
TACCCAT
CATT
GAATTTTGAACATCCGAACCTGGGAGTTTTCCCTGAAACAGATAGTATATTTGAACCTGTATAATAATA
TATAGTC
TAGC
GCTTTACGGAAGACAATGTATGTATTTCGGTTCCTGGAGAAACTATTGCATCTATTGCATAGGTAATCTT
GCACGT
CGCA
TCCCCGGTTCATTTTCTGCGTTTCCATCTTGCACTTCAATAGCATATCTTTGTTAACGAAGCATCTGTGCT
TCATT
TTGT
AGAACAAAAATGCAACGCGAGAGCGCTAATTTTTCAAACAAAGAATCTGAGCTGCATTTTTACAGAAC
AGAAATGC
AACG
CGAAAGCGCTATTTTACCAACGAAGAATCTGTGCTTCATTTTTGTAAAACAAAAATGCAACGCGACGAG
AGCGCTA
ATTT
TTCAAACAAAGAATCTGAGCTGCATTTTTACAGAACAGAAATGCAACGCGAGAGCGCTATTTTACCAAC
AAAGAAT
CTAT
ACTTCTTTTTTGTTCTACAAAAATGCATCCCGAGAGCGCTATTTTTCTAACAAAGCATCTTAGATTACTT
TTTTTC
TCCT
TTGTGCGCTCTATAATGCAGTCTCTTGATAACTTTTTGCACTGTAGGTCCGTTAAGGTTAGAAGAAGGCT
ACTTTG
GTGT
CTATTTTCTCTTCCATAAAAAAAGCCTGACTCCACTTCCCGCGTTTACTGATTACTAGCGAAGCTGCGGG
TGCATT
TTTT
CAAGATAAAGGCATCCCCGATTATATTCTATACCGATGTGGATTGCGCATACTTTGTGAACAGAAAGTG
ATAGCGT
TGAT
GATTCTTCATTGGTCAGAAAATTATGAACGGTTTCTTCTATTTTGTCTCTATATACTACGTATAGGAAAT
GTTTAC
ATTT
TCGTATTGTTTTCGATTCACTCTATGAATAGTTCTTACTACAATTTTTTGTCTAAAGAGTAATACTAGAG
ATAAA
CATA
AAAAATGTAGAGGTCGAGTTTAGATGCAAGTTCAAGGAGCGAAAGGTGGATGGGTAGGTTATATAGGG
ATATAGCA
CAGA
GATATATAGCAAAGAGATACTTTTGAGCAATGTTTGTGGAAGCGGTATTCGCAATGGGAAGCTCCACCC
CGGTTGA
TAAT
CAGAAAAGCCCCAAAAACAGGAAGATTGTATAAGCAAATATTTAAATTGTAAACGTTAATATTTTGTTA
AAATTCG
CGTT
AAATTTTTGTTAAATCAGCTCATTTTTTAACGAATAGCCCGAAATCGGCAAAATCCCTTATAAATCAAA
AGAATAG
ACCG
AGATAGGGTTGAGTGTTGTTCCAGTTTCCAACAAGAGTCCACTATTAAAGAACGTGGACTCCAACGTCA
AAGGGCG
```

FIG. 16C

AAAA
AGGGTCTATCAGGGCGATGGCCCACTACGTGAACCATCACCCTAATCAAGTTTTTTGGGGTCGAGGTGC
CGTAAAG
CAGT
AAATCGGAAGGGTAAACGGATGCCCCCATTTAGAGCTTGACGGGGAAAGCCGGCGAACGTGGCGAGA
AAGGAAGGG
AAGA
AAGCGAAAGGAGCGGGGGCTAGGGCGGTGGGAAGTGTAGGGGTCACGCTGGGCGTAACCACCACACC
CGCCGCGCT
TAAT
GGGGCGCTACAGGGCGCGTGGGGATGATCCACTAGTACGGATTAGAAGCCGCCGAGCGGGTGACAGCC
CTCCGAAG
GAAG
ACTCTCCTCCGTGCGTCCTCGTCCTCACCGGTCGCGTTCCTGAAACGCAGATGTGCCTCGCGCCGCACTG
CTCCGA
ACAA
TAAAGATTCTACAATACTAGCTTTTATGGTTATGAAGAGGAAAAATTGGCAGTAACCTGGCCCCACAAA
CCTTCAA
ATGA
ACGAATCAAATTAACAACCATAGGATGATAATGCGATTAGTTTTTTAGCCTTATTTCTGGGGTAATTAAT
CAGCGA
AGCG
ATGATTTTTGATCTATTAACAGATATATAAATGCAAAAACTGCATTAACCACTTTAACTAATACTTTCAA
CATTTT
CGGT
TTGTATTACTTCTTATTCAAATGTAATAAAAGTATCAACAAAAAATTGTTAATATACCTCTATACTTTAA
CGTCAA
GGAG
AAAAAACCCCGGATCGGACTACTAGCAGCTGTAATACGACTCACTATAGGGAATATTAAGCTTGGTACC
GAGCTCG
GATC
TTCGAATGCATCGCGCGCACCGTACGTCTCGAGCGGCCGCCAGTGTGATGGATATCTGCAGAATTCGGC
TTGTCAA
TATG
CTGTTCAAGTCATGGCAACTGGCAGCAGCCTCCGGGCTCCTGTCTGGAGTCCTCGGCATCCCGATGGAC
ACCGGCA
GCCA
CCCCATTGAGGCTGTTGATCCCGAAGTGAAGACTGAGGTCTTCGCTGACTCCCTCCTTGCTGCAGCAGG
CGATGAC
GACT
GGGAGTCACCTCCATACAACTTGCTTTACAGGAATGCCCTGCCAATTCCACCTGTCAAGCAGCCCAAGA
TGATCAT
TACC
AACCCTGTCACCGGCAAGGACATTTGGTACTATGAGATCGAGATCAAGCCATTTCAGCAAAGGATTTAC
CCCACCT
TGCG
CCCTGCCACTCTCGTCGGCTACGATGGCATGAGCCCTGGTCCTACTTTCAATGTTCCCAGAGGAACAGA
GACTGTA
GTTA
GGTTCATCAACAATGCCACCGTGGAGAACTCGGTCCATCTGCACGGCTCCCCATCGCGTGCCCCTTTCG
ATGGTTG
GGCT
GAAGATGTGACCTTCCCTGGCGAGTACAAGGATTACTACTTTCCCAACTACCAATCCGCCCGCCTTCTGT
GGTACC
ATGA

FIG. 16D

CCACGCTTTCATGAAGACTGCTGAGAATGCCTACTTTGGTCAGGCTGGCGCCTACATTATCAACGACGAGGCTGAGGATG
CTCTCGGTCTTCCTAGTGGCTATGGCGAGTTCGATATCCCTCTGATCCTGACGGCCAAGTACTATAACGCCGATGGTACC
CTGCGTTCGACCGAGGGTGAGGACCAGGACCTGTGGGGAGATGTCATCCATGTCAACGGACAGCCATGGCCTTTCCTTAA
CGTCCAGCCCCGCAAGTACCGTTTCCGATTCCTCAACGCTGCCGTGTCTCGTGCTTGGCTCCTCTACCTCGTCAGGACCA
GCTCTCCCAACGTCAGAATTCCTTTCCAAGTCATTGCCTCTGATGCTGGTCTCCTTCAAGCCCCGTTCAGACCTCTAAC
CTCTACCTTGCTGTTGCCGAGCGTTACGAGATCATTATTGACTTCACCAACTTTGCTGGCCAGACTCTTGACCTGCGCAA
CGTTGCTGAGACCAACGATGTCGGCGACGAGGATGAGTACGCTCGCACTCTCGAGGTGATGCGCTTCGTCGTCAGCTCTG
GCACTGTTGAGGACAACAGCCAGGTCCCCTCCACTCTCCGTGACGTTCCTTTCCCTCCTCACAAGGAAGCCCCGCCGAC
AAGCACTTCAAGTTTGAACGCAGCAACGGACACTACCTGATCAACGATGTTGGCTTTGCCGATGTCAATGAGCGTGTCCT
GGCCAAGCCCGAGCTCGGCACCGTTGAGGTCTGGGAGCTCGAGAACTCCTCTGGAGGCTGGAGCCACCCCGTCCACATTC
ACCTTGTTGACTTCAAGATCCTCAAGCGAACTGGTGGTCGTGGCCAGGTCATGCCCTACGAGTCTGCTGGTCTTAAGGAT
GTCGTCTGGTTGGGCAGGGGTGAGACCCTGACCATCGAGGCCCACTACCAACCCTGGACTGGAGCTTACATGTGGCACTG
TCACAACCTCATTCACGAGGATAACGACATGATGGCTGTATTCAACGTCACCGCCATGGAGGAGAAGGGATATCTTCAGG
AGGACTTCGAGGACCCCATGAACCCCAAGTGGCGCGCCGTTCCTTACAACCGCAACGACTTCCATGCTCGCGCTGGAAAC
TTCTCCGCCGAGTCCATCACTGCCCGAGTGCAGGAGCTGGCCGAGCAGGAGCCGTACAACCGCCTCGATGAGATCCTGGA
GGATCTTGGAATCGAGGAGTAGTCTAGAGGGCCGCATCATGTAATTAGTTATGTCACGCTTACATTCACGCCCTCCCCCC
ACATCCGCTCTAACCGAAAAGGAAGGAGTTAGACAACCTGAAGTCTAGGTCCCTATTTATTTTTTTATAGTTATGTTAGT
ATTAAGAACGTTATTTATATTTCAAATTTTTCTTTTTTTTCTGTACAGACGCGTGTACGCATGTAACATTATACTGAAAA
CCTTGCTTGAGAAGGTTTTGGGACGCTCGAAGGCTTTAATTTGCGGCC

FIG. 16E

CCATGGCCAACAAGCACCTGAGCCTCTCCTCTCGTGCTCCTCCGGCCTCCTCCGCCAGGCGGCACCGGCGACC
GCATCAACACCGTGCGGCCCGATCAACCATCTCCGAGGCCGGCTTCACCCTCACCGAGCACACATCTGCGGCTCCTCCGCC
GGCTTCCTCCGCGCCGCCTGGCCGGAGTTCTTCGGCTCCCGCAAGGCCCTCCCGCAGAAGGCCGTGCGGCCTCCGCGCCC
GCGCCGGCCGGCCGTGCGCACCATCGTGGCACCTTCGACATCGGCGCGACGTGTCCCTCCTCGCCGAGGTGTCCG
CGCCGGCCGACGTGCACATCGTGGCCGCCACCGGCCTCTGGTTCGACCCGCCGCTCTCCATGCGCCTCCGCTCCGTGGAGGAG
CTCACCCCAGTTCTTCCTCCGCGGAGATCCAGTACGGCATCGAGGACAACCGGGCCATCGCGCGCACCGGCGTCCGTGGAGGAG
CGGCAAGGCCACCCCGTTCCAGGAGCTCGTGCTCAAGGAGCTCGTGCTGAGCAGCAGGCCGCCATCTTGAGTCCGAGGGCTGCCACCAC
CCACACCGCCCTCCGACGACGACCACCGACCTCTCCTACCTCACCGCCCGCCATCTTGAGTCCGAGGGCTCTCCCCGGCGTGCCGGGTGACCAC
CATCGGCCACTCCGCCCATCGGCCTCGAGGACAACGCCTCCCTCGGCTACCTCCGCCATCCGCTCCTGGCAGACCCGCCCTC
TCCGCACTCAAGGCCCTCATGACGTGATGAACCGGGCTACATGAAGCAGATCCTGTCCAACGACTGGCTCTTCTGGCTCTTCCGTTCCGGGAGA
CAACATCATGGACGTGATGAACCGGGCTACATGAAGCAGATCCTGTCCAACGACTGGCCTTCATCCCGTTCCGGAGA
AGGGCCGTGCCAGGAGAGACCCTCGCCGGCATCACCGTGACCAACCCGTGACCAACCCGGCATCACCGTGACCAACCCGGCTTCCTCTCCCGACCCTCTCCCGGCCTCCTG
AGTTAAC

SEQUENCE LISTING

<160> NUMBER OF SEQ ID NOS: 5

<210> SEQ ID NO 1
<211> LENGTH: 1500
<212> TYPE: DNA
<213> ORGANISM: Trametes sp.
<220> FEATURE:
<221> NAME/KEY: CDS
<222> LOCATION: (1)..(1497)

<400> SEQUENCE: 1

| | | | | | | | | | | | | | | | | |
|---|---|---|---|---|---|---|---|---|---|---|---|---|---|---|---|---|
| gcc | atc | ggg | ccg | gtg | gcg | agc | ctc | gtc | gtc | gcg | aac | gcc | ccc | gtc | tcg | 48 |
| Ala | Ile | Gly | Pro | Val | Ala | Ser | Leu | Val | Val | Ala | Asn | Ala | Pro | Val | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ccc | gac | ggc | ttc | ctt | cgg | gat | gcc | atc | gtg | gtc | aac | ggc | gtg | gtc | cct | 96 |
| Pro | Asp | Gly | Phe | Leu | Arg | Asp | Ala | Ile | Val | Val | Asn | Gly | Val | Val | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| tcc | ccg | ctc | atc | acc | ggg | aag | aag | gga | gac | cgc | ttc | cag | ctc | aac | gtc | 144 |
| Ser | Pro | Leu | Ile | Thr | Gly | Lys | Lys | Gly | Asp | Arg | Phe | Gln | Leu | Asn | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| gtc | gac | acc | ttg | acc | aac | cac | agc | atg | ctc | aag | tcc | act | agt | atc | cac | 192 |
| Val | Asp | Thr | Leu | Thr | Asn | His | Ser | Met | Leu | Lys | Ser | Thr | Ser | Ile | His | |
| 50 | | | | | 55 | | | | | 60 | | | | | | |

| | | | | | | | | | | | | | | | | |
|---|---|---|---|---|---|---|---|---|---|---|---|---|---|---|---|---|
| tgg | cac | ggc | ttc | ttc | cag | gca | ggc | acc | aac | tgg | gca | gac | gga | ccc | gcg | 240 |
| Trp | His | Gly | Phe | Phe | Gln | Ala | Gly | Thr | Asn | Trp | Ala | Asp | Gly | Pro | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttc | gtc | aac | cag | tgc | cct | att | gct | tcc | ggg | cat | tca | ttt | ctg | tac | gac | 288 |
| Phe | Val | Asn | Gln | Cys | Pro | Ile | Ala | Ser | Gly | His | Ser | Phe | Leu | Tyr | Asp | |
| | | | | 85 | | | | | 90 | | | | | 95 | | |

| | | | | | | | | | | | | | | | | |
|---|---|---|---|---|---|---|---|---|---|---|---|---|---|---|---|---|
| ttc | cat | gtg | ccc | gac | cag | gca | gga | acg | ttc | tgg | tac | cac | agt | cat | ctg | 336 |
| Phe | His | Val | Pro | Asp | Gln | Ala | Gly | Thr | Phe | Trp | Tyr | His | Ser | His | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| tct | acg | caa | tac | tgt | gac | ggg | ctg | cga | gga | ccg | ttc | gtc | gtg | tac | gac | 384 |
| Ser | Thr | Gln | Tyr | Cys | Asp | Gly | Leu | Arg | Gly | Pro | Phe | Val | Val | Tyr | Asp | |
| | | 115 | | | | | 120 | | | | | 125 | | | | |

| | | | | | | | | | | | | | | | | |
|---|---|---|---|---|---|---|---|---|---|---|---|---|---|---|---|---|
| ccc | aag | gat | ccg | cac | gcc | agc | cgc | tac | gat | gtt | gac | aac | gag | agc | acg | 432 |
| Pro | Lys | Asp | Pro | His | Ala | Ser | Arg | Tyr | Asp | Val | Asp | Asn | Glu | Ser | Thr | |
| | 130 | | | | | 135 | | | | | 140 | | | | | |

| | | | | | | | | | | | | | | | | |
|---|---|---|---|---|---|---|---|---|---|---|---|---|---|---|---|---|
| gtc | atc | acg | ttg | acc | gac | tgg | tac | cac | acc | gct | gcc | cgg | ctc | ggt | ccc | 480 |
| Val | Ile | Thr | Leu | Thr | Asp | Trp | Tyr | His | Thr | Ala | Ala | Arg | Leu | Gly | Pro | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| agg | ttc | cca | ctc | ggc | gcg | gac | gcc | acg | ctc | atc | aat | ggt | ctt | ggg | cgg | 528 |
| Arg | Phe | Pro | Leu | Gly | Ala | Asp | Ala | Thr | Leu | Ile | Asn | Gly | Leu | Gly | Arg | |
| | | | | 165 | | | | | 170 | | | | | 175 | | |

| | | | | | | | | | | | | | | | | |
|---|---|---|---|---|---|---|---|---|---|---|---|---|---|---|---|---|
| tcg | gcc | tcc | act | ccc | acc | gcc | gcg | ctt | gct | gtg | atc | aac | gtc | cag | cac | 576 |
| Ser | Ala | Ser | Thr | Pro | Thr | Ala | Ala | Leu | Ala | Val | Ile | Asn | Val | Gln | His | |
| | | | | 180 | | | | | 185 | | | | | 190 | | |

| | | | | | | | | | | | | | | | | |
|---|---|---|---|---|---|---|---|---|---|---|---|---|---|---|---|---|
| gga | aag | cgc | tac | cgc | ttc | cgt | ctc | gtt | tcg | atc | tcg | tgc | gac | ccg | aac | 624 |
| Gly | Lys | Arg | Tyr | Arg | Phe | Arg | Leu | Val | Ser | Ile | Ser | Cys | Asp | Pro | Asn | |
| | | 195 | | | | | 200 | | | | | 205 | | | | |

| | | | | | | | | | | | | | | | | |
|---|---|---|---|---|---|---|---|---|---|---|---|---|---|---|---|---|
| tac | acg | ttc | agc | atc | gac | ggg | cac | aat | ctg | acc | gtc | atc | gag | gtc | gac | 672 |
| Tyr | Thr | Phe | Ser | Ile | Asp | Gly | His | Asn | Leu | Thr | Val | Ile | Glu | Val | Asp | |
| | 210 | | | | | 215 | | | | | 220 | | | | | |

| | | | | | | | | | | | | | | | | |
|---|---|---|---|---|---|---|---|---|---|---|---|---|---|---|---|---|
| ggt | atc | aac | agc | cag | cct | ctc | ctt | gtc | gac | tct | atc | cag | atc | ttc | gcc | 720 |
| Gly | Ile | Asn | Ser | Gln | Pro | Leu | Leu | Val | Asp | Ser | Ile | Gln | Ile | Phe | Ala | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gcg | cag | cgc | tac | tcc | ttt | gtg | ttg | aat | gcg | aac | caa | acg | gtc | ggc | aac | 768 |
| Ala | Gln | Arg | Tyr | Ser | Phe | Val | Leu | Asn | Ala | Asn | Gln | Thr | Val | Gly | Asn | |
| | | | | 245 | | | | | 250 | | | | | 255 | | |

```
tac tgg gtc cgc gcg aac ccg aac ttc gga acg gtt ggg ttc gcc ggg      816
Tyr Trp Val Arg Ala Asn Pro Asn Phe Gly Thr Val Gly Phe Ala Gly
        260                 265                 270 ggg atc aac tcc gcc atc ctg cgc tac caa ggc gca cca gtc gcc gag      864
Gly Ile Asn Ser Ala Ile Leu Arg Tyr Gln Gly Ala Pro Val Ala Glu
            275                 280                 285 ccc act acg acc cag acg acg tcg gtg atc ccg ctt atc gag acg aac      912
Pro Thr Thr Thr Gln Thr Thr Ser Val Ile Pro Leu Ile Glu Thr Asn
        290                 295                 300 ttg cac ccc ctc gct cgc atg cct gtg cct ggc agc ccg aca ccc ggg      960
Leu His Pro Leu Ala Arg Met Pro Val Pro Gly Ser Pro Thr Pro Gly
305                 310                 315                 320 ggc gtc gac aag gcg ctc aac ctc gcg ttt aac ttc aac ggc acc aac     1008
Gly Val Asp Lys Ala Leu Asn Leu Ala Phe Asn Phe Asn Gly Thr Asn
                325                 330                 335 ttc ttc atc aac aac gcg act ttc acg ccg ccg acc gtc ccg gta ctc     1056
Phe Phe Ile Asn Asn Ala Thr Phe Thr Pro Pro Thr Val Pro Val Leu
            340                 345                 350 ctc cag att ctg agc ggt gcg cag acc gca caa gac ctg ctc cct gca     1104
Leu Gln Ile Leu Ser Gly Ala Gln Thr Ala Gln Asp Leu Leu Pro Ala
        355                 360                 365 ggc tct gtc tac ccg ctc ccg gcc cac tcc acc atc gag atc acg ctg     1152
Gly Ser Val Tyr Pro Leu Pro Ala His Ser Thr Ile Glu Ile Thr Leu
    370                 375                 380 ccc gcg acc gcc ttg gcc ccg ggt gca ccg cac ccc ttc cac ctg cac     1200
Pro Ala Thr Ala Leu Ala Pro Gly Ala Pro His Pro Phe His Leu His
385                 390                 395                 400 ggt cac gcc ttc gcg gtc gtt cgc agc gcg ggg agc acc acg tat aac     1248
Gly His Ala Phe Ala Val Val Arg Ser Ala Gly Ser Thr Thr Tyr Asn
                405                 410                 415 tac aac gac ccg atc ttc cgc gac gtc gtg agc acg ggc acg ccc gcc     1296
Tyr Asn Asp Pro Ile Phe Arg Asp Val Val Ser Thr Gly Thr Pro Ala
            420                 425                 430 gcg ggc gac aac gtc acg atc cgc ttc cag acg gac aac ccc ggg ccg     1344
Ala Gly Asp Asn Val Thr Ile Arg Phe Gln Thr Asp Asn Pro Gly Pro
        435                 440                 445 tgg ttc ctc cac tgc cac atc gac ttc cac ctc gac gcg ggc ttc gcg     1392
Trp Phe Leu His Cys His Ile Asp Phe His Leu Asp Ala Gly Phe Ala
    450                 455                 460 atc gtg ttc gca gag gac gtt gcg gac gtg aag gcg gcg aac ccg gtt     1440
Ile Val Phe Ala Glu Asp Val Ala Asp Val Lys Ala Ala Asn Pro Val
465                 470                 475                 480 ccg aag gcg tgg tcg gac ctg tgc ccg atc tac gac ggg ctg agc gag     1488
Pro Lys Ala Trp Ser Asp Leu Cys Pro Ile Tyr Asp Gly Leu Ser Glu
                485                 490                 495 gct aac cag tga                                                      1500
Ala Asn Gln <210> SEQ ID NO 2
<211> LENGTH: 499
<212> TYPE: PRT
<213> ORGANISM: Trametes sp.

<400> SEQUENCE: 2

Ala Ile Gly Pro Val Ala Ser Leu Val Val Ala Asn Ala Pro Val Ser
  1               5                  10                  15

Pro Asp Gly Phe Leu Arg Asp Ala Ile Val Val Asn Gly Val Val Pro
                 20                  25                  30

Ser Pro Leu Ile Thr Gly Lys Lys Gly Asp Arg Phe Gln Leu Asn Val
             35                  40                  45
```

```
Val Asp Thr Leu Thr Asn His Ser Met Leu Lys Ser Thr Ser Ile His
     50                  55                  60

Trp His Gly Phe Phe Gln Ala Gly Thr Asn Trp Ala Asp Gly Pro Ala
 65                  70                  75                  80

Phe Val Asn Gln Cys Pro Ile Ala Ser Gly His Ser Phe Leu Tyr Asp
                 85                  90                  95

Phe His Val Pro Asp Gln Ala Gly Thr Phe Trp Tyr His Ser His Leu
                100                 105                 110

Ser Thr Gln Tyr Cys Asp Gly Leu Arg Gly Pro Phe Val Val Tyr Asp
            115                 120                 125

Pro Lys Asp Pro His Ala Ser Arg Tyr Asp Val Asp Asn Glu Ser Thr
            130                 135                 140

Val Ile Thr Leu Thr Asp Trp Tyr His Thr Ala Ala Arg Leu Gly Pro
145                 150                 155                 160

Arg Phe Pro Leu Gly Ala Asp Ala Thr Leu Ile Asn Gly Leu Gly Arg
                165                 170                 175

Ser Ala Ser Thr Pro Thr Ala Ala Leu Ala Val Ile Asn Val Gln His
            180                 185                 190

Gly Lys Arg Tyr Arg Phe Arg Leu Val Ser Ile Ser Cys Asp Pro Asn
            195                 200                 205

Tyr Thr Phe Ser Ile Asp Gly His Asn Leu Thr Val Ile Glu Val Asp
        210                 215                 220

Gly Ile Asn Ser Gln Pro Leu Leu Val Asp Ser Ile Gln Ile Phe Ala
225                 230                 235                 240

Ala Gln Arg Tyr Ser Phe Val Leu Asn Ala Asn Gln Thr Val Gly Asn
                245                 250                 255

Tyr Trp Val Arg Ala Asn Pro Asn Phe Gly Thr Val Gly Phe Ala Gly
                260                 265                 270

Gly Ile Asn Ser Ala Ile Leu Arg Tyr Gln Gly Ala Pro Val Ala Glu
        275                 280                 285

Pro Thr Thr Thr Gln Thr Thr Ser Val Ile Pro Leu Ile Glu Thr Asn
        290                 295                 300

Leu His Pro Leu Ala Arg Met Pro Val Pro Gly Ser Pro Thr Pro Gly
305                 310                 315                 320

Gly Val Asp Lys Ala Leu Asn Leu Ala Phe Asn Phe Asn Gly Thr Asn
                325                 330                 335

Phe Phe Ile Asn Asn Ala Thr Phe Thr Pro Pro Thr Val Pro Val Leu
                340                 345                 350

Leu Gln Ile Leu Ser Gly Ala Gln Thr Ala Gln Asp Leu Leu Pro Ala
            355                 360                 365

Gly Ser Val Tyr Pro Leu Pro Ala His Ser Thr Ile Glu Ile Thr Leu
        370                 375                 380

Pro Ala Thr Ala Leu Ala Pro Gly Ala Pro His Pro Phe His Leu His
385                 390                 395                 400

Gly His Ala Phe Ala Val Val Arg Ser Ala Gly Ser Thr Thr Tyr Asn
                405                 410                 415

Tyr Asn Asp Pro Ile Phe Arg Asp Val Val Ser Thr Gly Thr Pro Ala
            420                 425                 430

Ala Gly Asp Asn Val Thr Ile Arg Phe Gln Thr Asp Asn Pro Gly Pro
            435                 440                 445

Trp Phe Leu His Cys His Ile Asp Phe His Leu Asp Ala Gly Phe Ala
        450                 455                 460
```

```
Ile Val Phe Ala Glu Asp Val Ala Asp Val Lys Ala Ala Asn Pro Val
465                 470                 475                 480

Pro Lys Ala Trp Ser Asp Leu Cys Pro Ile Tyr Asp Gly Leu Ser Glu
                485                 490                 495

Ala Asn Gln

<210> SEQ ID NO 3
<211> LENGTH: 7259
<212> TYPE: DNA
<213> ORGANISM: Stachybotrys sp.

<400> SEQUENCE: 3
```

| | | | | | |
|---|---|---|---|---|---|
| ttctcccttc | gggaagcgtg | gcgctttctc | atagctcacg | ctgtaggtat | ctcagttcgg | 60 |
| tgtaggtcgt | tcgctccaag | ctgggctgtg | tgcacgaacc | ccccgttcag | cccgaccgct | 120 |
| gcgccttatc | cggtaactat | cgtcttgagt | ccaacccggt | aagacacgac | ttatcgccac | 180 |
| tggcagcagc | cactggtaac | aggattagca | gagcgaggta | tgtaggcggt | gctacagagt | 240 |
| tcttgaagtg | gtggcctaac | tacggctaca | ctagaaggac | agtatttggt | atctgcgctc | 300 |
| tgctgaagcc | agttaccttc | ggaaaaagag | ttggtagctc | ttgatccggc | aaacaaacca | 360 |
| ccgctggtag | cggtggtttt | tttgtttgca | agcagcagat | tacgcgcaga | aaaaaggat | 420 |
| ctcaagaaga | tcctttgatc | ttttctacgg | ggtctgacgc | tcagtggaac | gaaaactcac | 480 |
| gttaagggat | tttggtcatg | agattatcaa | aaaggatctt | cacctagatc | cttttaaatt | 540 |
| aaaaatgaag | ttttaaatca | atctaaagta | tatatgagta | aacttggtct | gacagttacc | 600 |
| aatgcttaat | cagtgaggca | cctatctcag | cgatctgtct | atttcgttca | tccatagttg | 660 |
| cctgactccc | cgtcgtgtag | ataactacga | tacgggagcg | cttaccatct | ggccccagtg | 720 |
| ctgcaatgat | accgcgagac | ccacgctcac | cggctccaga | tttatcagca | ataaaccagc | 780 |
| cagccggaag | ggccgagcgc | agaagtggtc | ctgcaacttt | atccgcctcc | attcagtcta | 840 |
| ttaattgttg | ccgggaagct | agagtaagta | gttcgccagt | taatagtttg | cgcaacgttg | 900 |
| ttggcattgc | tacaggcatc | gtggtgtcac | tctcgtcgtt | tggtatggct | tcattcagct | 960 |
| ccggttccca | acgatcaagg | cgagttacat | gatcccccat | gttgtgcaaa | aaagcggtta | 1020 |
| gctccttcgg | tcctccgatc | gttgtcagaa | gtaagttggc | cgcagtgtta | tcactcatgg | 1080 |
| ttatggcagc | actgcataat | tctcttactg | tcatgccatc | cgtaagatgc | ttttctgtga | 1140 |
| ctggtgagta | ctcaaccaag | tcattctgag | aatagtgtat | gcggcgaccg | agttgctctt | 1200 |
| gcccggcgtc | aatacgggat | aatagtgtat | cacatagcag | aactttaaaa | gtgctcatca | 1260 |
| ttggaaaacg | ttcttcgggg | cgaaaactct | caaggatctt | accgctgttg | agatccagtt | 1320 |
| cgatgtaacc | cactcgtgca | cccaactgat | cttcagcatc | ttttactttc | accagcgttt | 1380 |
| ctgggtgagc | aaaaacagga | aggcaaaatg | ccgcaaaaaa | gggaataagg | gcgacacgga | 1440 |
| grbaatgttg | aatactcata | ctcttccttt | ttcaatgggt | aataactgat | ataattaaat | 1500 |
| tgaagctcta | atttgtgagt | ttagtataca | tgcatttact | tataatacag | ttttttagtt | 1560 |
| ttgctggccg | catcttctca | aatatgcttc | ccagcctgct | tttctgtaac | gttcaccctc | 1620 |
| taccttagca | tcccttccct | ttgcaaatag | tcctcttcca | acaataataa | tgtcagatcc | 1680 |
| tgtagagacc | acatcatcca | cggttctata | ctgttgaccc | aatgcgtctc | ccttgtcatc | 1740 |
| taaacccaca | ccgggtgtca | taatcaacca | atcgtaacct | tcatctcttc | cacccatgtc | 1800 |
| tctttgagca | ataaagccga | taacaaaatc | tttgtcgctc | ttcgcaatgt | caacagtacc | 1860 |
| cttagtatat | tctccagtag | ataggagcc | cttgcatgac | aattctgcta | acatcaaaag | 1920 |

```
gcctctaggt tcctttgtta cttcttctgc cgcctgcttc aaaccgctaa caatacctgg    1980
gcccaccaca ccgtgtgcat tcgtaatgtc tgcccattct gctattctgt atacacccgc    2040
agagtactgc aatttgactg tattaccaat gtcagcaaat tttctgtctt cgaagagtaa    2100
aaaattgtac ttggcggata atgcctttag cggcttaact gtgccctcca tggaaaaatc    2160
agtcaagata tccacatgtg ttttagtaa acaaattttg ggacctaatg cttcaactaa     2220
ctccagtaat tccttggtgg tacgaacatc caatgaagca cacaagtttg tttgcttttc    2280
gtgcatgata ttaaatagct tggcagcaac aggactagga tgagtagcag cacgttcctt    2340
atatgtagct ttcgacatga tttatcttcg tttcctgcag gttttttgttc tgtgcagttg   2400 ggttaagaat actgggcaat ttcatgtttc ttcaacacta catatgcgta tatataccaa    2460
tctaagtctg tgctccttcc ttcgttcttc cttctgttcg gagattaccg aatcaaaaaa    2520
atttcaaaga aaccgaaatc aaaaaaaaga ataaaaaaaa aatgatgaat tgaattgaaa    2580
agctagctta tcgatgataa gctgtcaaag atgagaatta attccacgga ctatagacta    2640
tactagatac tccgtctact gtacgataca cttccgctca ggtccttgtc ctttaacgag    2700
gccttaccac tcttttgtta ctctattgat ccagctcagc aaaggcagtg tgatctaaga    2760
ttctatcttc gcgatgtagt aaaactagct agaccgagaa agagactaga aatgcaaaag    2820
gcacttctac aatggctgcc atcattatta tccgatgtga cgctgcgrca gcttctcaat    2880
gatattcgaa tacgctttga ggagatacag cctaatatcc gacaaactgt tttacagatt    2940
tacgatcgta cttgttaccc atcattgaat tttgaacatc cgaacctggg agttttccct    3000
gaaacagata gtatatttga acctgtataa taatatatag tctagcgctt tacggaagac    3060
aatgtatgta tttcggttcc tggagaaact attgcatcta ttgcataggt aatcttgcac    3120
gtcgcatccc cggttcattt tctgcgtttc catcttgcac ttcaatagca tatctttgtt    3180
aacgaagcat ctgtgcttca ttttgtagaa caaaaatgca acgcgagagc gctaatttt    3240 caaacaaaga atctgagctg cattttaca gaacagaaat gcaacgcgaa agcgctattt    3300
taccaacgaa gaatctgtgc ttcattttg taaaacaaaa atgcaacgcg acgagagcgc    3360
taatttttca acaaagaat ctgagctgca ttttacaga acagaaatgc aacgcgagag    3420
cgctatttta ccaacaaaga atctatactt cttttttgtt ctacaaaaat gcatcccgag    3480
agcgctattt ttctaacaaa gcatcttaga ttacttttttt tctcctttgt gcgctctata    3540
atgcagtctc ttgataactt tttgcactgt aggtccgtta aggttagaag aaggctactt    3600
tggtgtctat tttctcttcc ataaaaaag cctgactcca cttcccgcgt ttactgatta    3660
ctagcgaagc tgcgggtgca ttttttcaag ataaaggcat ccccgattat attctatacc    3720
gatgtggatt gcgcatactt tgtgaacaga aagtgatagc gttgatgatt cttcattggt    3780
cagaaaatta tgaacggttt cttctatttt gtctctatat actacgtata ggaaatgttt    3840
acattttcgt attgttttcg attcactcta tgaatagttc ttactacaat ttttttgtct    3900
aaagagtaat actagagata aacataaaaa atgtagaggt cgagtttaga tgcaagttca    3960
aggagcgaaa ggtggatggg taggttatat agggatatag cacagagata tatagcaaag    4020
agatactttt gagcaatgtt tgtggaagcg gtattcgcaa tgggaagctc caccccggtt    4080
gataatcaga aaagccccaa aaacaggaag attgtataag caaatattta aattgtaaac    4140 gttaatatttt tgttaaaatt cgcgttaaat ttttgttaaa tcagctcatt ttttaacgaa    4200
tagcccgaaa tcggcaaaat cccttataaa tcaaaagaat agaccgagat agggttgagt    4260
```

| | |
|---|---|
| gttgttccag tttccaacaa gagtccacta ttaaagaacg tggactccaa cgtcaaaggg | 4320 |
| cggrdaaaaa gggtctatca gggcgatggc ccactacgtg aaccatcacc ctaatcaagt | 4380 |
| tttttggggt cgaggtgccg taaagcagta aatcggaagg gtaaacggat gcccccattt | 4440 |
| agagcttgac ggggaaagcc ggcgaacgtg gcgagaaagg aagggaagaa agcgaaagga | 4500 |
| gcggggggcta gggcggtggg aagtgtaggg gtcacgctgg gcgtaaccac cacacccgcc | 4560 |
| gcgcttaatg gggcgctaca gggcgcgtgg ggatgatcca ctagtacgga ttagaagccg | 4620 |
| ccgagcgggt gacagccctc cgaaggaaga ctctcctccg tgcgtcctcg tcctcaccgg | 4680 |
| tcgcgttcct gaaacgcaga tgtgcctcgc gccgcactgc tccgaacaat aaagattcta | 4740 |
| caatactagc ttttatggtt atgaagagga aaaattggca gtaacctggc cccacaaacc | 4800 |
| ttcaaatgaa cgaatcaaat taacaaccat aggatgataa tgcgattagt tttttagcct | 4860 |
| tatttctggg gtaattaatc agcgaagcga tgattttttga tctattaaca gatatataaa | 4920 |
| tgcaaaaact gcattaacca ctttaactaa tactttcaac attttcggtt tgtattactt | 4980 |
| cttattcaaa tgtaataaaa gtatcaacaa aaaattgtta atatacctct atactttaac | 5040 |
| gtcaaggaga aaaaccccg gatcggacta ctagcagctg taatacgact cactataggg | 5100 |
| aatattaagc ttggtaccga gctcggatct tcgaatgcat cgcgcgcacc gtacgtctcg | 5160 |
| agcggccgcc agtgtgatgg atatctgcag aattcggctt gtcaatatgc tgttcaagtc | 5220 |
| atggcaactg gcagcagcct ccgggctcct gtctggagtc ctcggcatcc cgatggacac | 5280 |
| cggcagccac cccattgagg ctgttgatcc cgaagtgaag actgaggtct tcgctgactc | 5340 |
| cctccttgct gcagcaggcg atgacgactg ggagtcacct ccatacaact tgctttacag | 5400 |
| gaatgccctg ccaattccac ctgtcaagca gcccaagatg atcattacca accctgtcac | 5460 |
| cggcaaggac atttggtact atgagatcga gatcaagcca tttcagcaaa ggatttaccc | 5520 |
| caccttgcgc cctgccactc tcgtcggcta cgatggcatg agccctggtc ctactttcaa | 5580 |
| tgttcccaga ggaacagaga ctgtagttag gttcatcaac aatgccaccg tggagaactc | 5640 |
| ggtccatctg cacggctccc catcgcgtgc ccctttcgat ggttgggctg aagatgtgac | 5700 |
| cttccctggc gagtacaagg attactactt tcccaactac caatccgccc gccttctgtg | 5760 |
| gtaccatgag rccacgcttt catgaagact gctgagaatg cctactttgg tcaggctggc | 5820 |
| gcctacatta tcaacgacga ggctgaggat gctctcggtc ttcctagtgg ctatggcgag | 5880 |
| ttcgatatcc ctctgatcct gacggccaag tactataacg ccgatggtac cctgcgttcg | 5940 |
| accgagggtg aggaccagga cctgtgggga gatgtcatcc atgtcaacgg acagccatgg | 6000 |
| cctttcctta acgtccagcc ccgcaagtac cgtttccgat tcctcaacgc tgccgtgtct | 6060 |
| cgtgcttggc tcctctacct cgtcaggacc agctctccca acgtcagaat tcctttccaa | 6120 |
| gtcattgcct ctgatgctgg tctccttcaa gcccccgttc agacctctaa cctctacctt | 6180 |
| gctgttgccg agcgttacga gatcattatt gacttcacca actttgctgg ccagactctt | 6240 |
| gacctgcgca acgttgctga gaccaacgat gtcggcgacg aggatgagta cgctcgcact | 6300 |
| ctcgaggtga tgcgcttcgt cgtcagctct ggcactgttg aggacaacag ccaggtcccc | 6360 |
| tccactctcc gtgacgttcc tttccctcct cacaaggaag gccccgccga caagcacttc | 6420 |
| aagtttgaac gcagcaacgg acactacctg atcaacgatg ttggctttgc cgatgtcaat | 6480 |
| gagcgtgtcc tggccaagcc cgagctcggc accgttgagg tctgggagct cgagaactcc | 6540 |
| tctggaggct ggagccaccc cgtccacatt caccttgttg acttcaagat cctcaagcga | 6600 |
| actggtggtc gtggccaggt catgccctac gagtctgctg gtcttaagga tgtcgtctgg | 6660 |

```
ttgggcaggg gtgagaccct gaccatcgag gcccactacc aaccctggac tggagcttac   6720
atgtggcact gtcacaacct cattcacgag gataacgaca tgatggctgt attcaacgtc   6780
accgccatgg aggagaaggg atatcttcag gaggacttcg aggaccccat gaaccccaag   6840
tggcgcgccg ttccttacaa ccgcaacgac ttccatgctc gcgctggaaa cttctccgcc   6900
gagtccatca ctgcccgagt gcaggagctg gccgagcagg agccgtacaa ccgcctcgat   6960
gagatcctgg aggatcttgg aatcgaggag tagtctagag ggccgcatca tgtaattagt   7020
tatgtcacgc ttacattcac gccctccccc cacatccgct ctaaccgaaa ggaaggagt    7080 tagacaacct gaagtctagg tccctattta ttttttata gttatgttag tattaagaac    7140
gttatttata tttcaaattt ttctttttt tctgtacaga cgcgtgtacg catgtaacat    7200
tatactgaaa accttgcttg agaaggtttt gggacgctcg aaggctttaa tttgcggcc   7259
```

<210> SEQ ID NO 4
<211> LENGTH: 1082
<212> TYPE: DNA
<213> ORGANISM: Artificial Sequence
<220> FEATURE:
<223> OTHER INFORMATION: Description of Artificial Sequence: Synthetic
      DNA encoding Organophosphate Hydrolase

<400> SEQUENCE: 4

```
ccatggccaa caagcacctg agcctctccc tcttcctcgt gctcctcggc ctctccgcct   60
ccctcgccag cggcaccggc gaccgcatca acaccgtgcg cggcccgatc accatctccg   120
aggccggctt caccctcacc cacgagcaca tctgcggctc ctccgccggc ttcctccgcg   180
cctggccgga gttcttcggc tcccgcaagg ccctcgccga aaggccgtg cgcggcctcc   240 gccgcgcccg cgccgccggc gtgcgcacca tcgtggacgt gtccaccttc gacatcggcc   300
gcgacgtgtc cctcctcgcc gaggtgtccc gcgccgcca cgtgcacatc gtggccgcca   360
ccggcctctg gttcgacccc ccgctctcca tgcgcctccg ctccgtggag gagctcaccc   420
agttcttcct ccgcgagatc cagtacggca tcgaggacac cggcatccgc gccggcatca   480
tcaaggtggc caccaccggc aaggccaccc cgttccagga gctcgtgctc aaggccgccg   540
cccgcgcctc cctcgccacc ggcgtgccgg tgaccaccca caccgccgcc tcccagcgcg   600
acggcgagca gcaggccgcc atcttcgagt ccagggcct ctccccgtcc cgcgtgtgca   660
tcggccactc cgacgacacc gacgacctct cctacctcac cgccctcgcc gcccgcggct   720
acctcatcgg cctcgaccac atcccgcact ccgccatcgg cctcgaggac aacgcctccg   780
cgtccgccct cctcggcatc cgctcctggc agacccgcgc cctcctcatc aaggccctca   840
tcgaccaggg ctacatgaag cagatcctcg tgtccaacga ctggctcttc ggcttctcct   900
cctacgtgac caacatcatg gacgtgatgg accgcgtgaa cccggacggc atggccttca   960
tcccgctccg cgtgatcccg ttcctccgcg agaagggcgt gccgcaggag accctcgccg   1020
gcatcaccgt gaccaacccg gcccgcttcc tctccccgac cctccgcgcc tcctgagtta   1080
ac                                                                  1082
```

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence:
      Illustrative motif -continued

```
<400> SEQUENCE: 5

Lys Asp Glu Leu
1
```

METHOD OF INCREASING RECOVERY OF HETEROLOGOUS ACTIVE ENZYMES PRODUCED IN PLANTS

This application is a continuation-in-part of previously filed and co-pending application U.S. Ser. No. 60/211,732, filed Jun. 15, 2000, which is incorporated by reference in its entirety.

BACKGROUND OF THE INVENTION

Plants as biofactories for the production of proteins is a technology that is being employed by a number of groups for edible vaccines, pharmaceuticals and industrial enzymes (Hood and Jilka, 1999; Hood and Howard, 1999). Pharmaceutical and vaccine production in plants has several advantages in that the material contains no contaminating organisms and can be directly consumed (Hood and Jilka, 1999; Hood and Howard, 1999). Production of industrial enzymes in plants provides the possibility of considerably reduced production costs, the benefit of recovered costs through sale of by products, easier transportation and reduced chance of contamination.

Over-expression of an industrial enzyme in a transgenic plant requires quite high expression levels to make the system economically viable, a condition that has been achieved for several proteins, e.g. the diagnostic protein, avidin (Hood et al. 1997) and laccase (WO 00/20615). Using plants as biofactories for industrial enzyme production provides considerable advantages over traditional methods of such enzyme production, since plants provide easier transport and cost savings, but also can be far more readily produced in large quantities than when produced in bacteria or fungi, for example, allowing for even further increases in the amount of enzyme which may be produced.

Achieving high levels of enzyme production in plants is impacted by several factors, such as location of expression of the enzyme within specific tissues and within particular subcellular compartments to insulate the plant tissues from the activity of the enzymes. Thus, in WO 00/20615, it is discussed that preferentially directing expression to the seed of the plant and also to plant cell wall tissue and to the endoplasmic reticulum of the plant cell is advantageous in increasing enzyme protein production.

In addition to increased concentrations of enzymes, it is desired that the enzymes exhibit high activity. While some enzymes depend for activity only on their structure as proteins, others also require one or more non-protein components, termed cofactors. The cofactors may be a metal ion or an organic molecule called a coenzyme and some enzymes require both. Cofactors are generally stable to heat, where most enzyme proteins lose activity on heating. The term holoenzyme is used to refer to the catalytically active enzyme-cofactor complex. When the cofactor is absent, the protein, which is catalytically inactive by itself, is called an apoenzyme. Transitional metal ions are important cofactors in enzymatic transformation of nonmineral substances in anabolic and catabolic processes within plant cells. Therefore, the presence of such transitional metal ions may be important in providing an active enzyme.

Plants produce many of these cofactors as an essential element of their vegetative growth process in considerable amounts. Thus, one would presume that the plant would supply adequate quantities of the metal ion needed to produce active enzyme. For example, about four atoms of copper are needed for each molecule of laccase in order to produce active laccase enzyme. A person skilled in the art would expect there would be more than enough copper available since there is a considerable amount of copper for enzyme uptake in the plant. In fact, there is about 20 ppm copper in normal corn tissues, which would be sufficient to support laccase accumulation at much greater than 5ng/mg seed weight (see Table 1).

TABLE 1

Copper Requirements for Laccase Produced in Corn Seed.

| ng Laccase/mg Corn Seed (ppm) | pg Copper/mg Corn Seed (ppb) Required |
| --- | --- |
| 5 | 18 |
| 50 | 180 |
| 200 | 720 |

Thus there is about a thousand times more copper in the corn plant than is necessary to support laccase expression at 5 ng/mg. There should be more than enough available for production of active laccase when it is produced in a plant. Instead, the inventors have found this is not the situation. Unless such transition metals are added over and above what is pesent in plants, the amount of active enzyme is reduced. By providing such cofactors during plant development and/or during or after protein extraction from the plant tissue, the amount of active enzyme is increased, at times greater than ten fold. This is particularly surprising, since attempts to add the metal cofactor copper to laccase fungal expression systems have not met with success in improving activation levels of the enzyme.

Additionally, the inventors have found that by incubating the metal and enzyme while controlling the temperature during incubation, either during extraction or after, it increases the recovery of active protein by such possible mechanisms as refolding and stabilization of the protein or reoxidation of the transition metal. Negative salt ions added during or after extraction of the enzyme with the metal further aid in improving recovery of active enzyme.

Optimal conditions have also been discovered by the inventors for improved recovery of laccase using the copper cofactor.

SUMMARY OF THE INVENTION

The invention relates to the discovery by the inventors that while transgenic plants expressing enzymes contain considerable quantities of transitional metal cofactors needed for certain enzyme activation, it is necessary to provide additional metal ions in order to increase recovery of active enzyme from plants.

Therefore it is an object of the invention to provide a process for increasing recovery of active enzyme from a plant where that enzyme requires a transitional metal cofactor, by providing additional metal cofactor to the enzyme, either during plant development, during extraction of the enzyme from the plant, following extraction of the enzyme from the plant, or during all three phases.

A further object of the invention is to increase recovery of active enzyme from a plant in which a transitional metal cofactor has been added by further adding a negative salt ion.

Yet another object of the invention is increasing recovery of active laccase which is produced by a plant having a nucleotide sequence encoding laccase by providing additional copper to such laccase enzymes.

An object of the invention is a method of increasing recovery of active laccase which is produced in a plant having a nucleotide sequence encoding laccase by adding a negative salt ion to the laccase enzyme, preferably where the ion is chloride.

A further object of the invention is a method of increasing recovery of active organophosphate hydrolase which is produced by a plant having a nucleotide sequence encoding organophosphate hydrolase by providing additional transitional metals such as zinc, nickel, cobalt or manganese to such organophosphate hydrolase enzymes.

An object of the invention is a method of increasing recovery of active ogranophosphate hydrolase enzymes by adding a negative salt ion to the enzyme, preferably where the ion is chloride.

The invention further has as an objective incubating the metal and enzyme while controlling temperature of the incubation. The temperature that provides improved recovery will vary with time of incubation but practical considerations indicate that recovery is improved when the incubation with the metal is for up to several weeks when at 4° C., preferably up to several days when incubated at room temperature (20°–27° C.); preferably at room temperature up to 37° C. for about 20 to 60 minutes when a negative salt ion is added; and up to three hours at 50° C. Still another object of the invention is to provide for optimal yield of active laccase produced in plants by using a solution to extract the laccase having a copper salt solution of 0.05mM to 1M copper, preferably 1 mM to 100 mM copper, more preferably 10 to 30 mM copper

DESCRIPTION OF DRAWINGS

FIGS. 1A–C sets forth the nucleotide sequences of the Trametes laccase gene used in the experiments set forth below. SEQ ID NO: 1

FIG. 15A shows LCB flour extracted with sodium acetate and incubated with varying amounts of copper added either with or without sodium chloride added. The solid symbols represent the data for incubating at room temperature. The white symbols represent the laccase activity when incubated for one hour at 50° C.

FIG. 15B shows LCG flour extracted and incubated similarly.

FIGS. 16A–E shows the nucleotide sequences of the Stachybotrys gene used in the experiments set forth below. SEQ ID NO: 3

FIG. 20 shows the nucleotide sequences of the organophosphate hydrolase gene. SEQ ID NO:4

DETAILED DESCRIPTION OF PREFERRED EMBODIMENTS

Figure 2A:
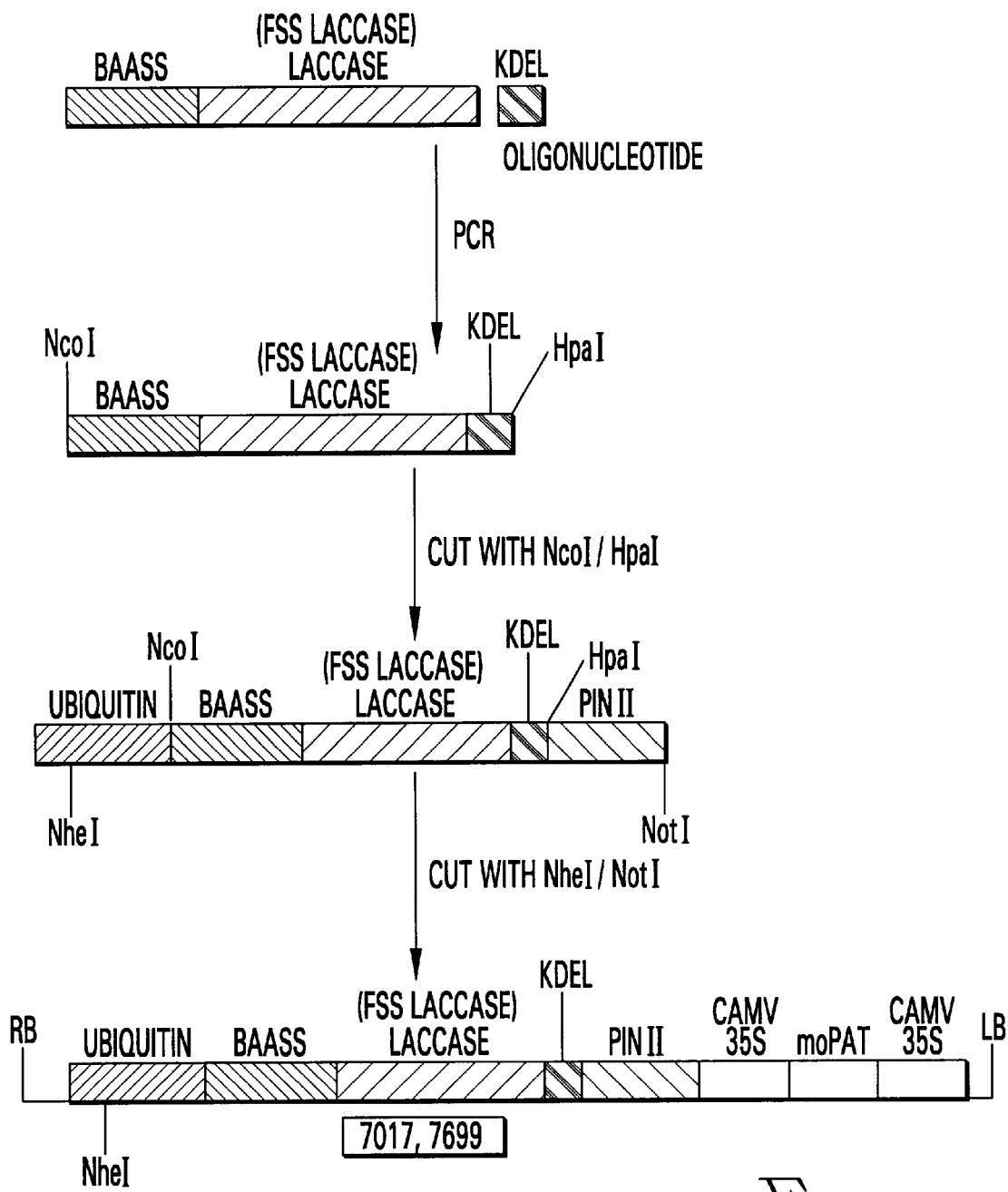
FIGS. 2A–D is a schematic representation of the process used to generate laccase and OPH plasmids described.
Figure 2B:
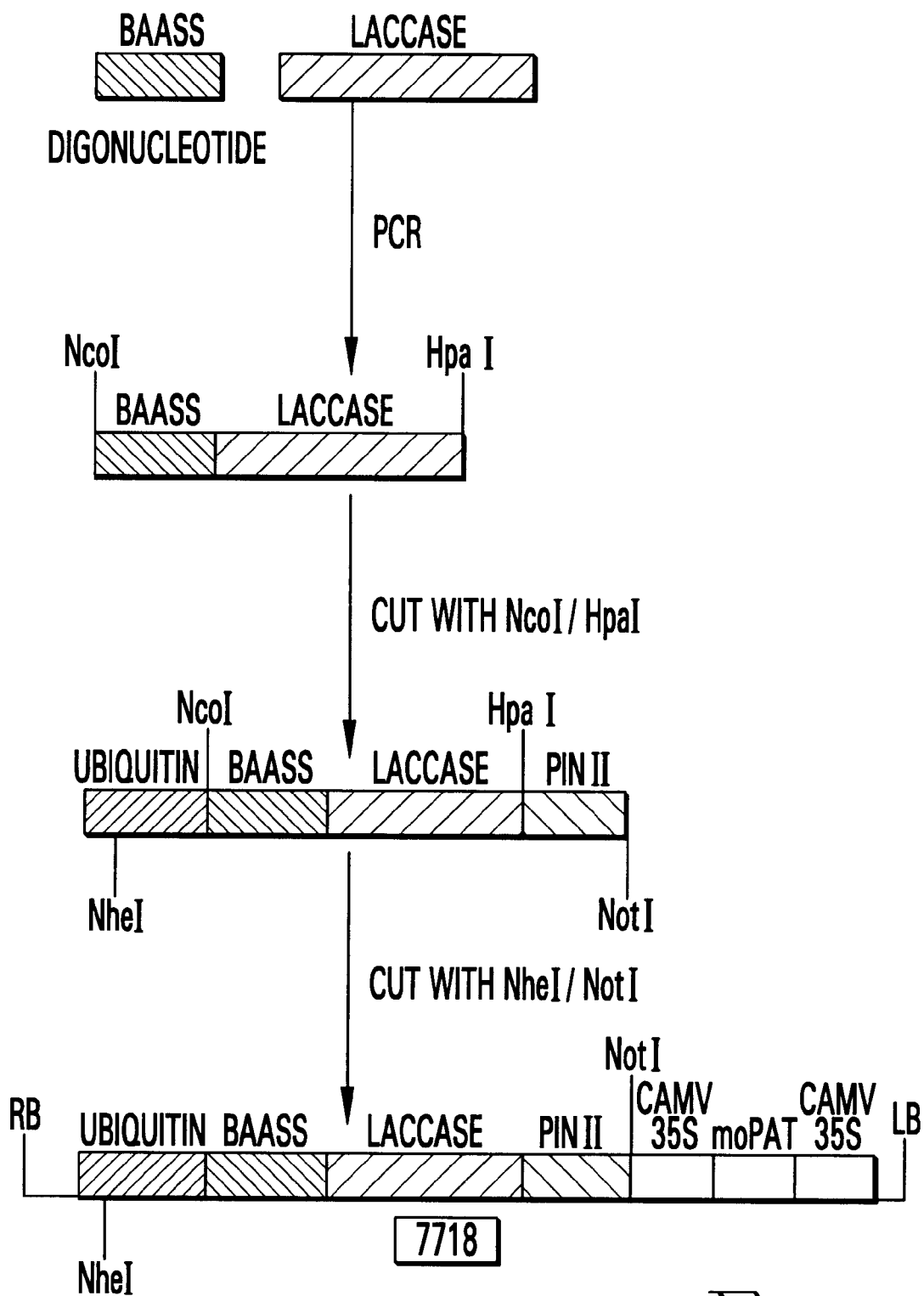
Figure 2C:
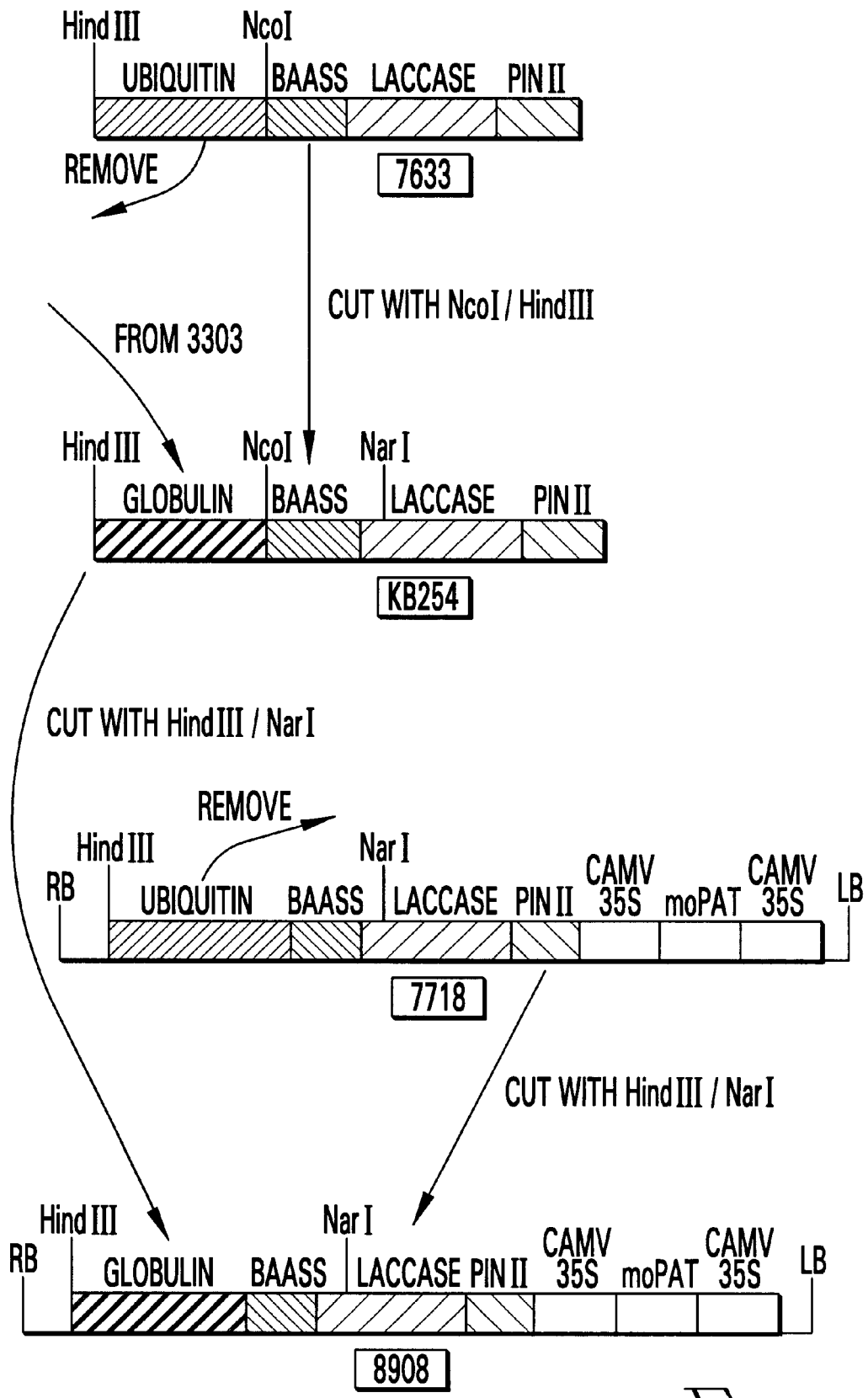
Figure 2D:
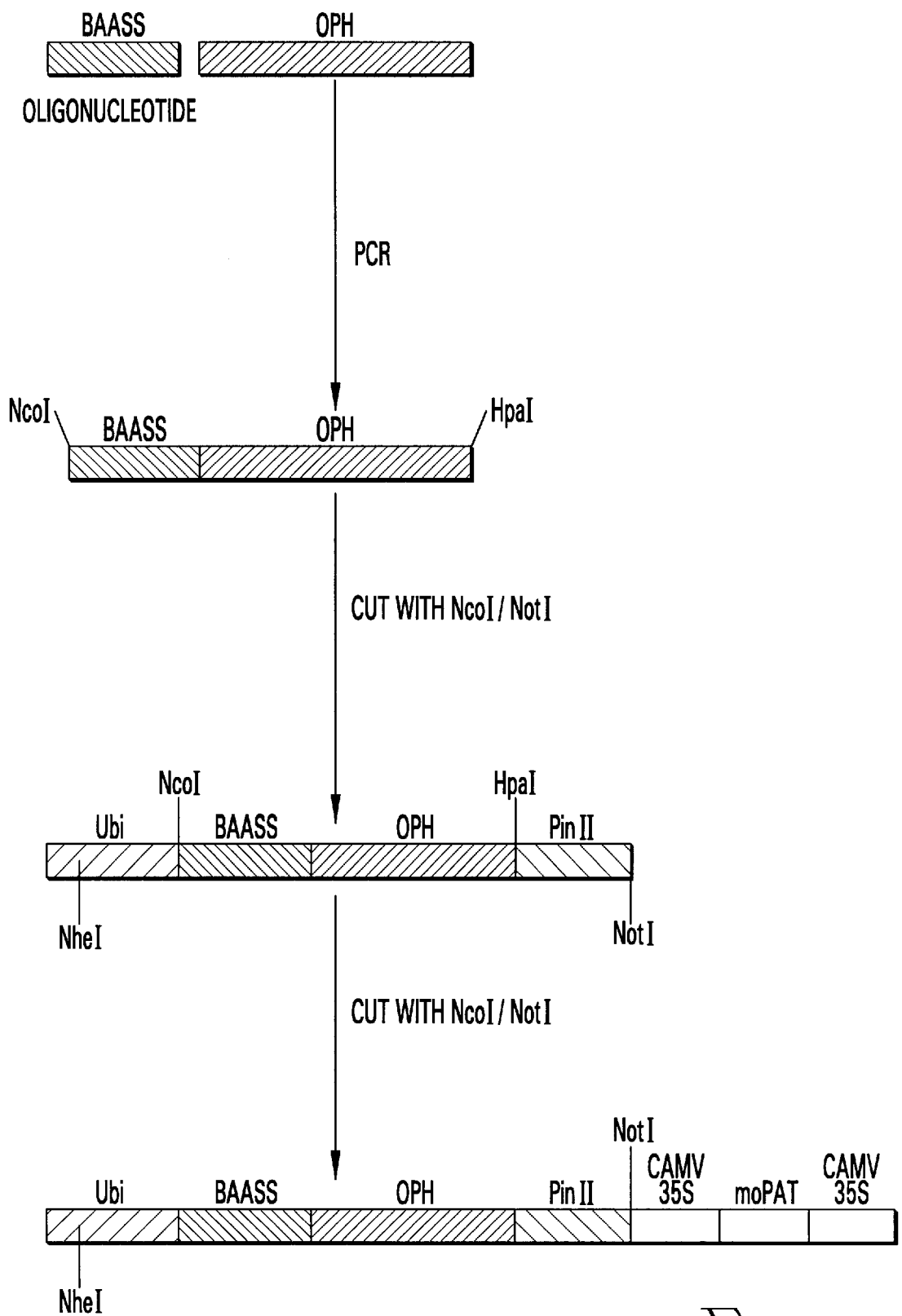

The following is presented to illustrate the preferred embodiments of the invention. All references are incorporated herein by reference.

In the present invention, the inventors have discovered that recovery of active enzyme can be considerably improved when that enzyme is one which depends for activity on a metal cofactor, by exposure of the plant tissue to enzyme cofactors either during plant development or when extracting or activating the enzyme or during all three steps. This increases the amount of active as opposed to inactive enzyme that may be obtained through plant production.

Metal ions may either act as the primary catalytic center, as a bridging group to bind substrate and enzyme together by forming a coordination complex, or an agent stabilizing the conformation of the enzyme protein in its catalytically active form. Enzymes which require metal ions are called metalloenzymes. The table below lists some of those enzymes which require metal ions as cofactors.

TABLE 2

| Metal cofactor | Enzyme |
| --- | --- |
| $Zn^{2-}$ | Alcohol dehydrogenase |
| | Carbonic anhydrase |
| | Carboxypeptidase |
| | Glucose-6-phosphate dehydrogenase |
| | Trioesphophate dehydrogenases |
| | Phosphodiesterase |
| $Mg^{2+}$ | Phosphohydrolases |
| | Endonucleases |
| | Phosphotransferases |
| $Mn^{2+}$ | Arginase |
| | Phosphotransferases |
| $Fe^{2+}$ or $Fe^{3+}$ | Cytochromes |
| | Peroxidases |
| | Catalase |
| | Ferredoxin |
| $Cu^{1+}$ ($Cu^{2+}$) | Tyrosinase |
| | Cytochrome oxidase |
| | Ascorbic acid oxidase |
| | Laccase |
| $K^{1+}$ | Pyruvate kinase (also requires $Mg^{2+}$) |
| $Na^{1+}$ | Plasma membrane ATPase (also requires $K^{1+}$ and $Mg^{2+}$) |

For a thorough discussion of enzymes, coenzymes and their background, see Lehninger, A. Chapter 8 "Enzymes: kinetics and inhibition" *Biochemistry*, second edition, The Johns Hopkins University School of Medicine (1977), Worth Publishers, Inc.

Transitional metal ions are involved as cofactors in plant processes. By transitional metal ions, it is meant those transitional elements found in Group II of the periodic chart of the elements. Those elements known to be critical for growth of multicellular plants which are transitional metals include, for example, copper, zinc, manganese, iron. See e.g. Chapter 18, D. W. Rains "Mineral Metabolism" *Plant Biochemistry*, Third Edit. Bonner and Varner, eds., Academic Press (1976). Such transitional metal ions are found abundantly in the soil and in healthy plants. The table below lists several of the transitional metals known to be critical for growth of multicellular plants. They are shown in terms of relative numbers present in plants with respect to molybdenum.

TABLE 3

| | Concentration in dry matter | | Relative number |
| --- | --- | --- | --- |
| Element | $10^{-6}$ atoms/gm | $\mu g/gm$ or ppm | of atoms with respect to molybdenum |
| Molybdenum (for comparison) | 0.001 | 0.1 | 1 |
| Copper | 0.1 | 6 | 100 |
| Zinc | 0.3 | 20 | 300 |
| Manganese | 1.0 | 50 | 1000 |
| Iron | 2.0 | 100 | 2000 |

Since there is no short supply of the transitional metals in the environment and in the plant, it would be expected that when a heterologous enzymatic protein is produced in the plant, there would be ample metal cofactors available to produce active enzyme. However, the inventors have found that the amount of active enzyme produced by the plants was lower than expected.

Thus, when producing an enzyme in a plant where the enzyme requires a cofactor ordinarily available in a plant, one must make available the metal ion by adding it to the plant while it is growing, such as spraying in the field, or by extracting the enzyme with the metal ion added to the extracting solutions, or exposing the enzyme extracted from the plant to the metal. By indicating that the enzyme is exposed to the metal cofactor, one skilled understands that any manner of exposing the metal to the enzyme will suffice. For example, the enzyme may come in contact with the metal cofactor indirectly in plant development, or directly, as in the processing mechanism. The enzyme and metal may be incubated together, meaning exposed for a select period of time.

By way of example, copper ion is added when producing an enzyme in a plant where the enzyme requires copper ion as a cofactor. Copper ion is commonly found in a group of enzymes in which oxygen is used directly in the oxidation of substrate. Such oxidases include tyrosinase, laccase, and ascorbic acid oxidase. An oxidized product requires addition of ¼ $O_2$ to the substrate. Copper ion is suggested to mediate these enzyme transformations by undergoing cyclic oxidation and reduction. See Rains, supra and Price, C. A. *Molecular Approaches to Plant Physiology* McGraw-Hill, New York (1970). In the example set forth below, copper ion is added to plant-produced laccase during or after extraction, and also can be added during tissue culture or field spraying. Zinc is a transitional metal commonly associated with auxin and is believed to prevent oxidation of the hormone in plants. Various enzyme systems are known to require zinc, such as alcohol dehydrogenase, glucose 6-phosphate and trioesphophate dehydrogenases, carbonic anhydrase, carboxypeptidase and phosphodiesterase. Manganese is associated as having a role in photosynthesis in plants, and is involved in oxidation-reduction processes and decarboxylation and hydrolysis reactions. It is involved in a number of plant enzyme systems and is a cofactor for arginase and phosphotransferases. Iron functions in plants as both a structural component and as a cofactor of enzymic reactions. Oxidation-reduction reactions are most commonly associated with iron-containing systems. It is also a cofactor in a number of enzymes (see table 2 for examples).

More than one transitional metal may be a useful metal in increasing active enzyme recovered. For example, zinc, manganese, cobalt, magnesium and nickel are potentially useful in improving recovery of active organophosphate hydrolase. By testing the various options, one can easily determine which metal is the optimal choice in this process. Using OPH as an example, it is clear that cobalt is the best metal for recovery of the optimal levels of active enzyme, but manganese, nickel, and zinc are also effective.

While the examples are directed to particular enzymes, it is evident that any enzyme produced in a plant by introduction of heterologous DNA encoding the enzyme, where that enzyme requires a transitional metal cofactor, is encompassed within the scope of the invention.

Addition of a negative salt ion to the recovery process, either during extraction or afterwards, may yield further increases in active enzyme obtained from the plant. The salt ion or metal salt may be added to the process. Again, which ion provides optimal recovery can be readily determined in a comparison of different ions used in the process. Any negative ion non-toxic to the plant is an option. Among the options readily apparent to one skilled in the art are chloride, sulfate, phosphate, carbonate and bicarbonate ions. Some of these ions have been associated as potential inhibitors of the enzyme activity. Surprisingly, the inventors have found that not only are such ions effective in aiding enzyme recovery, but these salts can be particularly effective. When using an ion that is an inhibitor of the enzyme, it is necessary to remove it by any one of the methods well known to those skilled in the art, such as dilution, column removal or the like (Pohl, T. 1990). When the ion is removed, the metal cofactor remains and the apparent amount of active enzyme is increased. For example, chloride is an inhibitor of laccase activity, but when used as a salt with copper, it considerably improves active laccase recovery from plants (2–5 fold). It is believed the ion acts on the enzyme to allow easier entry of the necessary transitional metal thereby increasing the amount of active enzyme produced.

Additional improvement in yield of active enzyme can be achieved by incubating the metal and enzyme while controlling the temperature during incubation. While not wishing to be bound by any theory, it is believed the plant produces the protein in a form such that the incubation process facilitates incorporation of the required metal ions thus forming an active complex and enzyme configuration. For example, as described below, the addition of copper salt to a transgenic plant that makes heterologous laccase, during extraction of laccase from the plant tissue or after extraction, increases the yield of active laccase. This is surprising in light of the lack of success in increasing the yield of active laccase by adding copper salt to fermenters with and after fermentation of laccase-producing fungi.

The temperature providing improved recovery will vary with time of incubation but the temperature must be one that does not denature the enzyme during the time it is incubating. Generally, recovery is improved when the temperature is not less than 4° C. in which case the activation will proceed too slowly, nor more than 60° C., where the protein will break down fairly quickly. However, there are practical limitations for an optimal recovery that is not cost prohibitive but is reasonable in terms of time for the reaction. Thus, improved active enzyme recovery over several weeks is possible when the temperature is low, at 4° C. In fact, at this temperature, the metal solution and enzyme can be left indefinitely, in storage, for example. When room temperature, that is about 20° C. to 27° C. is used, incubation can result in good active enzyme levels in as little as a few minutes but can continue for as long as 18 to 24 hours. At 50° C., the enzyme is mostly activated nearly at the onset of contact, and continues effectively up to three hours. However, when used with a salt ion, a lower temperature is more preferred, as breakdown of the product can occur too quickly when 50° C. conditions are applied.

Selecting the optimal transitional metal and concentration, the salt ion that may be added and its concentration is a matter of comparison of the options. The time and temperature preferred will be determined by one skilled in the art depending upon economics and preferred production methods.

For example, copper was added to increase active laccase production. Copper concentrations ranging from 0.05 mM to 100 mM copper were used in a first comparison. For LCB, as described in Example 1 below, a plant producing lower levels of laccase (about 3 ng/mg total laccase) the optimal level of copper concentration was about 10 mM. With higher levels of laccase expression as with LCG, also described below (about 30 ng/mg total), it is beneficial to use higher concentrations of copper. Thus the optimal copper concentration was about 30 mM copper. Chloride was selected as the salt to use with copper in laccase activity increase after side by side comparisons with other salt ions.

Time and temperature for incubation can be determined as was done in the experiments below, and, in general, by using temperatures ranging from 4° C. up to 50° C. and measuring recovery. Measurements were taken both with and without use of the chloride ion in the process. First measurements occurred at five minutes, then at ten minutes, 20 minutes, 30 minutes, one hour, three hours, 18 hours, and one week. It was found that most of the active laccase was recovered at 50° C. at about five minutes and continued up to one hour, or at room temperature in about five minutes to three to four hours. The experiment was repeated at 4° C. At 24 hours active laccase was still being recovered, so the process, while effective, was not as practical for recovery compared to higher temperature exposure. All three experiments were repeated using 10 mM copper salt, 30 mM copper salt and 100 mM copper salt. Optimal recovery occurred using 10 mM copper salt with LCB. When the higher expressing LCG was used, optimal recovery occurred at 50° C. with 30 mM copper salt, or at room temperature when 0.5 M NaCl was added. In addition to higher amounts of copper salt, the LCG required the presence of the chloride salt for maximal laccase recovery. When chloride salt was used, preferred temperatures were 18° C. to 37° C. and maximum recovery of active laccase occurred by 10 to 60 minutes with one hour selected as most usable.

This straightforward experimental process can be used to determine optimal parameters for each of the enzymes, metals and negative salt ions described herein.

Genes which encode enzymes of interest are available to one skilled in the art and examples are set forth below of sequences for genes encoding laccases and organophosphate hydrolase. It will be evident to one skilled in the art that any gene which encodes an enzyme requiring a transitional metal cofactor is encompassed within the scope of the invention.

The methods available for putting together a gene as described above for improved expression described above can differ in detail. However, the methods generally include the designing and synthesis of overlapping, complementary synthetic oligonucleotides which are annealed and ligated together to yield a gene with convenient restriction sites for cloning. The methods involved are standard methods for a molecular biologist.

Once the gene has been isolated which encodes such enzymes, it is placed into an expression vector by standard methods. The selection of an appropriate expression vector will depend upon the method of introducing the expression vector into host cells. A typical expression vector contains prokaryotic DNA elements coding for a bacterial replication origin and an antibiotic resistance gene to provide for the growth and selection of the expression vector in the bacterial host; a cloning site for insertion of an exogenous DNA sequence, which in this context would code for the enzyme of interest; eukaryotic DNA elements that control initiation of transcription of the exogenous gene, such as a promoter; and DNA elements that control the processing of transcripts, such as transcription termination/polyadenylation sequences. It also can contain such sequences as are needed for the eventual integration of the vector into the plant chromosome.

In a preferred embodiment, the expression vector also contains a gene encoding a selection marker which is functionally linked to a promoter that controls transcription initiation. For a general description of plant expression vectors and reporter genes, see Gruber et al. (1993).

Promoter elements employed to control expression of the enzyme encoding gene and the selection gene, respectively, can be any plant-compatible promoter. Those can be plant gene promoters, such as, for example, the ubiquitin promoter, the promoter for the small subunit of ribulose-1, 5-bis-phosphate carboxylase, or promoters from the tumor-inducing plasmids from *Agrobacterium tumefaciens*, such as the nopaline synthase and octopine synthase promoters, or viral promoters such as the cauliflower mosaic virus (CaMV) 19S and 35S promoters or the figwort mosaic virus 35S promoter. See Kay et al. (1987) and European patent application No. 0 342 926. See international application WO 91/19806 for a review of illustrative plant promoters suitably employed in the present invention. The range of available plant compatible promoters includes tissue specific and inducible promoters. In one embodiment of the present invention, the exogenous DNA is under the transcriptional control of a plant ubiquitin promoter. Plant ubiquitin promoters are well known in the art, as evidenced by European patent application no. 0 342 926.

Alternatively, a tissue specific promoter can be provided to direct transcription of the DNA preferentially to the seed. One such promoter is the globulin promoter. This is the promoter of the maize globulin-1 gene, described by Belanger, F. C. and Kriz, A. L. (1991). It also can be found as accession number L22344 in the Genebank database. Another example is the phaseolin promoter. See, Bustos et al. (1989).

One option for use of a selective gene is a glufosinate-resistance encoding DNA and in an embodiment can be the phosphinothricin acetyl transferase ("PAT") or maize optimized PAT gene (Jayne et al, U.S. Pat. No. 6,096,947) under the control of the CaMV 35S promoter. The gene confers resistance to bialaphos. See, Gordon-Kamm et al. (1990); Uchimiya et al., (1993), and Anzai et al., *Mol. Gen. Gen.* 219:492 (1989).

It may also be desirable to provide for inclusion of sequences to direct expression of the protein to a particular part of the cell. A variety of such sequences are known to those skilled in the art. For example, if it is preferred that expression be directed to the cell wall, this may be accomplished by use of a signal sequence and one such sequence is the barley alpha amylase signal sequence, (Rogers, 1985). Another example is the brazil nut protein signal sequence when used in canola or other dicots. Another alternative is to express the enzyme in the endoplasmic reticulum of the plant cell. This may be accomplished by use of a localization sequence, such as KDEL. This sequence contains the binding site for a receptor in the endoplasmic reticulum. Munro, S. and Pelham, H. R. B. (1987).

Obviously, many variations on the promoters, selectable markers and other components of the construct are available to one skilled in the art.

In accordance with the present invention, a transgenic plant is produced that contains a DNA molecule, comprised of elements as described above, integrated into its genome so that the plant expresses a heterologous enzyme-encoding DNA sequence. In order to create such a transgenic plant, the expression vectors containing the gene can be introduced into protoplasts, into intact tissues, such as immature embryos and meristems, into callus cultures, or into isolated cells. Preferably, expression vectors are introduced into intact tissues. General methods of culturing plant tissues are provided, for example, by Miki et al, (1993) and by Phillips et al., (1988). The selectable marker incorporated in the DNA molecule allows for selection of transformants.

Methods for introducing expression vectors into plant tissue available to one skilled in the art are varied and will depend on the plant selected. Procedures for transforming a wide variety of plant species are well known and described throughout the literature. See, for example, Miki et al., supra; Klein et al., (1992); and Weisinger et al., (1988). For example, the DNA construct may be introduced into the genomic DNA of the plant cell using techniques such as microprojectile-mediated delivery, Klein et al., (1987); electroporation, Fromm et al., (1985); polyethylene glycol (PEG) precipitation, Paszkowski et al., (1984); direct gene transfer, WO 85/01856 and EP No. 0 275 069; in vitro protoplast transformation, U.S. Pat. No. 4,684,611; and microinjection of plant cell protoplasts or embryogenic callus. Crossway, (1985). Co-cultivation of plant tissue with *Agrobacterium tumefaciens* is another option, where the DNA constructs are placed into a binary vector system. Ishida et al., (1996). The virulence functions of the Agrobacterium tumefaciens host will direct the insertion of the construct into the plant cell DNA when the cell is infected by the bacteria. See, for example Horsch et al., (1984), and Fraley et al. (1983).

Standard methods for transformation of canola are described by Moloney et al., (1989). Corn transformation is described by Fromm et al. (1990) and Gordon-Kamm et al, supra. Agrobacterium is primarily used in dicots, but certain monocots such as maize can be transformed by Agrobacterium. U.S. Pat. No. 5,550,318. Rice transformation is described by Hiei et al., (1994), Christou et al., (1991). Wheat can be transformed by techniques similar to those used for transforming corn or rice. Sorghum transformation is described by Casas et al, supra and by Wan et al., (1994). Soybean transformation is described in a number of publications, including U.S. Pat. No. 5,015,580.

In one preferred method, the Agrobacterium transformation methods of Ishida supra and also described in U.S. Pat. No. 5,591,616, are generally followed, with modifications that allow the inventors to recover transformants from HII maize. The Ishida method uses the A188 variety of maize that produces Type I callus in culture. In one preferred embodiment the High II maize line is used which initiates Type II embryogenic callus in culture. While Ishida recommends selection on phosphinothricin when using the bar or PAT gene for selection, another preferred embodiment provides for use of bialaphos instead.

The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an E. coli specific replication origin, it cannot survive in Agrobacterium without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA 101, selecting for spectinomycin resistance. The plasmid is isolated to assure that the EHA101 contains the plasmid.

Further, the Ishida protocol as described provides for growing fresh culture of the Agrobacterium on plates, scraping the bacteria from the plates, and resuspending in the co-culture medium as stated in the '616 patent for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose and 36 g glucose, all at a pH of 5.8.In a further preferred method, the bacteria are grown overnight in a 1 ml culture, then a fresh 10 ml culture re-inoculated the next day when transformation is to occur. The bacteria grow into log phase, and are harvested at a density of no more than OD600=0.6 and preferably between 0.2 and 0.5. The bacteria are then centrifuged to remove the media and resuspended in the co-culture medium. Since Hi II is used, medium preferred for Hi II is used. This medium is described in considerable detail by Armstrong, C. I. and Green C. E. "Establishment and maintenance of friable, embryogenic maize callus and involvement of L-proline" Planta (1985) 154:207–214. The resuspension medium is the same as that described above. All further Hi II media are as described in Armstrong et al. The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

It is preferred to select the highest level of expression of the enzyme, and it is thus useful to ascertain expression levels in transformed plant cells, transgenic plants and tissue specific expression. For enzymes, one such detection method is to determine the activity of the enzyme using a substrate specific for the type of reaction catalysed by the enzyme. For example, laccase activity can be detected using any number of colorometric substrates such ABTS (2,2'-Azino-bis(3-ethylbenzthiazoline-6-sulfonic acid) by incubating solutions of laccase with the substrate in excess in a buffer at the appropriate pH and monitoring the change in absorbance over time.

The levels of expression of the gene of interest can be enhanced by the stable maintenance of an enzyme encoding gene on a chromosome of the transgenic plant. Use of linked genes, with herbicide resistance in physical proximity to the enzyme encoding gene, would allow for maintaining selective pressure on the transgenic plant population and for those plants where the genes of interest are not lost.

With transgenic plants according to the present invention, enzyme can be produced in commercial quantities. Thus, the selection and propagation techniques described above yield a plurality of transgenic plants which are harvested in a conventional manner. The plant with the enzyme can be used in the processing, or the enzyme extracted. Enzyme extraction from biomass can be accomplished by known methods which are discussed, for example, by Heney and Orr (1981).

It is evident to one skilled in the art that there can be loss of material in any extraction method used. Thus, a minimum level of expression is required for the process to be economically feasible. For the relatively small number of transgenic plants that show higher levels of expression, a genetic map can be generated, via conventional RFLP and PCR analysis, which identifies the approximate chromosomal location of the integrated DNA molecule. For exemplary methodologies in this regard, see Glick and Thompson (1993). Genetic mapping can be effected, first to identify DNA fragments which contain the integrated DNA and then to locate the integration site more precisely. This further analysis would consist primarily of DNA hybridizations, subcloning and sequencing. The information thus obtained would allow for the cloning of a corresponding DNA fragment from a plant not engineered with a heterologous enzyme encoding gene. (Here, "corresponding" refers to a DNA fragment that hybridizes under stringent conditions to the fragment containing the enzyme encoding gene). The cloned fragment can be used for high level expression of another gene of interest. This is accomplished by introducing the other gene into the plant chromosome, at a position and in an orientation corresponding to that of the heterologous gene. The insertion site for the gene of interest would not necessarily have to be precisely the same as that of the enzyme encoding gene, but simply in near proximity. Integration of an expression vector constructed as described above, into the plant chromosome then would be accomplished via recombination between the cloned plant DNA fragment and the chromosome. Recombinants, where the gene of interest resides on the chromosome in a position corresponding to that of the highly expressed enzyme encoding gene likewise should express the gene at high levels.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

While the examples are directed to particular enzymes, it is evident that any enzyme produced in a plant by introduction of heterologous DNA encoding the enzyme, where that enzyme requires a transitional metal cofactor to be in the active form, is encompassed within the scope of the invention.

The following are presented by way of illustration and are not intended to limit the scope of the invention. The references cited in this specification are incorporated herein by reference.

EXAMPLE 1

Laccase Extraction with Copper—Background Methodology

Lignin is a biopolymer of plants that is a major component of secondary cell walls (Bonner and Varner, 1976). This complex polymer is formed from oxidized phenolics produced through the action of oxidases such as peroxidase or laccase. The use of plant cell wall materials such as wood, wheat straw or corn stover as a source of fiber, fuel or feed requires the removal, degradation or modification of lignin. Currently, processes to remove lignin or disrupt and reform lignin bonds are generally chemical processes and are highly polluting. Improved processes which lower pollution are being sought.

In this regard, enzymes secreted from wood rot fungi can be utilized to modify lignin. Laccases are one class of these enzymes (Call and Mucke, 1997), called blue copper oxidases and use copper to accept and donate electrons in the oxidation and reduction of substrates. The presence and oxidation state of copper in these enzymes is critical to their maximal activity. Laccase activity oxidizes the phenol components of the lignin (Solomon et al., 1996; Yaropolov et al., 1994). This action on a large scale can be applied to many industrial processes. In an effort to produce large amounts of laccases for industrial applications, the plant expression system is utilized and here transgenic Zea mays L. is used as a biofactory. The Trametes versicolor laccase I gene was cloned (Ong et al. 1997) and placed under the control of maize promoter elements to induce high expression. The source of the gene is not critical to achieving laccase expression, and the Stachyboytrys laccase gene as described below was also used in these experiments, where indicated. One of the most important factors in successful expression of this enzyme in active form in maize is the transition metal, copper. Without copper one may successfully express inactive laccase. Copper is important for laccase activation, stable high expression in the plant, and enzyme stability in an extract. The inventors here have discovered that providing additional copper over that already in the plant is important for obtaining laccase in an active form.

Isolation and Cloning of Laccase Encoding DNA

Attempts have been made to introduce laccase-encoding nucleotide sequences into plants for the purpose of changing the lignin content of the plant in WO 98/11205 and WO97/45549. Commercially acceptable levels of laccase production is taught at WO 00/20615.

The gene for laccase was cloned from Trametes versicolor by the methods described here, with isolated RNA reverse transcribed into cDNA. The sequence is set forth at FIGS. 1A–C and can also be found at Ong, E. et al. (1997).

Preparation of Plasmids

Figure 3:
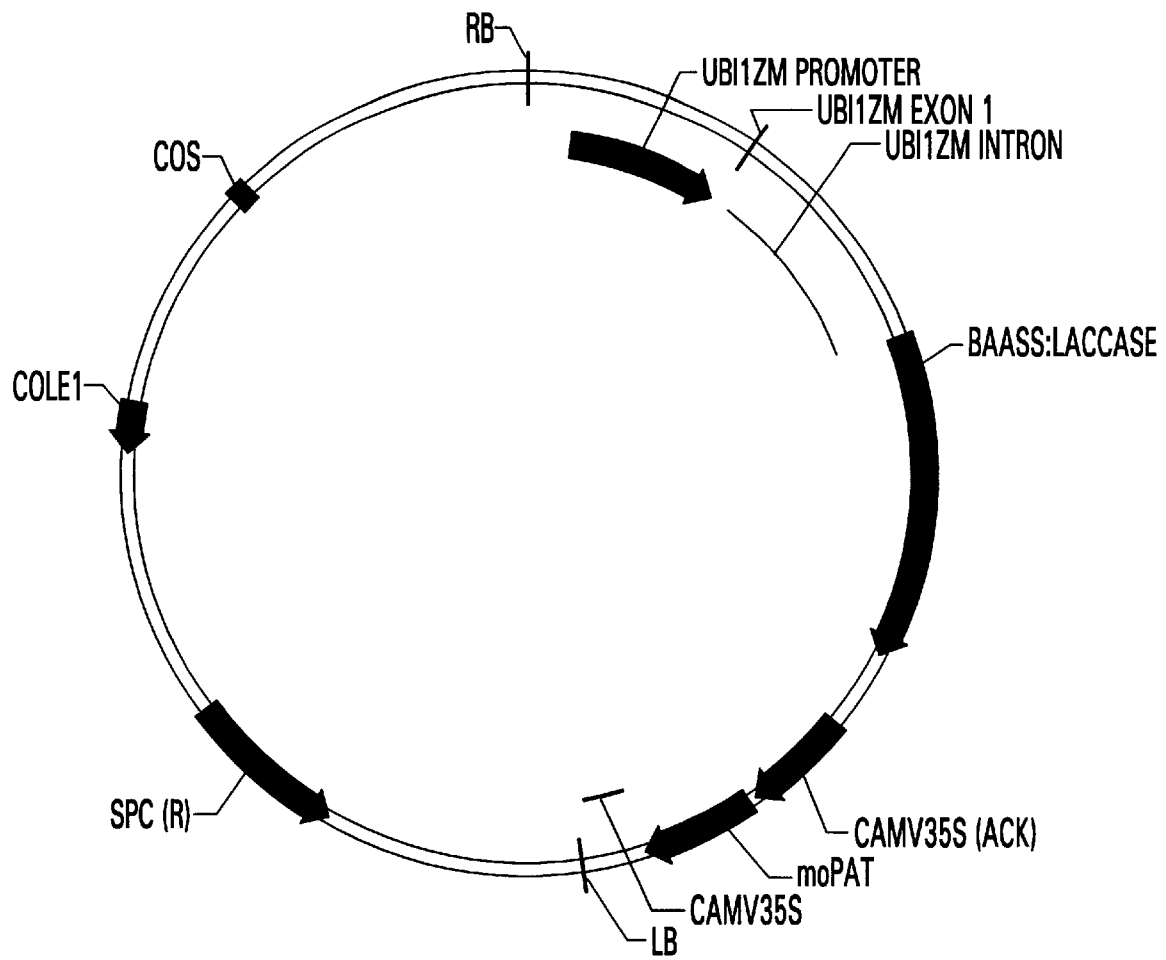
FIG. 3 is p7718, a construct containing the laccase gene driven by the ubiquitin promoter, containing the barley alpha amylase signal sequence and the maize optimized PAT gene as a selectable marker, driven by the 35 S promoter. It further contains left and right borders of the T-DNA sequences.
Figure 4:
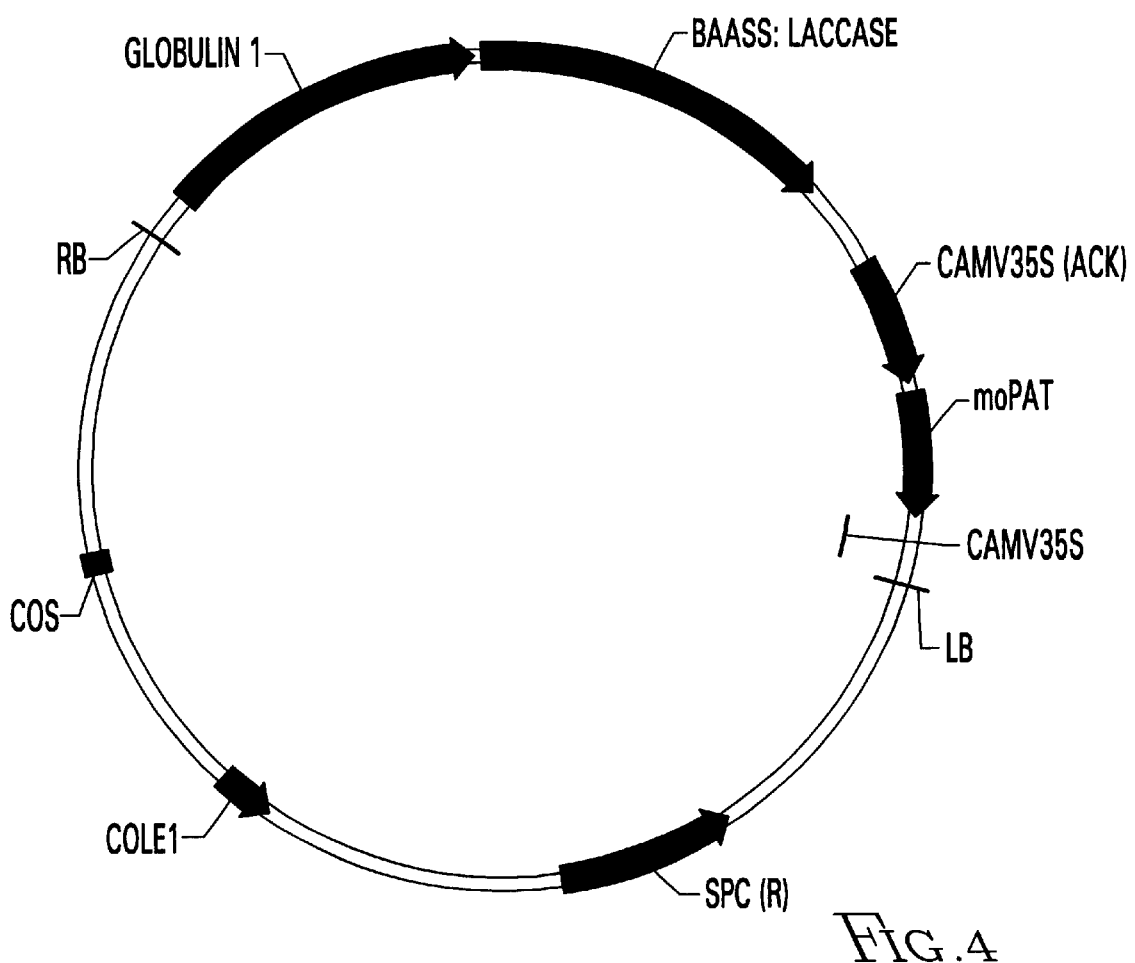
FIG. 4 is p8908, which is the same as 7718, except it substitutes the globulin promoter for the ubiquitin promoter.

FIGS. 2A–D provides a schematic overview of the process used for production of the plasmids. (Note the following abbreviations are used: BAASS refers to the barley alpha amylase signal sequence; FSS refers to fungal signal sequences; KDEL is the sequence targeting expression to the endoplasmic reticulum; ubi refers to a ubiquitin promoter; pinII is the terminator; CaMV refers to the 35S cauliflower mosaic virus; moPAT is the maize optimized pat selectable marker; and OPH refers to the organophosphate hydrolase gene, all of which are described herein.) The plasmids containing the barley alpha amylase signal sequences were produced by ligating oligomeric sequences encoding the sequence to the 5' end of the laccase gene, then the entire sequence amplified by PCR and cloned into a The sequencing of individual clones followed and confirmed the presence of the construct. An individual clone was chosen for further manipulations. To generate plasmid 7718 (FIG. 3) intermediate vectors with BAASS:: laccase were cut with NcoI and HpaI and ligated into vector 2774, which contains the ubiquitin promoter and PinII terminator. Plant ubiquitin promoters are well known in the art, as evidenced by European patent application no. 0 342 926. The entire transcription unit was cut from 2774 with NheI and NotI and ligated to 3770 containing the 35S promoter with the PAT selectable marker between the left and right borders of the Agrobacterium tumefaciens. For plasmid 8908 (FIG. 4) the same procedure was employed, and the ubiquitin promoter of the 2774 vector removed, substituting the globulin promoter. This is the promoter of the maize globulin-1 gene, described by Belanger, F. C. and Kriz, A. L. at "Molecular Basis for Allelic Polymorphism of the Maize Globulin-i gene" Genetics 129:863–972 (1991). It also can be found as accession number L22344 in the Genebank database. The globulin promoter in p3303 was cut with HindIII and NcoI, and vector 2774 having the ubiquitin, barley alpha amylase, laccase and PinII sequences was cut with the same restriction enzymes. The two pieces were then ligated to create plasmid KB254. While there are several approaches possible for preparing the plasmid, in this procedure the HindIII and NarI site from KB254 was used to cut p7718 and substitute the globulin promoter for the ubiquitin promoter in 7718 to create p8908.

Figure 5:
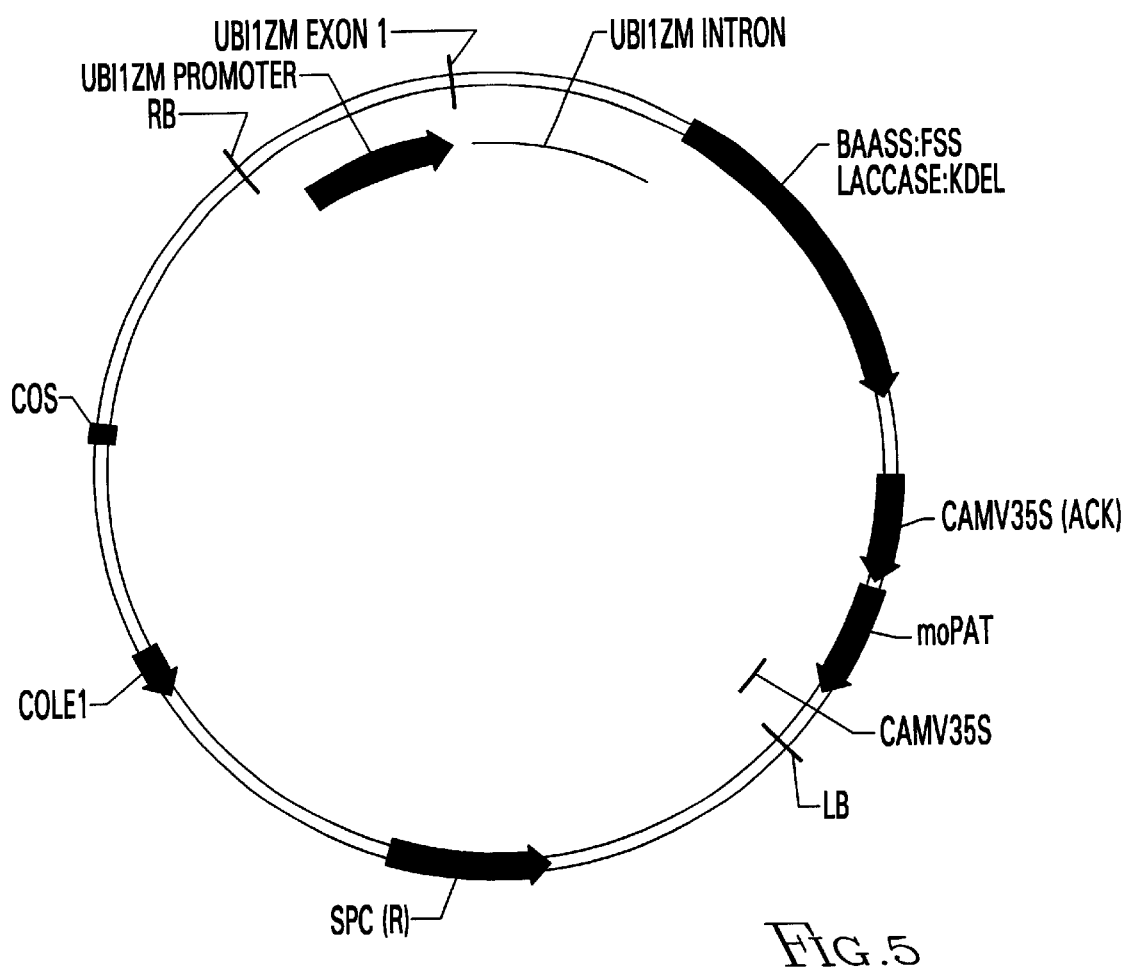
FIG. 5 is p7017, a construct which is essentially the same as p7718, except that it also contains the KDEL sequence and a fungal signal sequence.
Figure 6:
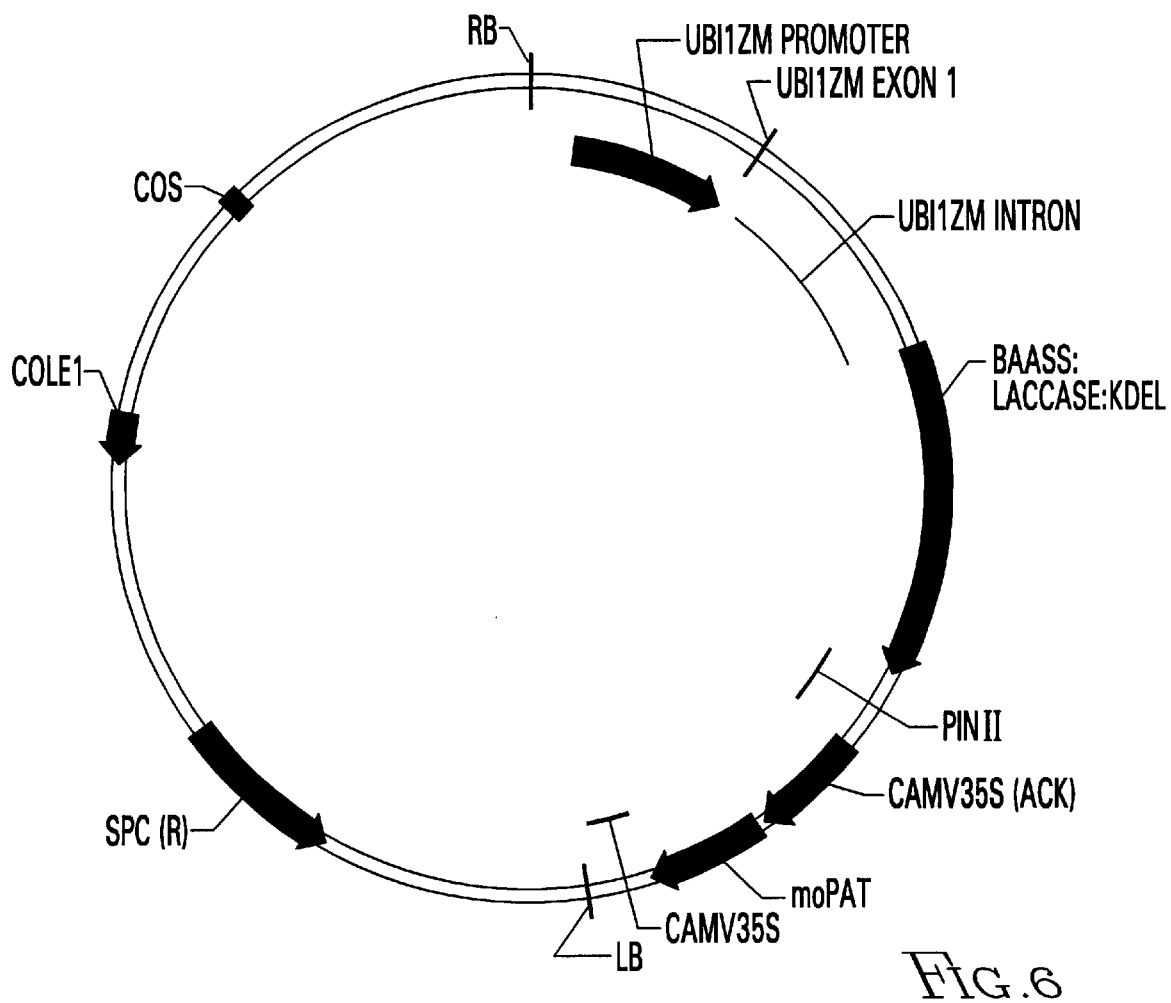
FIG. 6 is p7699, which is essentially the same as p7017, except that the fungal signal sequence is not present.

For plasmids 7017 and 7699, (FIGS. 5 and 6) containing the KDEL sequence, the nucleotides for the amino acids lysine, aspartic acid, glutamic acid and leucine (KDEL) were added to the 3' end of the laccase gene by PCR amplification using a reverse primer containing the KDEL sequence. The entire coding sequence was then put into 2774 containing the ubiquitin promoter and the PinII terminator. Following this it was cut with NheI and NotI and ligated to 3770 as described above, to generate 7017 and 7699.

Transformation of Maize

Fresh immature zygotic embryos were harvested from Hi-II maize kernels at 1–2 mm in length. The general methods of Agrobacterium transformation were used as described by Japan Tobacco, at lshida as modified and described, supra. Fresh embryos were treated with 0.5 ml log phase Agrobacterium strains EHA 101 as described above. Bacteria were grown overnight in a rich medium with kanamycin and spectinomycin to an optical density of 0.5 or greater at 600 nm then re-inoculated in a fresh 10 ml culture. The bacteria were allowed to grow into log phase and were harvested at no more dense than OD600=0.5. The bacterial culture was pelleted and resuspended in a co-culture medium.

Individual transformation events were identified when they grew rapidly on the bialaphos-containing medium (3 mg/L). The events were identified as follows: LCB is an event generated from plasmid 7017; LCC from p7699; and LCG from 8908. Two LCB events, and several LCC and LCG events were selected. Several plants per transformation event were regenerated from embryogenic calli as described (Hood et al., 1997) and allowed to flower and set seed in the greenhouse. T1 (first generation transformed) seed was planted in back-cross nurseries and crossed to elite inbreds to develop high-yielding hybrids with good agronomic qualities. Grain for processing is produced from these lines.

Extraction of Corn Seed

Five $T_1$ seeds were pulverized individually and homogenized with either 20 mM sodium acetate, pH 5.0 (SA), or 20 mM sodium acetate, pH 5.0 containing 0.05% Tween-20 (SAT) for enzyme assay analysis For pooled seed samples, 50 seeds were ground together in a coffee grinder and separate aliquots were extracted as for individual samples. Extraction was routinely performed with a 1:2–1:5 ratio of seed tissue to buffer. Extracts were centrifuged for 10 minutes at 20,000× g to pellet cell debris and the supernatant was placed in a fresh tube. Timing and amount of $CuSO_4$ addition are noted for each individual experiment. Protein precipitated by the copper treatments was pelleted by centrifugation for 10 minutes at 20,000× g and the supernatant was transferred to a fresh tube.

Determination of Total Soluble Protein.

Total soluble protein in each extract was determined using the microtiter assay conditions and reagents from Bio-Rad. With this method, total protein was determined by the Bradford method (Bradford, 1976) using the microassay protocol from Bio-Rad (Hercules, Calif.). Basically, a standard curve of known concentrations of bovine serum albumin (Sigma P7656) were prepared in extraction buffer. Ten microliters of standard or sample are pipetted in duplicate into 96-well polystyrene plates and 200 µl of diluted protein assay dye reagent is added to each sample. The plate was then read at 595 nm and the protein concentrations of the unknowns are calculated by comparison to the standard curve. Samples were quantitated by comparison to a standard curve of bovine serum albumin (Sigma Chemical Co., St. Louis, Mo.) from 0.5–6 µg. Laccase microtiter plate activity assay One to ten µg of soluble corn protein was added per well of a 96-well polystyrene microtiter plate (Costar) containing 140 µl 20 mM sodium acetate pH 5.0 containing 0.05% Tween-20 in each well. The reactions were initiated with 20 µl of 4.5 mM ABTS substrate (Putter, J., and Becker, R., 1981) and the microtiter plate was incubated at 25° C. The plates were read at 420 nm on a Spectromax 340 (Molecular Devices) at several times, usually one hour and 18–22 hours total duration depending on the concentration of laccase in the sample. Laccase activity was determined by comparison with known amounts of purified recombinant Trametes laccase from Aspergillis (See Table 4).

Western Analysis

A Western analysis is a variation of the Southern analysis technique. With a Southern analysis, DNA is cut with restriction endonucleases and fractionated on an agarose gel to separate the DNA by molecular weight and then transferring to nylon membranes. It is then hybridized with the probe fragment which was radioactively labeled with $^{32}P$ and washed in an SDS solution. In the Western analysis, instead of isolating DNA, the protein of interest is extracted and placed on an acrylamide gel. The protein is then blotted onto a membrane and contacted with a labeling substance. See e.g., Hood et al, "Commercial Production of Avidin from Transgenic Maize; Characterization of Transformants, Production, Processing, Extraction and Purification" Molecular Breeding 3:291–306 (1997).

Laccase samples were analyzed by Western blot. Briefly, proteins were separated on 4–20% acrylamide gels (Novex) under reducing, denaturing conditions and transferred to Immobilon P PVDF (Millipore). Immunoblots were then blocked with 5% nonfat dried milk in Tris buffered saline with 0.05% Tween-20 (TBST), followed by incubation with anti-laccase polyclonal antibodies produced in rabbit. The blots were then probed with anti-rabbit peroxidase conjugate (Roche Boehringer Mannheim) and specific cross-reaction was detected with the enhanced chemiluminescent kit from Amersham. (See FIG. 7).

Biochemical Characterization of Maize-Derived Laccase.

Expression of laccase was monitored for all events and plants that produced seed. Five seeds per plant were individually analyzed for laccase content. Laccase protein was extracted with other cellular proteins soluble in 20 mM sodium acetate, pH 5.0 with 0.05% Tween-20 (SAT). After determination of total soluble protein (TSP), the extracts were analyzed by the laccase activity assay in a 96 well microtiter plate, using ABTS as the substrate (Putter and Becker, 1981). Laccase amounts were determined by comparison with a known amount of Trametes-derived standard and expressed as a percent of the protein (Table 4). After extraction in either buffer, some extracts were also analyzed by Western blot and compared to Trametes-derived standards.

The amount of active laccase in transgenic $T_1$ seed varied by vector and by the events and lines produced from each vector (Table 4). Individual T1 seed were screened for laccase expression by enzyme assay on non-copper treated extracts (Top half of Table 4). Some extracts were re-screened with copper-treatment (Bottom half of Table 4). The LCB events recovered from the vector that contained two signal sequences (native fungal and BAASS) and the ER retention signal (KDEL) produced a high-expressing seed per line that contained active laccase at 0.065 %TSP. The first lines of LCC that were produced (also ER targeted) without added copper in tissue culture (see below), expressed active laccase at 0.02% TSP in the high seed per line. The LCG events recovered from a vector in which the laccase gene is driven by the maize globulin-1 promoter produced lines that were the highest expressing in this experiment. The laccase was targeted to the cell wall, and the high seed was 0.24% TSP active laccase. (Table 4).

Figure 7:
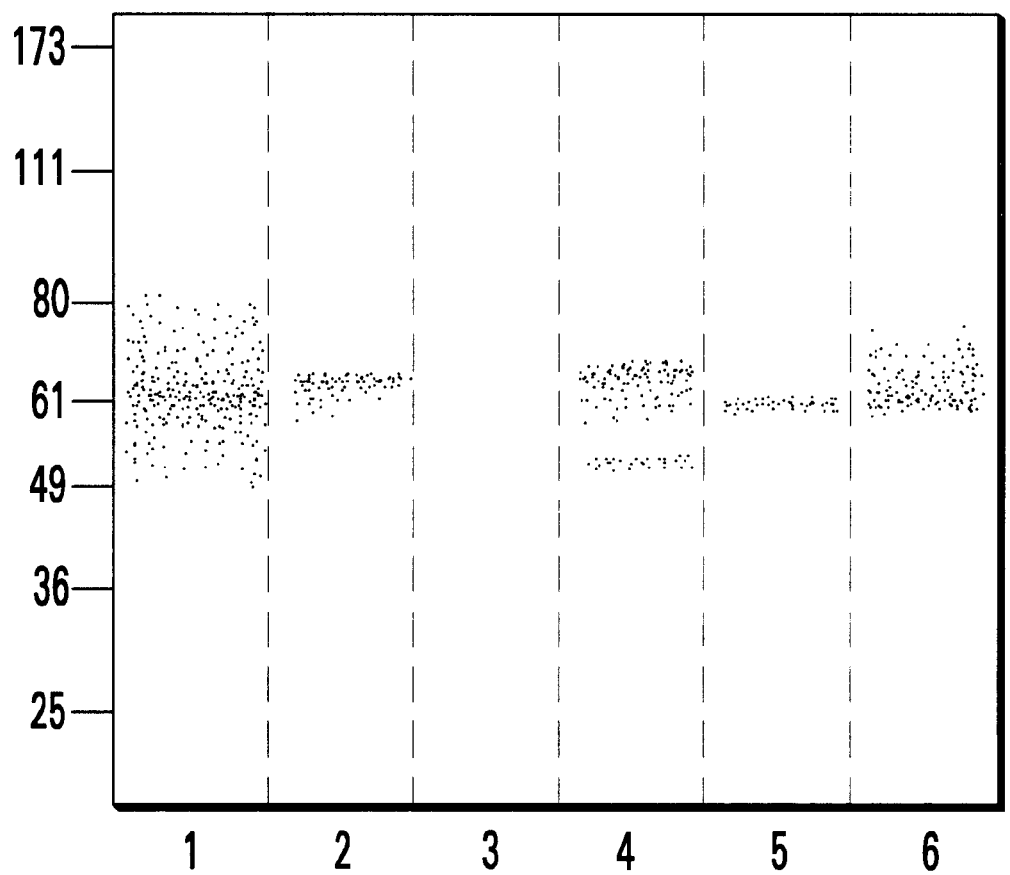
FIG. 7 shows a Western blot of seed extracts from various plant lines. Positive controls are 10 and 1 ng of laccase purified from *Trametes versicolor* produced recombinantly in Aspergillus fermentation broth (lanes 1 & 2). Lanes contain: control corn seed extract as negative control, and seed extracts from an LCB line, an LCC line and an LCG line. Each lane was loaded with ~20 µg total protein except for LCG which was loaded at ~0.5 µg total protein. Molecular weight markers are shown on the left.

Seed extracts from several $T_2$ lines of LCB, LCC and LCG were analyzed qualitatively and semi-quantitatively by Western blot (FIG. 7) as well as activity assay. Note the Western detects total laccase, whether active or not where the enzyme activity assay detects the level of active laccase. The blots were developed with antibodies raised in rabbits whose sera were pre-screened for low levels of cross-reactivity with corn seed proteins (Hood et al, 1997). The $T_2$ seed extracts contained two bands that were similar in molecular weight (approximately 62 and 65 kDa) to the two major bands visualized in the Trametes control (FIG. 7). The intensity of the bands reflects approximately the amount of laccase loaded. For $T_2$ seed the amounts of laccase detected in the original extracts by activity assay did not correlate with the amount of laccase estimated from the Western blots, sometimes by as much as 50 fold (Table 4). Extracts were brought to a final concentration of 10 mM $CuSO_4$ by adding the appropriate volume of 1M $CuSO_4$ stock prepared in distilled water. Extracts were then mixed and incubated at 50° C. for one hour. The addition of $CuSO_4$ causes protein to pecipitate (Bell et al., 1983) while leaving laccase in solution and this precipitate was removed by centrifugation at 10,000× g for ten minutes before analysis by activity assay.

TABLE 4

| Construct | Event #'s | $T_1$, highest single seed | | $T_2$, pooled seed | |
|---|---|---|---|---|---|
| | | Enzyme Assay | Western | Enzyme Assay | Western |
| No Copper Treatment, Laccase as % TSP | | | | | |
| LCB | 1&2 | 0.065 | 0.06 | 0.002 | 0.1 |
| LCC | 1–8 | 0.021 | NA | 0.002 | NA |
| | 9–24 | 0.0044 | NA | 0.0021 | 0.01 |
| LCG | 1&3 | 0.16 | 0.2 | 0.1 | 3 |
| | 5–13 | 0.24 | NA | NA | NA |
| Treated with 10 mM CuSO4, 1 h @ 50° C., Laccase as % TSP | | | | | |
| LCB | 1&2 | NA | 0.06 | 0.14 | 0.1 |
| LCC | 1–8 | NA | NA | 0.015 | NA |

TABLE 4-continued

| | Event | $T_1$, highest single seed | | $T_2$, pooled seed | |
|---|---|---|---|---|---|
| Construct | #'s | Enzyme Assay | Western | Enzyme Assay | Western |
| | 9–24 | 0.067 | NA | 0.029 | 0.01 |
| LCG | 1&3 | 0.8 | 0.2 | 1.1 | 3 |
| | 5–13 | 0.68 | NA | 1.4 | NA |

NA = not analyzed

After treatment with 10 mM $CuSO_4$ for one hour at 50° C., the amount of active laccase detected by activity assay increased 3–10 fold as compared to the untreated samples (see Table 4). This was the case not only for $T_1$ seed from many different events and constructs, but for subsequent generations of seed produced in the field as well. The amount of laccase detected by enzyme assay after treatment with copper sulfate correlates much more closely with the amount determined by Western analysis (see $T_2$ data above). Due to protein precipitation, the actual amount of laccase recovered as a perecent of the soluble protein left after precipitation can increase as much as ten fold, achieving anywhere from 10% to 90% enrichment of laccase depending upon the conditions of the copper treatment. This results in laccase activity levels that are 110-fold higher in the copper treated extract. Therefore, the assay figures in Table 4 use the protein concentration for an untreated sample, and show the amount of active laccase after copper treatment, allowing comparison of the percent total soluble protein numbers in the upper and lower parts of the table. Samples on Western blots are not affected by copper treatment and the concentrations predicted are a rough estimate.

In some events, particularly LCC events, expression level in callus and leaf tissue was also monitored. This was primarily done because the first attempts to produce plants from transgenic events from this vector were not successful. Though events were recovered at a low frequency, as soon as plants were regenerated and placed in the light, the growing point (meristem) died. Consequently, the only event that survived to produce seed was an event that showed quite low expression of active laccase in seed (0.02% TSP). One possibility for this failure could be that the presence of laccase in the transgenic events had detrimental effects. Alternatively, the laccase could more simply be using up all available copper, and other essential copper-requiring enzymes in the cell were not able to incorporate copper, possibly making them inactive. To test the latter hypothesis, 0.025 mg/L copper salt was added to the callus selection medium and 23 healthy events were recovered (data not shown). In assays of the callus material, high levels of laccase activity were detected in these events selected on copper.

EXAMPLE 2

Laccase Recovery from Field Samples

Rows of plants derived from single ears of $T_1$ seed generated in the greenhouse were planted in nurseries for back-crossing to elite inbreds. For the first few lines of LCB, the first generation in the field ($T_2$ seed) yielded very low amounts of active laccase when extracted with SAT and analyzed in the enzyme assay without copper treatment (Table 5, $T_2$ seed pools). To examine whether yields could be improved by external application of copper, the field was sprayed at pollen shed and again two weeks later with Keyplex micronutrients (a liquid fertilizer) containing approximately 0.006% w/v copper ion. The seed harvested from that field yielded a restored active laccase amount, 0.01% TSP (SAT extraction, no copper treatment in vitro), more similar to the $T_1$ generation seed (Table 5, see $T_3$ seed).

TABLE 5

| Copper exposure | $T_1$ (high seed) | $T_2$ averaged single seed analysis | $T_3$ pooled seed analysis |
|---|---|---|---|
| Not activated | 0.06 | 0.002 | 0.0025 |
| Not activated, copper sprayed | NA | NA | 0.01 |
| Activated | NA | 0.035 | NA |
| Activated, copper sprayed | NA | NA | 0.024 |

Provision of exogenous foliar copper ions allowed the incorporation of copper ions into the laccase protein enabling approximately 10 times greater levels to be recovered than those in grain from the field without added micronutrients or copper. This field material showed activation also with copper in vitro, suggesting that the affect of copper need not coincide wholly with developmental accumulation of the apoprotein. Copper ions are not usually limiting in normal plant development but uptake can be limited on farmlands with high soil organic content and pH. Therefore, application of chelated copper, a commonly used additive in grain production, to the production fields to induce consistent accumulation of laccase in grain is feasible.

By the process outlined in the above examples, it is possible to achieve a 5–150 fold improvement over initial SAT extracts in the amount of active laccase detected as a percent of total soluble protein from flour of transgenic seed. These results have implications for the detection of transgenic protein, its production process and recovery of the product. Increased amounts of active laccase are recovered whether copper is added to the extraction buffer (see Example 3) or after the enzyme has been extracted. Because the amount of copper remaining in the pellet is large when copper is included in the extraction buffer, adding copper to the extract rather than using it to extract the corn flour is a potentially preferred process, allowing minimal residual copper in the flour.

EXAMPLE 3

Copper in Laccase Recovery

The following experiments included copper in the extraction buffer, after extraction and with variable temperatures. Extraction of corn seed, determination of soluble protein and laccase microtiter assay were performed as in Example 1. In addition to SAT (sodium acetate tween), buffers with variations in salt concentration, detergents and reducing agents were used (Table 6). Each sample was extracted twice with the same buffer and the extracts combined. The buffer containing copper sulfate (10 mM, #7) had the greatest affect on recovery of active laccase and reduced the amount of total soluble protein (of all protein) recovered in this experiment by 4.3 fold. This latter result is partially due to protein precipitation by the copper (Bell et al, 1983). Additionally, 1.6 times more active laccase was recovered in the two extractions in the copper-containing buffer compared to SAT without copper on a dry weight basis. The result was a solution containing 6.5 times more active laccase as a percent of the soluble protein compared to an SAT extract (Table 6). It was found that copper sulfate selectively precipitated protein from the extract. Surprisingly, laccase was found in the supernatant. Thus, in addition to increasing the yield of active laccase from transgenic seed, incubation of the seed extract in copper sulfate containing buffer served to mostly purify that active laccase.

TABLE 6

Extraction of laccase in 8 buffers from LCB pooled seed. Values were determined by enzyme assay.

| Buffer | ng lcc/mg seed in 2 extracts | mg protein/ mg seed in 2 exts | LCC % TSP in 2 exts |
|---|---|---|---|
| #1 20 mM sodium acetate, 0.05% Tween-20 pH 5 | 0.56 | 5.2 | 0.011 |
| #2 50 mM sodium phosphate, 0.1% sodium lauryl sarcosine, 0.1% Triton X100-pH 7 | 0.67 | 5.0 | 0.013 |
| #3 #2 plus β-Mercaptoethanol- pH 7 | Interference | 4.7 | X |
| #4 #1 plus 6.5 mM CHAPS- pH 5 | 0.59 | 5.4 | 0.011 |
| #5 #1 plus 250 mM ascorbic acid-pH 5 | Interference | 4.4 | X |
| #6 #1 plus protease inhibitor cocktail-pH 5 | 0.64 | 6.1 | 0.010 |
| #7 #1 plus 10 mM $CuSO_4$-pH 5 | 0.88 | 1.22 | 0.072 |
| #8 100 mM MES plus 0.05% Tween-20-pH 7 | 0.58 | 3.7 | 0.016 |

CHAPS = (3-[(3-Cholamidopropyl)dimeylammonio]-1-propane-sulfonate, MES = (2-[N-Morpholino]ethanesulfonic acid)

Figure 8:
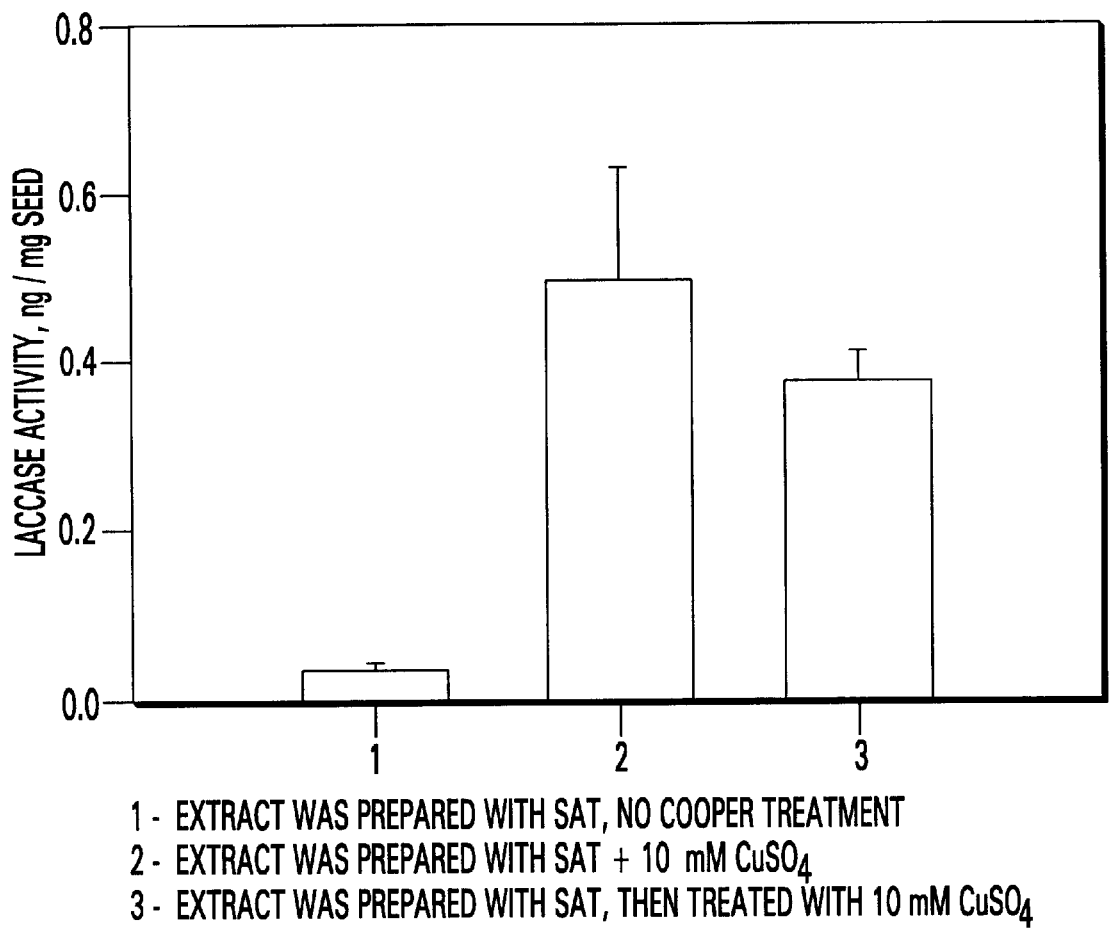
FIG. 8 shows a graph depicting results of timing of copper addition to extracts of maize flour. Flour was extracted either with SAT alone, or SAT +10 mM copper sulfate. The SAT extract was divided and either assayed directly, or treated with 10 mM copper sulfate then assayed. Precipitated proteins were removed from the copper sulfate treated extract. The amount of active laccase protein was determined by enzyme assay.

To explore whether copper action resulted in the recovery of more active laccase or simply improved extraction, LCB flour was extracted with SAT or SAT plus copper sulfate (10 mM). The SAT extract was brought to a final concentration of 10 mM copper sulfate subsequent to extraction, and precipitated proteins were pelleted. Laccase enzyme assays were performed on each extract (FIG. 8). Similarly high levels of laccase were recovered whether the $CuSO_4$ was added to the extraction buffer or to the extracted protein, indicating that the $CuSO_4$ affects active laccase recovery and does not improve extraction.

Figure 9:
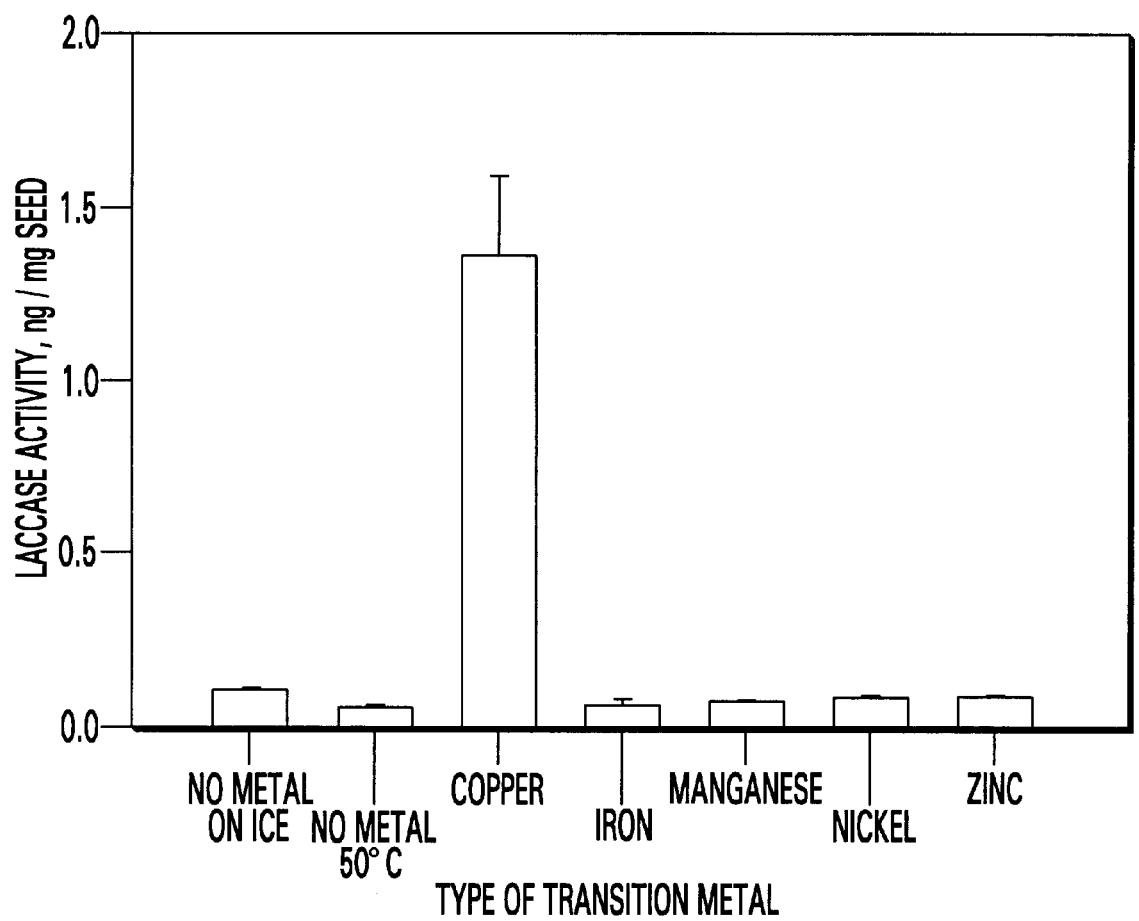
FIG. 9 shows a graph depicting results of transition metal activation of laccase. Total proteins were extracted from LCB flour with SAT and brought to 10 mM of the salt of each transition metal as indicated. Proteins were incubated at 50° C. for 1 hour, centrifuged and laccase activity determined by enzyme assay.

Substitution for copper with other transition metals was tested (FIG. 9). Three separate extracts of LCB flour were prepared in SAT for each experimental metal. Each sample was brought to a final concentration of 10 mM of the following salts: $CuSO_4$, $FeSO_4$, $MnSO_4$, $NiSO_4$, and $ZnSO_4$. The extracts were then incubated at 50° C. for one hour, centrifuged at 10,000× g for 10 minutes and the supernatants analyzed for total protein and laccase activity. Shown are the averages and standard deviations for the three extracts. SAT extracts either heated for one hour at 50° C. or not heated were also analyzed as controls. The results show copper allows for the recovery of more active laccase.

Figure 10:
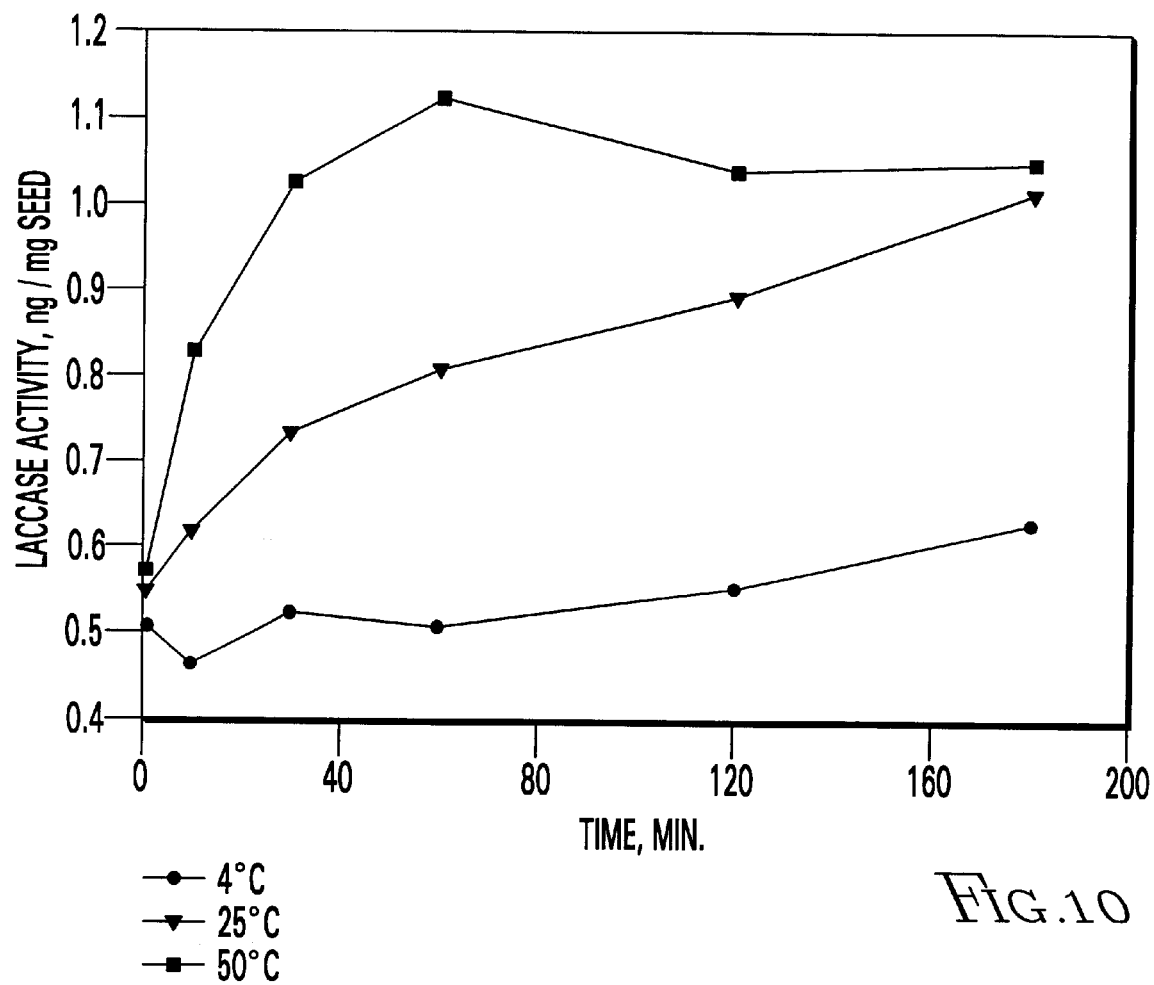
FIG. 10 shows a graph depicting results of copper sulfate activation of laccase at three temperatures over time. An SAT extract of LCB flour was divided into three fractions, 10 mM copper sulfate added and the extracts incubated at the indicated temperatures. Samples were assayed in the activity assay over the course of three hours.

The time and temperature of the $CuSO_4$ incubation period impacts recovery of active laccase from LCB seed. LCB corn flour was extracted with SAT and separated into three aliquots. Each aliquot was brought to 10 mM $CuSO_4$ and incubated at either 4° C., room temperature (about 20° to 27° C.), or 50° C. Each aliquot was sampled at 0, 10, 30, 60, 120, and 180 minutes, precipitated proteins were removed by centrifugation and the laccase activity was determined by enzyme assay. Maximal laccase activity was obtained by incubating at 50° C. for one hour or room temperature for three hours (FIG. 10). These conditions appear to be specific to LCB seed either due to the low expression, or perhaps due to the combination of the KDEL ER targeting sequence and the fungal signal sequence, as set forth more fully in Example 4 below.

EXAMPLE 4

Salt Optimization; Incubation with Chloride Salts

Figure 11:
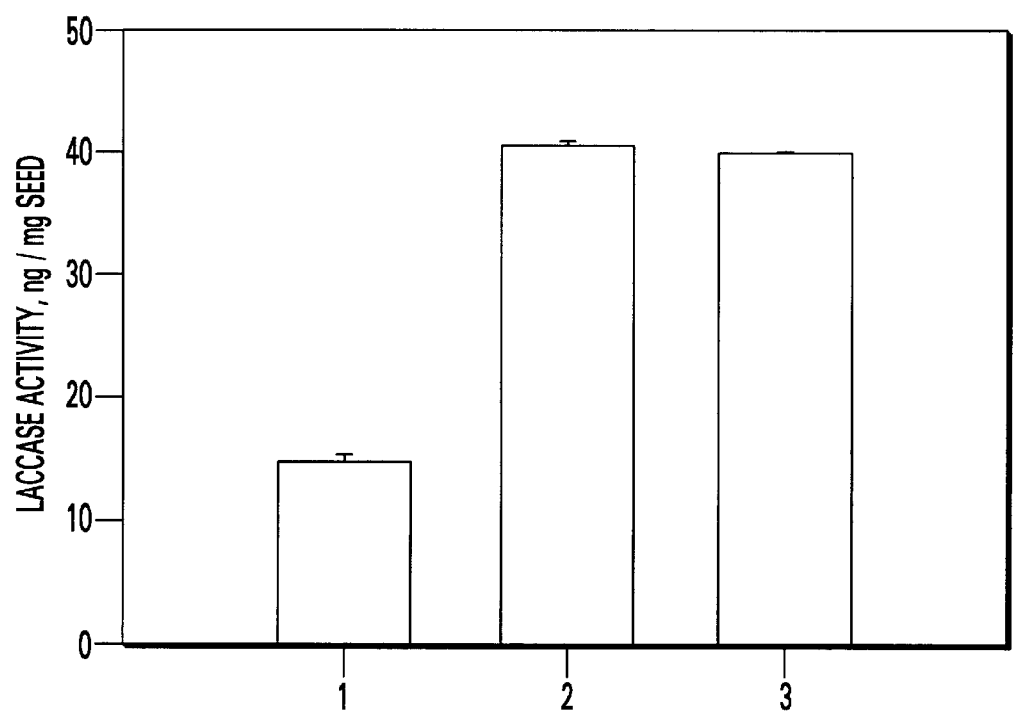
FIG. 11 shows a graph depicting results of using chloride ions to assist in the recovery of active laccase. 0.5 M Sodium Chloride was added to either the SAT extraction buffer or to the laccase extract after extraction along with 10 mM $CuSO_4$. Proteins were incubated for 1 hour at room temperature, centrifuged and laccase activity determined by enzyme assay.

Chloride is a known inhibitor of laccase activity (Yaropolov et al. 1994). When chloride salts are included in the copper treatment step, they can be added separately from the copper sulfate, or used as the copper salt. In these experiments, the process above was repeated, this time using sodium chloride in addition to the copper sulfate. LCG instead of LCB seed was used. LCG contains higher laccase expression levels (~10–50 ng/mg seed active laccase after copper treatment). Unless otherwise noted, corn meal was extracted in 20 mM sodium acetate, pH 5 (SA) for one hour at room temperature. Extraction, copper treatments and enzyme assays were performed according to the method outlined in Example 1. Samples containing chloride salts were diluted to less than 50 mM (Cl⁻) or dialyzed before analysis of enzyme activity (T. Pohl, 1994). For results shown here, samples were diluted about 15 fold into the assay, resulting in a final chloride concentration of 50 mM or less in the activity assay. Copper treatment conditions are noted below. When only copper sulfate is used, 14.9 ng/mg active laccase was recovered (FIG. 11). When 0.5 M sodium chloride (final concentration) is added to the extraction buffer, the amount of laccase recovered with treatment using 10 mM copper sulfate (final concentration) increased to 40.8 ng/mg. When the sodium chloride is added to the copper sulfate treatment step, 40.3 ng/mg laccase is recovered which is almost identical to the amount of laccase obtained when sodium chloride is used in the extraction buffer. (FIG. 11) This indicates that the sodium chloride is enhancing the process by which $CuSO_4$ restores the laccase activity, not improving the extraction of more laccase from the seed.

Figure 12:
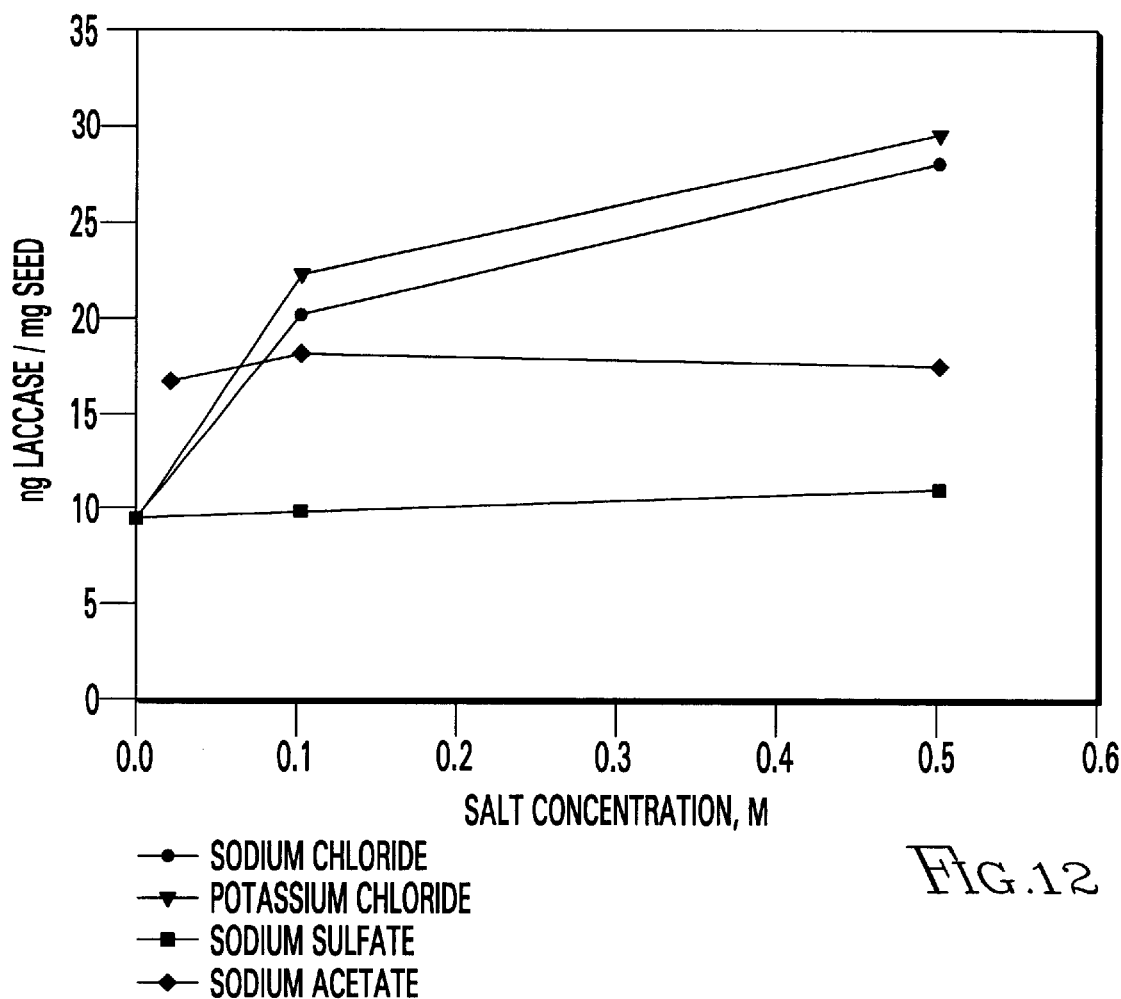
FIG. 12 shows a graph depicting results of LCG seed extracted with 20 mM sodium acetate, 0.1 M sodium acetate or 0.5 M sodium acetate and incubated with 10 mM $CuSO_4$. The sample extracted in 20 mM sodium acetate was incubated with 10 mM $CuSO_4$ and 0, 0.1 or 0.5 M of various salts for one hour at room temperature.

Addition of copper sulfate alone was compared to addition of 10 mM CuS04 (final concentration) with sodium chloride, potassium chloride, sodium sulfate, or sodium acetate (FIG. 12). The presence of the chloride ion is strongly associated with considerable increases in active laccase recovered. Thus, chloride was found to be an optimal negative ion that can be added in the incubation with copper. The chloride salt can be present either during extraction or added after the extract is prepared along with the copper sulfate.

Figure 13:
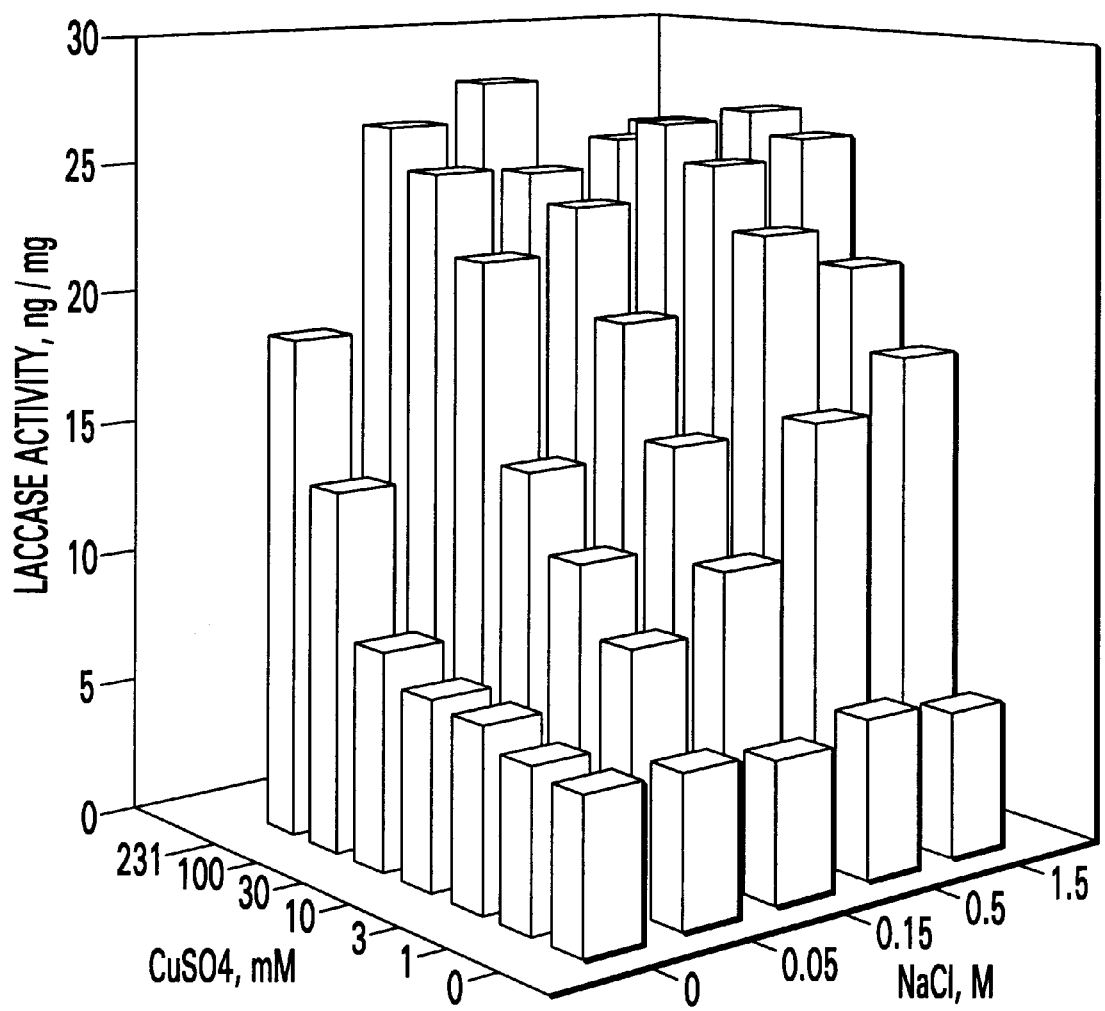
FIG. 13 shows a graph depicting results of LCG flour extracted in sodium acetate (SA) and incubated with various concentrations of sodium chloride and copper sulfate for 30 minutes at room temperature.
Figure 14:
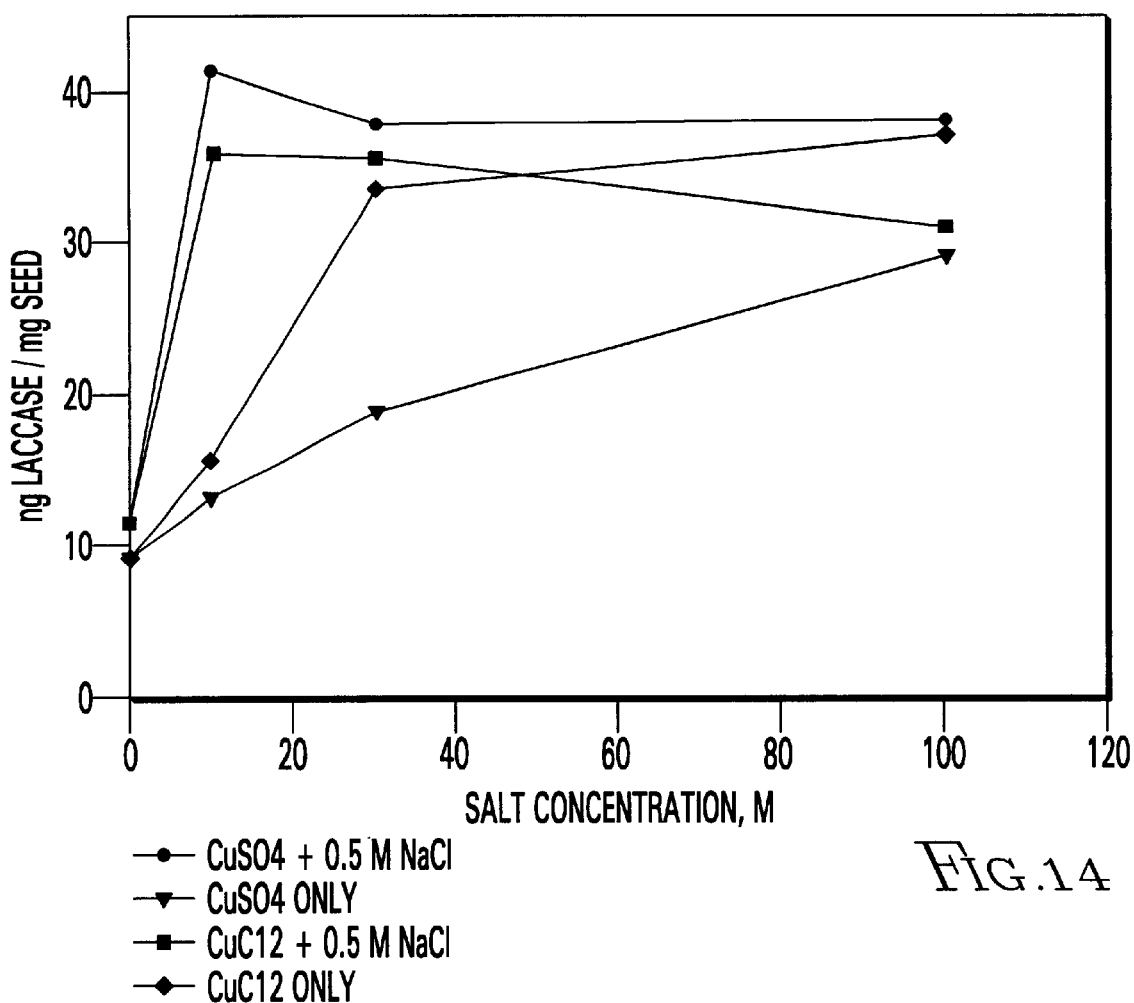
FIG. 14 shows a graph depicting results of comparison of use of chloride versus sulfate salts. LCG flour was extracted in sodium acetate and incubated with and without 0.5 M sodium chloride and with either no copper or up to 100 mM copper sulfate or no cupric chloride up to 100 mM cupric chloride for one hour at room temperature.

Optimal sodium chloride salt concentrations are shown to be between about 0.2M to 1.5M (final concentration) (FIG. 13). At levels above 1.5M, there does not appear to be any additional benefit, although no detriment to the process is apparent. Copper concentrations of 10–100 mM are optimal for this LCG seed as long as sodium chloride is included in the copper treatment step. Further, cupric chloride salt can also be used in place of copper sulfate and sodium chloride. (See FIG. 14.) One skilled in the art may want to vary the amount of chloride added to match the production conditions that are most economically beneficial. Thus, if less chloride is desired, the temperature may be increased or time of incubation extended.

Figure 15A:
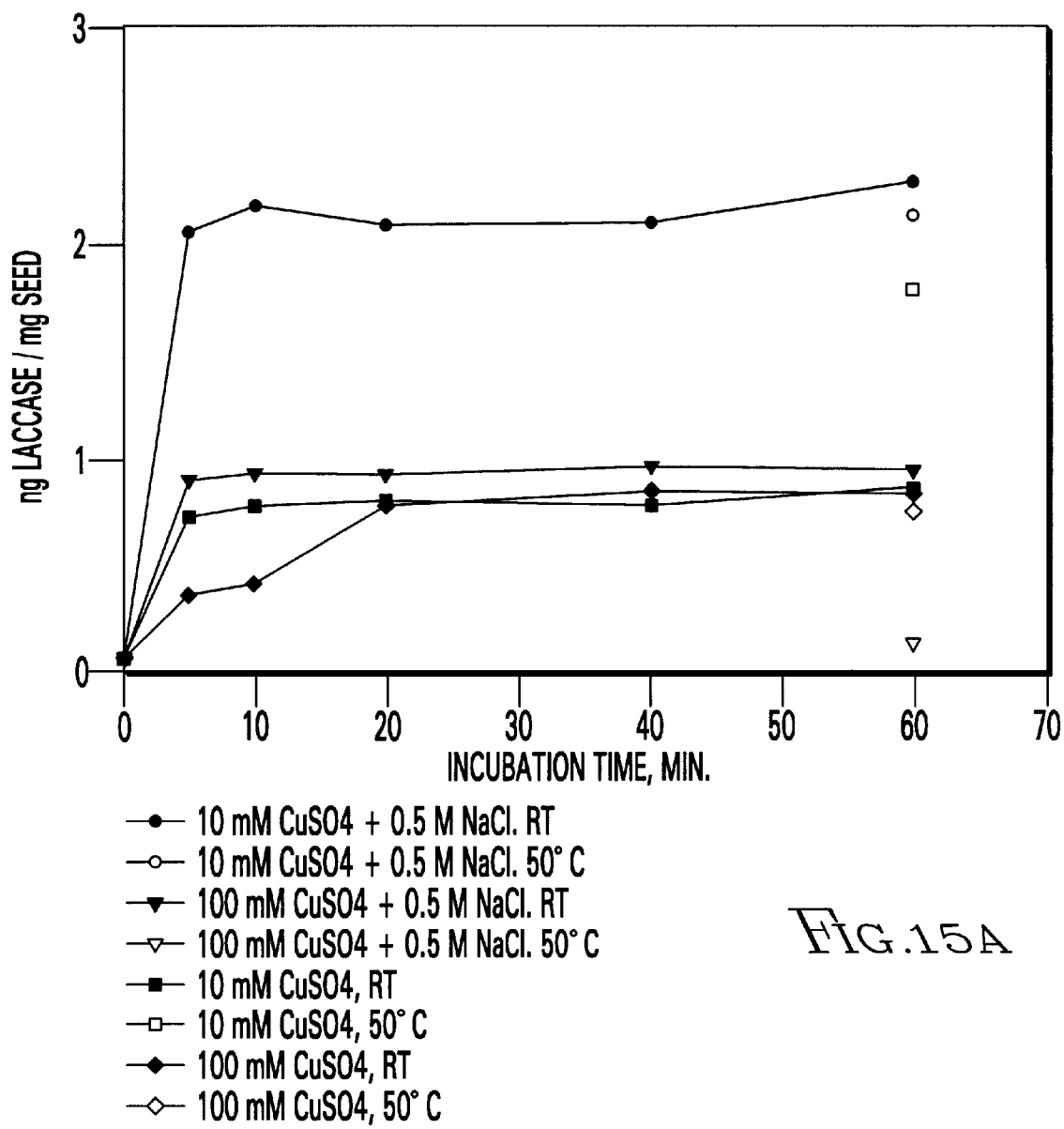
FIGS. 15A and B shows two graphs.
Figure 17A:
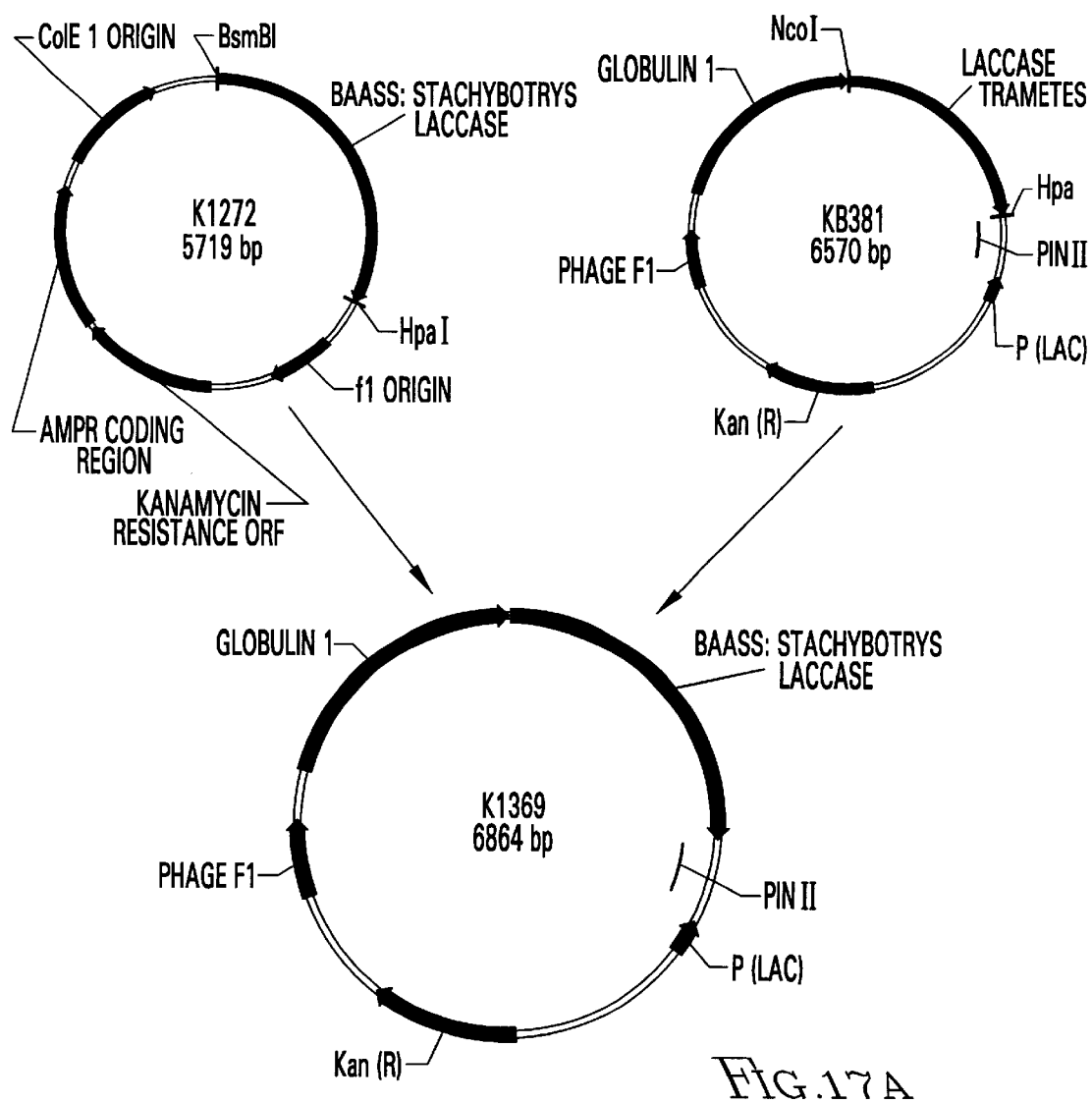
FIGS. 17A and B is a schematic representation of the process used to generate plasmid 8971.
Figure 17B:
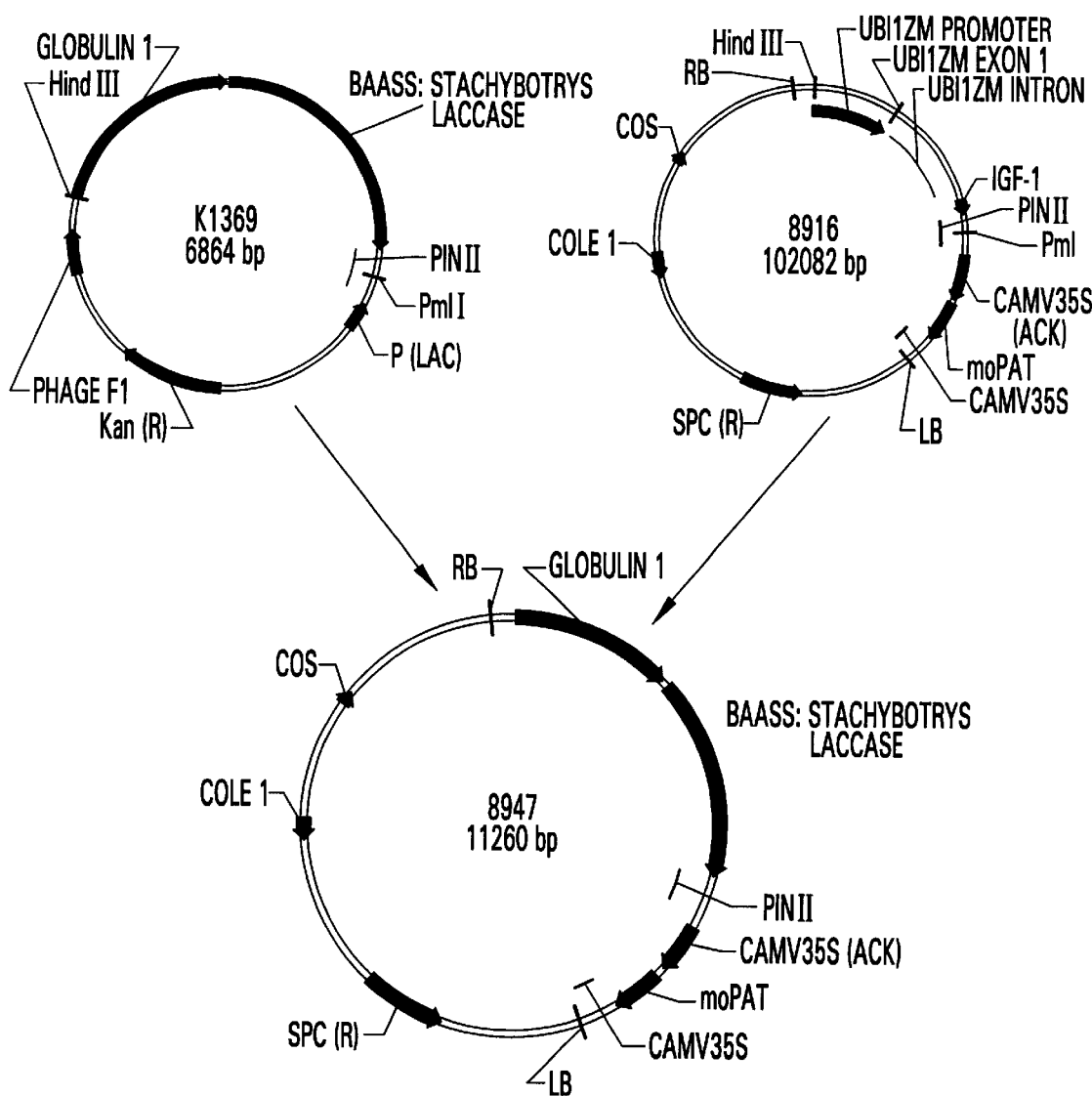
Figure 18:
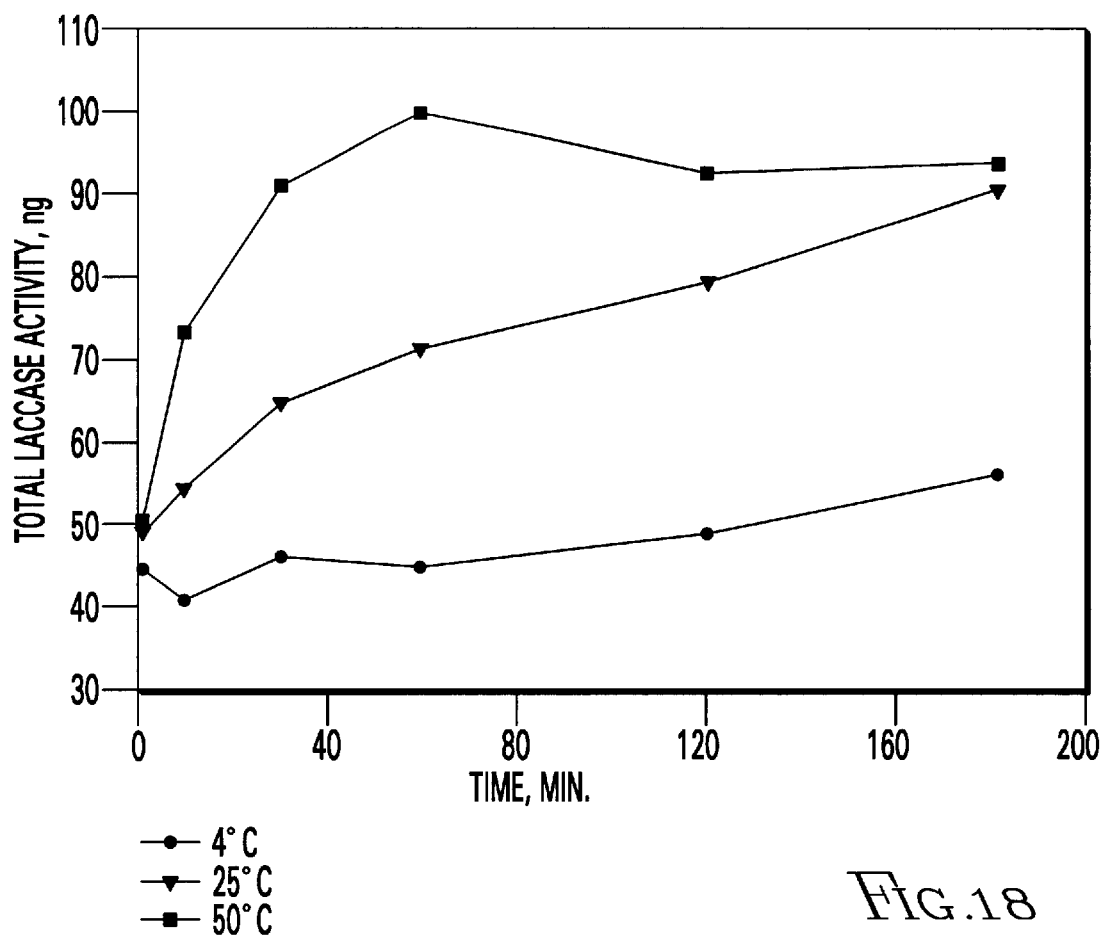
FIG. 18 shows a graph depicting results of LSC seed extracted in SA and copper treated with 10 mM CuSO4 at either 50° C. or ~25° C. Aliquots were removed at 0, 5, 10, 15, 30, 60 and 120 minutes and centrifuged to remove the precipitate. Samples were analyzed by enzyme assay and compared to a standard curve purified Stachybotrys laccase.

As noted above, it is believed that when the negative salt ion is added to the metal solution, it allows more metal to associate with the enzyme. At the same time, the additional salt appears to make the enzyme somewhat more susceptible to degradation when exposed to higher temperatures Thus, temperature at about 25° to 37° C. is optimum, with room temperature of about 25° C. to 27° C. the most optimal for at onset up to 60 minutes. Active laccase recovery with and without salt with varying copper concentrations, at room temperature and at 50° C. is shown in FIGS. 15A and B.

LCB corn extract (FIG. 15A) prepared as in previous experiments, is incubated at room temperature with either 10 or 100 mM copper sulfate over time, with or without 0.5 M sodium chloride. Small aliquots were removed at each time point and centrifuged to remove the precipitated proteins (closed symbols and lines). In addition, an aliquot of extract was also incubated at 50° C. for one hour with either 10 or 100 mM copper sulfate and either with or without sodium chloride (open symbols). An identical experiment using LCG corn extract was performed (FIG. 15B). The addition of sodium chloride allows for considerable increases in recovery of active laccase. Further, when incubated at 50° C., there is a drop in recovery in the results where 100 mM $CuSO_4$ and 0.5 M sodium chloride was used. Thus, the addition of sodium chloride further enhances active laccase recovery, but should be conducted at lower temperatures, most preferably room temperature up to 37° C. Note that the apparent maximal amount of laccase (~2 ng/mg) was detected for LCB with either 10 mM $CuSO_4$ and 0.5 M NaCl (circles) or 10 mM $CuSO_4$ without 0.5 M NaCl at 50° C. (open square). In contrast, 100 mM $CuSO_4$ with 0.5 M NaCl, RT gave the apparent maximal amount of laccase (~5 ng/mg) for the LCG extracts, but incubation of 100 mM $CuSO_4$ without 0.5 M NaCl at 50° C. was actually detrimental to the recovery of active laccase. Therefore, it appears that either the presence of chloride ion or higher temperatures in the copper treatment step are sufficient to allow for the recovery of laccase from LCB seed, but high temperature in the copper activation step is not sufficient to allow for maximal laccase recovery from LCG seed.

EXAMPLE 5

Improving Stachybotrys Laccase Recovery
Background, Vector Construction

Figure 19:
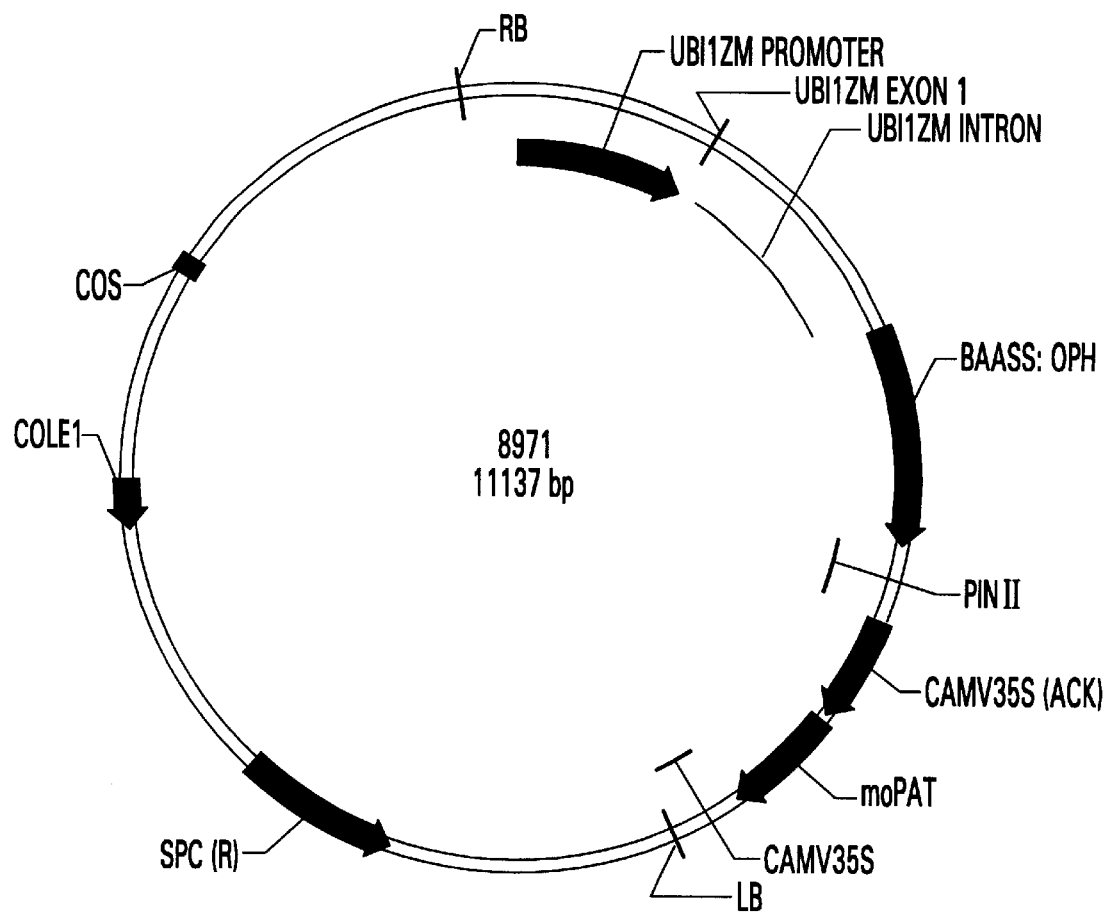
FIG. 19 is p8971 which is a construct containing a ubiquitin promoter, the barley alpha amylase signal sequence, the organophosphate hydrolase gene, with the maize optimized pat selectable marker driven by the 35S promoter.

The gene encoding laccase, obtained from the Stachybotrys fungus was expressed in plants, and recovery of active enzyme improved. The *Stachybotrys chartarum* nucleotide sequence used for this experiment is shown in FIG. 16, and is also described in WO 99/49020.

To prepare the 8947 plasmid, oligomeric sequences encoding the barley amylase signal sequence, BAASS, were added to the 5' end of the Stachybotrys laccase gene and the entire sequence up to the PstI restriction site of the gene was amplified by PCR. The fragment was cloned into a vector backbone resulting in the plasmid K1243. The addition of a HpaI restriction site to the 3' end of the gene was also accomplished with PCR by using a reverse primer containing the restriction site sequence. The resulting plasmid K1222 contains the Stachybotrys laccase sequences back to the AscI restriction site of the gene. The plasmid K1272 containing the entire BAASS:Stachybotrys laccase sequences was produced by ligating the HindIII-PstI fragment from K1243, the PstI-AscI fragment from HM642, containing the original Stachybotrys Laccase gene, and the AscI-HindIII vector portion of K1222 (FIG. 17A). BAASS:Stachybotrys Laccase contained in the BsmBI-HpaI fragment from K1272 was ligated into the NcoI-HpaI vector of KB3 81, containing the Globulin 1 promoter and PinII terminator, resulting in the intermediate plasmid K1369 (FIG. 17A). The entire transcription unit was then cut out of K1369 using HindIII-PmII and ligated into the same sites in 8916 resulting in the final plasmid 8947 which contains the 35S promoter with the PAT selectable marker between the left and right borders of the *Agrobacterium tumefaciens* (FIG. 17B).

Treatment of $T_2$ Seed with Copper

The highest expressing plants from each of five different events was planted in the field. Seed harvested from each of these plants was pooled based on the event from which it was generated. This pooled seed was ground and two separate extracts were prepared using SA buffer. The extracts were split into three separate aliquots and either not treated, treated with 10 mM $CuSO_4$ (final concentration) at 50° C. for one hour, or treated with 30 mM $CuSO_4$ with 0.5 M NaCl at room temperature for one hour. Table 7 shows the results from this experiment.

TABLE 7

Copper Treatment of Stachybotrys laccase Produced in Corn Seed

| | ng active Laccase/mg Seed | |
|---|---|---|
| Event # | No Copper | 10 mM $CuSO_4$, 50° C., 1 h |
| 04 | 0.02 | 0.079 |
| 05 | 0.039 | 0.11 |
| 09 | 0.036 | 0.21 |
| 10 | 0.08 | 0.74 |

Incubation with 10 mM $CuSO_4$ increases the amount of active laccase that is recovered from these corn seed extracts. In the best case shown here, almost 10 fold more activity was recovered after incubation with 10 mM $CuSO_4$ for one hour for event number 10. Sodium chloride inhibits this enzyme significantly, concentrations as low as 100 $\mu$M cause 20% inhibition of the activity. While not wishing to be bound by any theory, it is believed that the sodium chloride improves recovery of active laccase, however, because of its inhibition while in contact with the laccase, it must be removed before the activation process occurs.

The optimal conditions for incubation were investigated. Event #10 seed was extracted as above and treated with 10 mM $CuSO_4$ at room temperature or 50° C. for 5, 10, 15, 30, 60, and 120 minutes before removing the precipitated proteins and analyzing by enzyme assay. The longer incubation times improve the amount of laccase activity recovered (FIG. 18). The higher temperature also improved recovery of laccase activity in these relatively low expressing lines.

EXAMPLE 6

Organophosphate Hydrolase Activation with Metals

Organophosphate Hydrolase (OPH, E.C. 3.1.8.1) is a dimeric metaloenzyme that is capable of breaking down several neurotoxic organophosphorus compounds. (Di Sioudi, B., 1999). Each dimer has a mass of 72,000 Daltons and binds two divalent metal ions per monomer. (Grimsley, J. K, 1997). OPH was first isolated from *Pseudomonas diminuta* MG and Flavobacterum ATCC 27551. (Di Sioudi, B., 1999). OPH requires the presence of divalent transition metal co-factors for catalysis and is capable of using $Zn^{+2}$, $Mn^{+2}$, $Ni^{+2}$, $Cd^{+2}$, and $Co^{+}$. (Omburo, G. A., 1992). OPH has previously been successfully expressed in both prokaryotic and eukaryotic systems. Low availability of metal cofactors was observed by the inventors to be causing the expression of a less active form of the enzyme that can be activated by incubation with the appropriate transition metal.

Optimized OPH Gene

The OPH gene may be obtained from Flavobacterium sp. or *Pseudomonas diminuta*. The amino acid sequence is the same for both organisms. The Genbank accession number for the sequence obtained from Flavobacterium is M29593. The sequence was translated into a protein sequence and then back translated into a DNA sequence using a maize codon usage table with the translate and back-translate programs of the GCG Wisconsin package. Wisconsin Package Ver. 9, Genetics Computer Group (Wisconsin). The sequence was altered with the addition of the barley alpha amylase signal sequence (BAASS). The completed sequence was analyzed for unique restriction sites with the Vector NTI program. Five roughly equidistant sites were chosen for the construction of the OPH optimized gene. Oligos were ordered in 50 bp lengths with 25 bp overhangs. These were annealed and amplified by PCR. Amplified products were trapped in a vector and transformed into competent cells. Colonies were analyzed by restriction analysis and by DNA sequencing. Correct clones were then subcloned together in the vector. After the complete gene sequence was assembled it was cloned into a Maize expression vector under the direction of the ubiquitin promoter and the pinII terminator (p8971 see FIG. 19). The sequence is set forth in FIG. 20.

Plant Transformation

Plasmid 8971 was transferred to Agrobacterium by mating as described above. Agrobacterium was used to transform 800 maize embryos. Embryos were transferred to co-cultivation media for 5 days, followed by counter-selection media for 3 days then the embryos were transferred to selection media and callus was allowed to form. All callus experiments were done with the first transformant to appear (OPAO 1).

Callus Preparation

Callus extracts were prepared by extracting into 20 mM HEPES (N-2-Hydroxyethylpiperazine-N'-2-ethane-sulfonic acid) buffer pH 8.3. Extraction was done using a tissue homogenizer on ice for 2 minutes. Extracts were spun at 10,000× g for 30 minutes. Supernatant was removed and saved and pellets were discarded. Extract was aliquoted and brought up to 10 mM metal ion with 100 mM solutions of each metal salt ($ZnSO_4$, $NiSO_4$, $MnSO_4$, $MgCl_2$, and $CoCl_2$) made up in distilled/deionized (ddi) water. Water (ddi) was added to the No Treatment samples in a volume equal to that of the metal treatments. Samples were incubated in microfuge tubes and temperature was controlled by water-bath (50° and 37° C.) and incubator (25° C.).

Prep of $T_2$ Extracts

Seed derived from OPA event 04 was ground in a coffee grinder. Ground seed was incubated with 3 ml of 20 mM HEPES pH 8.3 per gram of ground seed. Extract was spun for 30 min at 27,000× g. The supernatant was used for all experiments.

Incubation

For those extracts in which salt was added, the extract was diluted using 2M NaCl in water. All extracts were brought to the same volume using water. The no salt treatment was diluted with water alone. Metal was added using IM stock solutions of each metal made up in water. One ml of extract with treatment was transferred to a 1.5 ml microcentrifuge tube and incubated at the appropriate temperature (4° C., ~25° C. (room temperature), 37° C. and 55° C.

OPH Enzyme Assay

OPH activity was analyzed by the hydrolysis of paraoxon. Cleavage of paraoxon yields p-Nitrophenol, which is measured spectrophotometrically at 400 nm. OPH activity was assayed in 1 ml plastic cuvettes by observing the hydrolysis of Paraoxon to p-Nitrophenol at 400 nm. Units of enzyme were determined using the extinction coefficient of p-Nitrophenol (17 $mM^{-1}$ $cm^{-1}$) Each set of data is the average of three assays.

Negative Ion Addition

It was previously shown with bacterial enzyme with its metals removed that the presence of bicarbonate increased the rate of metal center formation. Shim & Raushel, 2000. Corn extracts were prepared as described above and brought to 100 mM bicarbonate with 1M sodium bicarbonate. The control treatment was diluted with an equal volume of water. The samples were then brought to 10 mM $CoCl_2$ with 1M $CoCl_2$. The samples were then placed in a 37° C. water bath. Enzyme assays were performed as described above in 1.5 ml plastic cuvettes with 1 mM Paraoxon as the substrate. A total of 5 µl of each sample was used in each assay and each assay was conducted three times.

Results

Figure 21A:
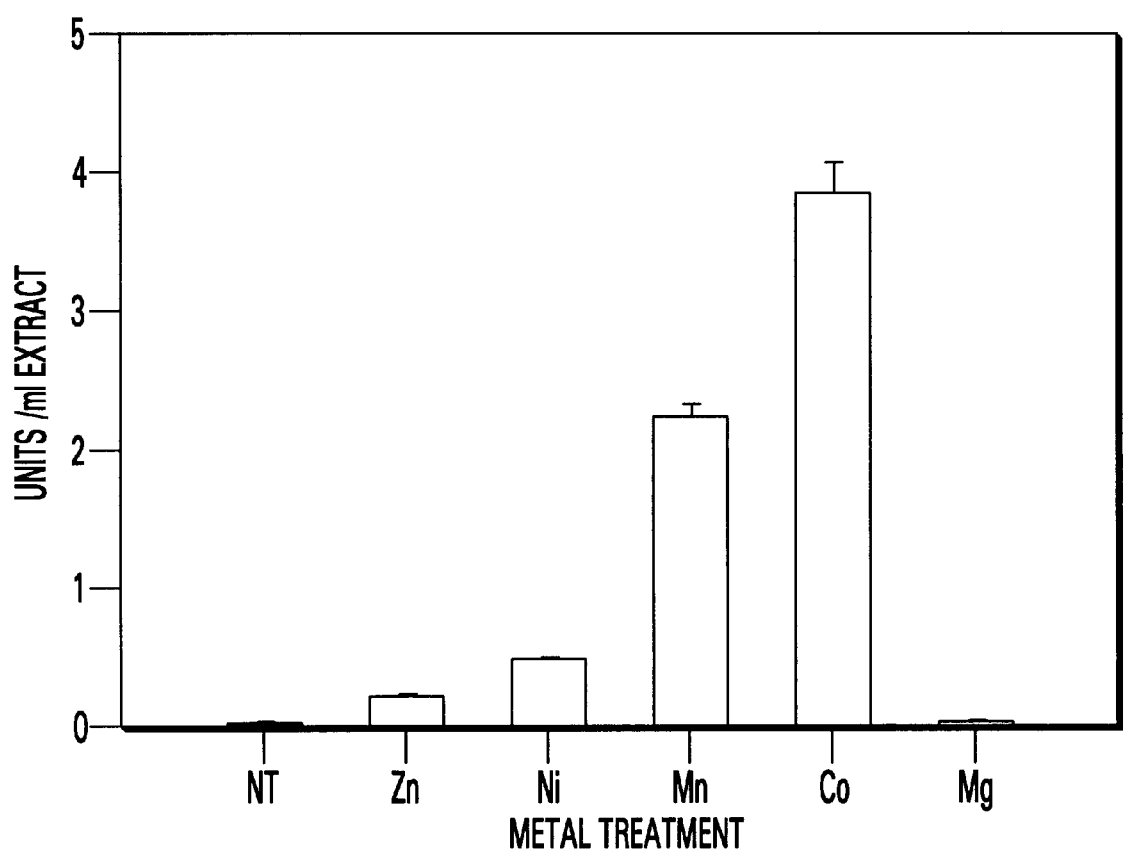
FIG. 21 shows a graph depicting results of increases in OPH Activity in callus and seed. OPH-expressing corn callus extract (panel A) or T2 seed extract (panel B) were incubated with various transition metals at 50° C. for one hour and analyzed for enzyme activity.
Figure 21B:
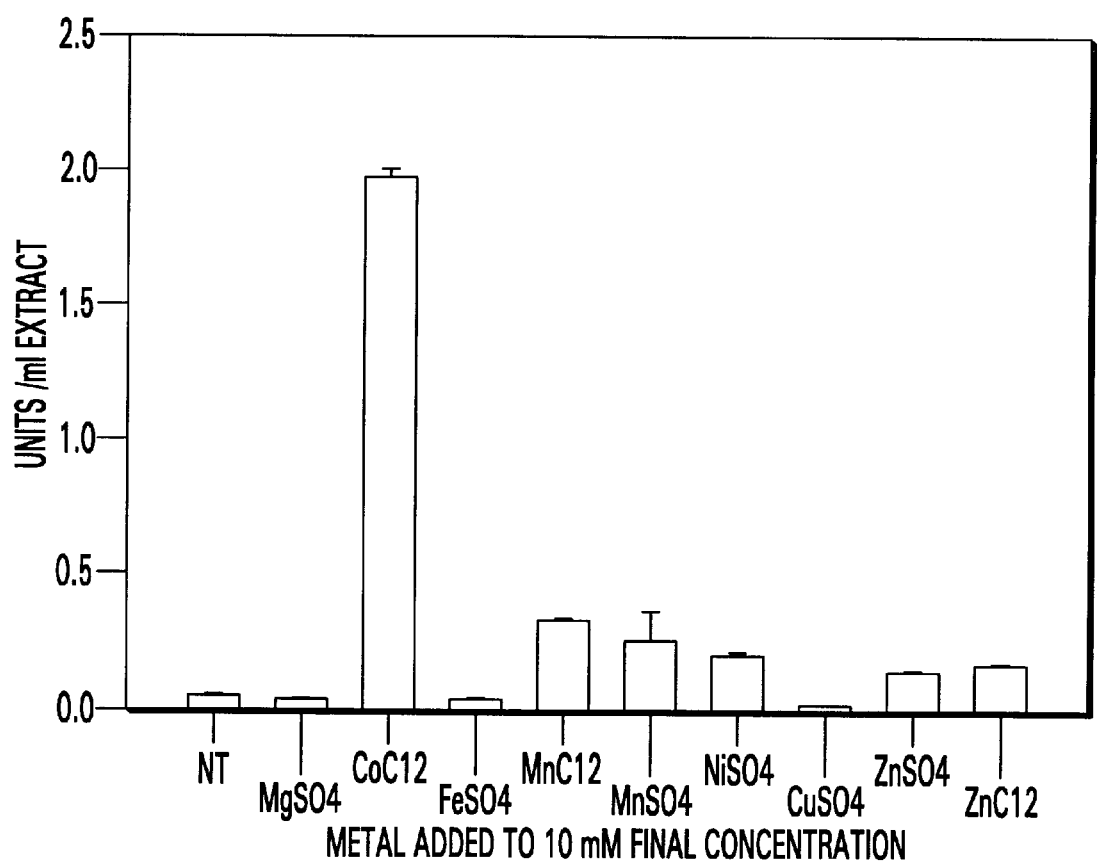
Figure 22:
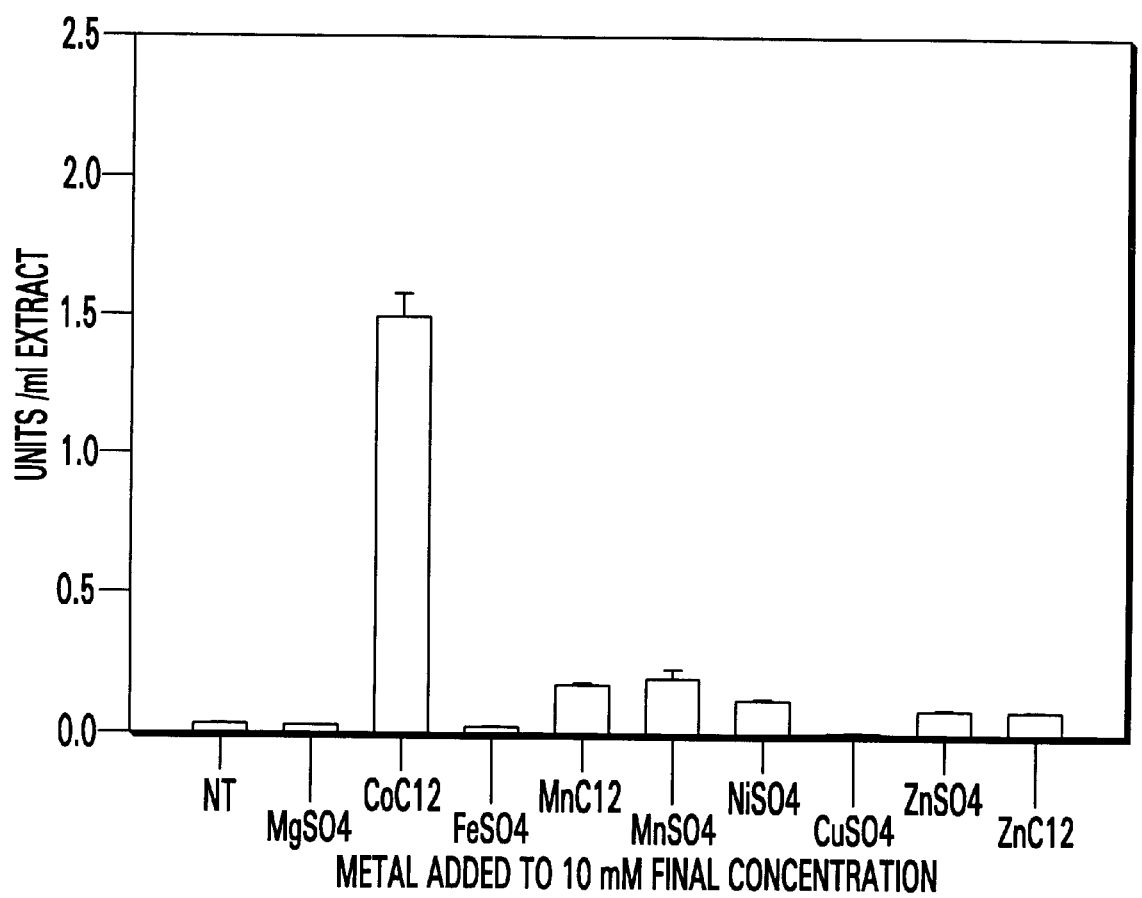
FIG. 22 shows a graph depicting results of increases in OPH Activity With Sodium Chloride. Seed extracts were incubated with 0.5 M NaCl and 10 mM of various transition metal salts, both chloride and sulfate salt types for one hour at 50° C. then analyzed by enzyme assay.

Enzymatic analysis of extracts made from callus tissue showed very low activity. However, after incubation with zinc, cobalt, nickel or manganese at 50° C. for 1, hour an increase of up to 50 fold in OPH activity was recovered when compared to extracted OPH incubated without metal. Incubation with magnesium salt, which is not capable of forming the active enzyme, showed no activity increase. (FIG. 21A). OPH $T_2$ seed showed a similar increase in active enzyme recovered after incubation with 10 mM cobalt, zinc, nickel or manganese, both chloride and sulfate salts (FIG. 21B). In both cases, cobalt gave the best overall recovery of active OPH. Adding 0.1–0.5 M sodium chloride to the incubation buffer does not appear to increase the amount of OPH activity recovered and at 50° C. actually decreases by 25% the amount recovered. (FIG. 22).

Figure 23A:
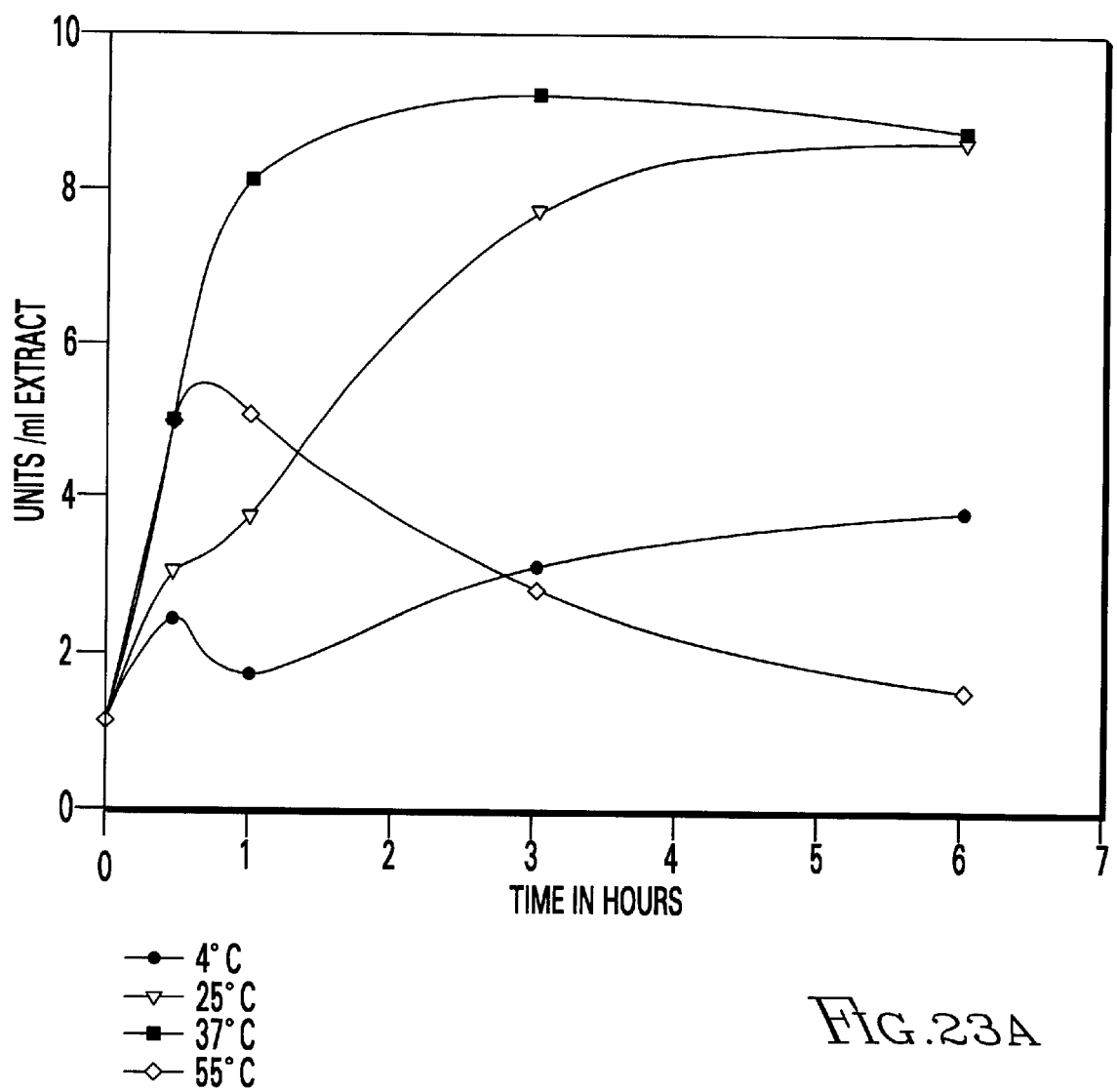
FIG. 23 shows a graph depicting results of increases in OPH Activity over time and at various temperatures.
Figure 23B:
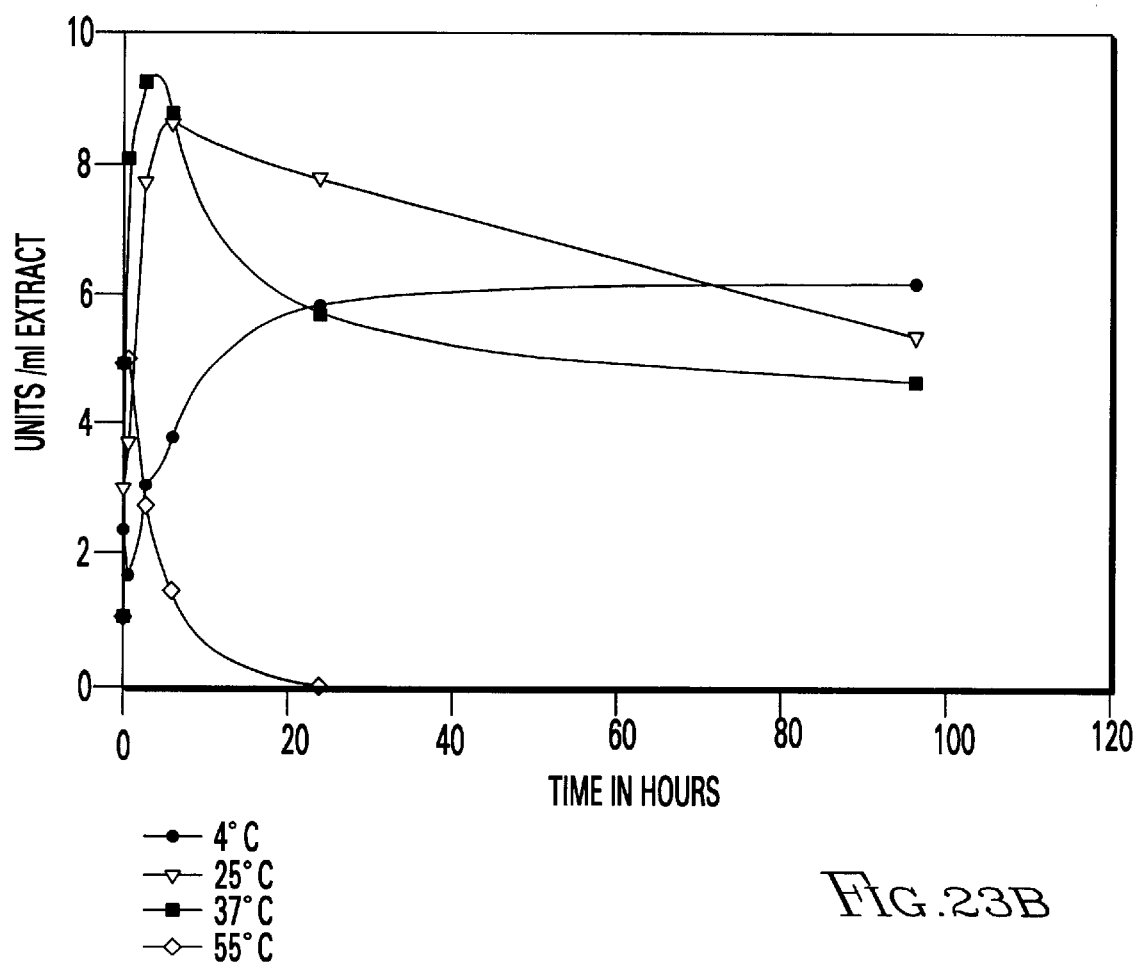

Increasing the temperature of incubation with the metal increases the amount of OPH activity recovered to a point at which the stability of the enzyme is compromised (FIG. 23). OPH enzyme increased in activity at all temperatures tested, most slowly at 4° C., reaching maximal activity after 4 days. Maximal activity was reached at room temperature in approximately 6 hours, with 37° C. being slightly better at three hours although after 4–5 hours, the enzyme is no longer stable. OPH gains maximal activity most rapidly at 50° C., but activity is reduced after only 30 minutes. The time and temperature can be manipulated to achieve the best conditions for any given batch of seed.

Figure 24:
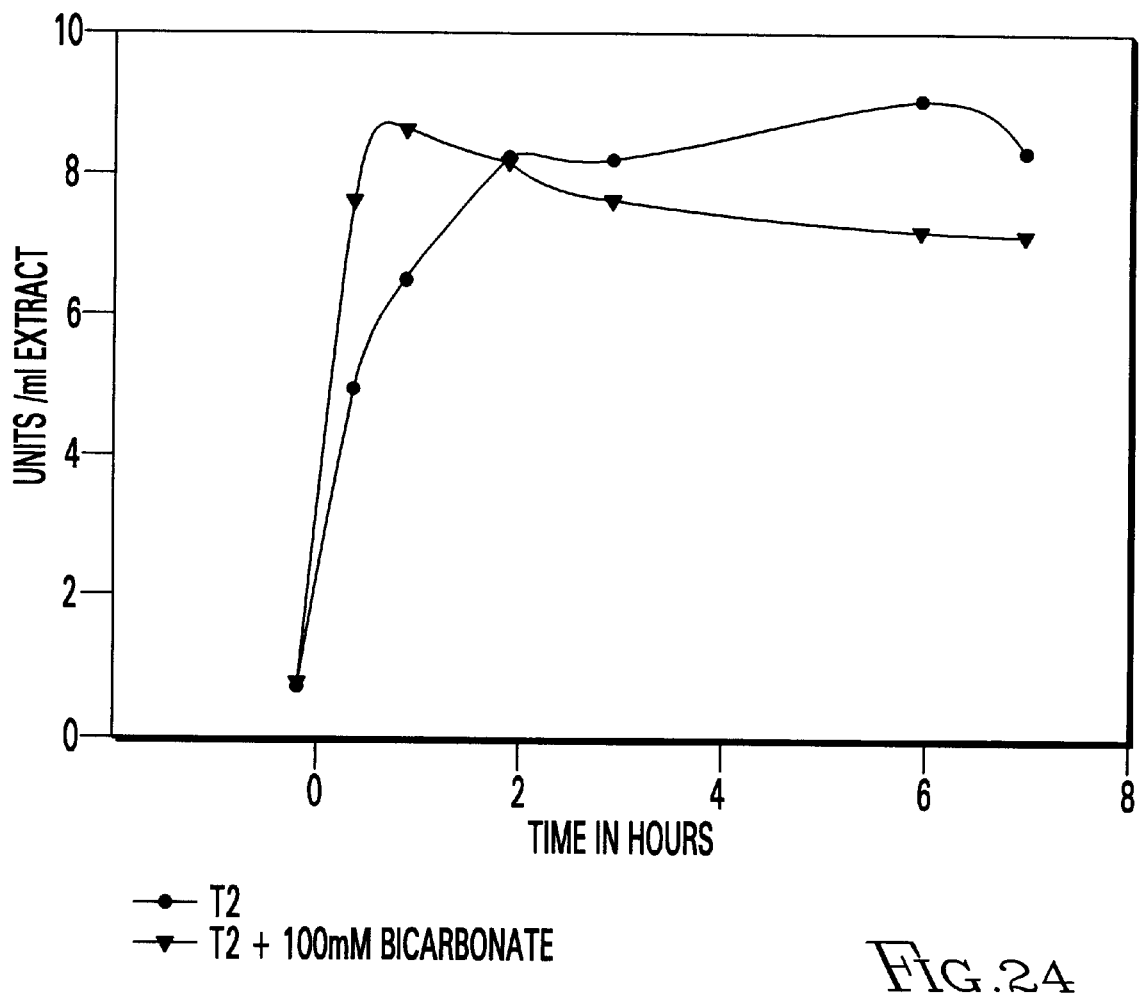
FIG. 24 is a graph showing the results of addition of bicarbonate on activation of OPH in seed.

Impact of addition of bicarbonate on activation is shown in FIG. 24. Recovery of active OPH occurs nearly at the outset of the process, at a higher rate when compared to activation without the negative salt ion (FIG. 24).

OPH expressed in Zea mays shows an increase in activity after incubation with certain transition metals. The pattern of increase in activity follows the pattern already shown for substitution in purified bacterial enzyme. (Omburo, G. A., 1992). One would not expect to have to add this cofactor when producing the enzyme in plants, as opposed to bacteria. Bacteria do not contain such transitional metals as a normal part of their physiology, where a plant has large quantities of the metals, compared to the amount needed to activate the enzyme.

Thus it can be seen that the invention achieves at least all of its objectives.

LITERATURE CITED

Anzai et al., (1989) *Mol. Gen. Gen.* 219:492.

Armstrong, C. L., Green, C. E., Phillips, R. L. (1991). Development and availability of germplasm with high Type II culture formation response. *Maize Genet Coop Newsletter* 65, 92–93.

Belanger, F. C. and Kriz, A. L. at (1991) "Molecular Basis for Allelic Polymorphism of the Maize Globulin-1 gene" *Genetics* 129:863–972.

Bell, D. J., Hoare, M. and Dunnill, P. (1983) The Formation of Protein Precipitates and Their Centrifugal Recovery. *Ad. Biochemical Engineer Vol.* 26

Bradford, M. (1976) A rapid and sensitive method for the quantification of microgram quantities of protein utilizing the principle of protein-dye binding. *Anal Biochem* 72, 248–254.

Bustos et al. (1989) Regulation of β-glucuronidase Expression in Transgenic Tobacco Plants by an A/T-Rich cis-Acting Sequence Found Upstream of a French Bean β-Phaseolin Gene, *The Plant Cell Vol.* 1, 839–853.

Call, H. P. and Mücke, I. (1997) History, overview and applications of mediated lignolytic systems, especially laccase-mediator-systems (Lignozym®-process), *Journal of Biotechnology* 53, 163–202.

Christensen, A. M., Sharrock, R. A., Quail, P. H. (1992) Maize polyubiquitin genes: structure, thermal perturbation of expression and transcript splicing, and promoter activity following transfer to protoplasts by electroporation. *Plant Mol Biol* 18, 675–689.

Christou et al., (1992) *Trends in Biotechnology* 10:239.

Crossway, (1985) *Mol. Gen. Genetics* 202:179–185.

De Boer, H. A., Zhang, Y. S., Collins, C., Reddy, Ardinarayana, C. (1987) Analysis of nucleotide sequences of two ligninase cDNAs from a white-rot filamentous fungus, *Phanerochaete chyrososporium, Gene* 60:93–102.

diSioudi, B., Grimsley, J. K., Lai, K., and Wild, J. R., (1999) Modification of Near Active Site Residues in Organophosphate Hydrolase Reduces Metal Stoichiometry and Alters Substrate Specificity, *Biochemistry, V.* 38 2866–2872

Dudley, J. W. and Lambert, R. J. (1992). Ninety generations of selection for oil and protein in maize. *Maydica* 37, 81–87.

Fraley et al., (1983) *Proc. Natl. Acad. Sci.* 80: 4803.

Fromm et al., (1985) *Proc. Natl. Acad. Sci.* 82: 5824.

Fromm et al., (1990) *Bio/Technology* 8:833.

Glick and Thompson, in Methods in *Plant Molecular Biology and Biotechnology* 269–84 (CRC Press 1993).

Gordon-Kamm et al., (1990) *The Plant Cell* 2:603.

Grimsley, J. K., Scholtz, J. M., Pace, C. N., and Wild, J. R., (1997) Organophosphate Hydrolase is a Remarkably Stable Enzyme that Unfolds through a Homodimeric Intermediate, *Biochemistry, V.* 36 14366–14374.

Gruber et al., "Vectors for Plant Transformation" in *Methods of Plant Molecular Biology and Biotechnology* 89–119 (CRC Press, 1993).

Heney and Orr, (1981) *Anal. Biochem.* 114: 92–96.

Hiei, Yukoh, Ohta, Shozo, Komari, Toshihiko, and Kumashiro, Takashi (1994) Efficient transformation of rice (*Oryza sativa* L.) mediated by Agrobacterium and sequence analysis of the boundaries of the T-DNA. *The Plant Journal* 6(2), 271–282.

Hood, E. E., Helmber, G. L, Fraley, R. T. and Chilton, M. D. (1986). The non-T-DNA portion of pTiBo542 is responsible for the hyper-virulence of *Agrobacterium tumefaciens* A281, *J. Bacteriol.* 168:1291–1301.

Hood, E. E., Witcher, D. R., Maddock, S., Meyer, T., Baszczynski, C., Bailey, M., Flynn, P., Register, J., Marshall, L., Bond, D., Kulisek, E., Kusnadi, A., Evangelista, R., Nikolov, Z., Wooge, C., Mehigh, R. J., Heman, R., Kappel, W. K., Ritland, D., Li, C. P., and Howard, J. A. (1997). Commercial production of avidin from transgenic maize: Characterization of transformant, production, processing, extraction and purification. *Molecular Breeding* 3:291–306.

Hood, E. and Howard, J. Protein Products from Transgenic Plants. *Agro-Food-Industry Hi-Tech,* 3, Vol.10, May/June 1999, pp. 35–36

Hood, E. and Jilka, J. (1999) Plant Based Production of Xenogenic Proteins. *Current Opinion in Biotechnology,* 10:4, pp. 382–386.

Horsch et al., (1984) *Science* 233: 496–498.

Ishida, Yuji, Saito, Hideaki, Ohta, Shozo, Hiei, Yukoh, Komari, Toshihiko, and Kumashiro, Takashi (1996) High efficiency transformation of maize (*Zea mays* L.) mediated by *Agrobacterium tumefaciens*. *Nature Biotechnology* 14, 745–750.

Kay et al., (1987) *Science* 236:1299.

Klein et al., (1992) *Bio/Technology* 10:268.

Klein et al., (1987) *Nature* 327: 70–73.

Lee et al., (1991) *Proc. Nat'l Acad. Sci. USA* 88:6389.

Moloney et al. (1989) "High Efficiency Transformation of *Brassica napus* Using Agrobacterium Vectors" *Plant Cell Reports* 8:238–242.

Miki et al., "Procedures for Introducing Foreign DNA into Plants" in *Methods in Plant Molecular Biology and Biotechnology,* Glick et al. (eds) pp. 67–68 (CRC Press 1993)

Munro, S. and Pelham, H. R. B. (1987) A C-terminal signal prevents secretion of luminal ER proteins. *Cell* 48:899–907.

Omburo, G. A., Kou, J. M., Mullins, L. S., and Raushel, F. M.,(1992) Characterization of the Zinc Binding Site of Bacterial Phophotriesterase, *Journal of Biological Chemistry, V.* 19 13278–13283.

Ong., Ed., Brent, W., Pollack, R. and Smith, M. (1997) Cloning and sequence analysis of two laccases complementary DNAs from the lignolytic *Basidiomycete Trametes versicolor, Gene* 196:113–119.

Paszkowski et al., (1984) *Embo J.* 3: 2717–2722.

Phillips et al., "Cell/Tissue Culture and In Vitro Manipulation" in *Corn and Corn Improvement* 3d Edit. Sprague et al. (eds) pp. 345–387 (American Soc. Of Agronomy 1988).

Pohl T. (1990) Concentration of Proteins and Removal of Solutes. in *Methods in Enzymology v.* 82: *Guide to Protein Purification,* (Murray P. Deutscher ed.) Academic Press, Inc. San Diego. p. 68–82.

Putter, J., and Becker, R. (1981) in *Methods of Enzymatic Analysis* (Bergemeyer, J. U., ed.) Vo.3 p.286, Verlag Chemie, Wienheim.

Rogers, J. C. (1985). Two barley alpha-amylase gene families are regulated differently in aleurone cells. *J. Biol Chem* 260, 3731–3738.

Shim & Raushel (2000) *Biochemistry* 39:7357–7364.

Solomon, Edward I., Sundaram, Uma M., and Machonkin, Timothy E. (1996) Multicopper Oxidases and Oxygenases. *ACS Chem. Rev.* 96(2), 2563–2605.

Stewart, P., Whitwam, R. E., Kersten, P. J., Cullen, D. and Tien, M. (1996) Efficient expression of a *Phanerochaete chrysosporium* manganese perosidase gene in *Aspergillus oryzae, Appl. Env. Mircobiol.* 62:860–864.

Uchimiya et al, (1993) *Bio/Technology* 11:835.

Voss, Regis D. (1993). Nutrient Deficiencies and Toxicities in Crop Plants: Corn. William F. Bennett, Editor. Chapter 2. 11–14. APS Press, Minn. 2:11–14.

Wan et al., (1994) *Plant Physiolog.* 104:37.

Weisinger et al., (1988) *Ann. Rev. Genet.* 22: 421–477.

White, J., Chang, S-YP, Bibb, M. J., and Bibb, J. M. (1992). A cassette containing the bar gene of *Streptomyces hygroscopicus*: a selectable marker for plant transformation. *Nucl Acids Res* 18, 1062.

Yaropolov, A. I., Skorobogat'ko, O. V., Vartanov, S. S., and Varfolomeyev, S. D. (1994). Properties, catalytic mechanism, and applicability. Applied Biochemistry and Biotechnology 49, 257–280.

What is claimed is:

1. A method of improving recovery of active enzyme from a corn plant where the enzyme requires a transitional metal cofactor for activity comprising introducing into the plant nucleotide sequences encoding the enzyme, the enzyme selected from the group consisting of laccase or organophosphate hydrolase, comprising extracting the enzymes from the plant and exposing or treating the enzyme with the metal cofactor.

2. The method of claim 1 wherein the transitional metals ions are one or more of iron, copper, zinc, cobalt, nickel, magnesium, potassium and manganese.

3. A method of improving the levels of active enzyme in a plant where the enzyme requires a transitional metal cofactor for activity, comprising introducing into the corn plant a nucleotide sequence encoding the enzyme, the enzyme selected from the group consisting of laccase or organophosphate hydrolase comprising exposing the plant to a solution containing the metal cofactor during plant development.

4. The method of claim 1 comprising extracting the enzyme from the plant with a solution containing the metal cofactor.

5. The method of claim 1 comprising extracting the enzyme from the plant and contacting the enzyme with the metal cofactor.

6. The method of claim 1 wherein exposure or treatment of the enzyme and metal cofactor to recover maximum active enzyme occurs at a temperature that will not degrade the enzyme.

7. The method of claim 6 further comprising incubating the enzyme and metal cofactor with a negative salt ion.

8. The method of claim 6 wherein the enzyme and metal cofactor are incubated for up to several weeks at a temperature of at least 4° C. and a temperature up to 60° C.

9. The method of claim 6 wherein the enzyme and metal cofactor are incubated for up to 24 hours at a temperature of at least 18° C. and at a temperature up to 55° C.

10. The method of claim 6 wherein the enzyme and metal cofactor are incubated for up to 24 hours at a temperature of at least 20° C. and a temperature up to 27° C.

11. The method of claim 6 wherein the enzyme and metal cofactor are incubated for up to three hours at about 50° C.

12. The method of claim 7 wherein the enzyme and metal cofactor are incubated for up to 60 minutes at least 18° C. and at a temperature up to 37° C.

13. A method of improving isolated of active laccase from a corn plant comprising introducing into the plant a nucleotide sequence encoding laccase and exposing the laccase to copper.

14. The method of claim 13 comprising exposing the plant to the copper by spraying the plant with a solution containing copper during plant development.

15. The method of claim 13 comprising extracting the laccase from the plant and contacting the laccase with copper.

16. The method of claim 13 comprising extracting the laccase from the plant with a solution containing copper.

17. The method of claim 13 comprising exposing the laccase to a salt solution during extraction or after extraction of the laccase from the plant, the salt solution composing at least 0.05 mM copper and comprising no more than 1M copper.

18. The method of claim 17 wherein the salt solution comprises about 1 mM copper and comprises up to 100 mM copper.

19. The method of claim 18 wherein the salt solution comprises at least 10 mM copper and comprises up to 30 mM copper.

20. The method of claim 13 comprising incubating the laccase and copper to recover maximum active enzyme at a temperature that will not degrade the laccase.

21. The method of claim 20 comprising extracting the laccase prior to incubation with the copper.

22. The method of claim 21 comprising incubating the laccase and copper for up to several weeks at a temperature of at least 4° C. and a temperature up to 60° C.

23. The method of claim 22 wherein the laccase and copper are incubated for up to 24 hours at a temperature of at least 18° C. and a temperature up to 55° C.

24. The method of claim 22 wherein the laccase and copper are incubated for up to 24 hours at a temperature of at least 20° C. and a temperature up to 27° C.

25. The method of claim 22 wherein the laccase and copper are incubated for up to three hours at about 50° C.

26. The method of claim 22 wherein the laccase and copper are incubated for about one hour at about 50° C.

27. The method of claim 13 comprising adding a chloride ion salt.

28. The method of claim 27 wherein the chloride ion salt is sodium or potassium chloride.

29. The method of claim 27 wherein the chloride ion salt is cupric chloride.

30. The method of claim 27 wherein the laccase, copper and chloride salt are incubated for up to several hours at a temperature of at least 18° C. and a temperature up to 37° C.

31. The method of claim 28 wherein the incubation is about 60 minutes at a temperature of at least 20 and at a temperature up to 27° C.

32. A method of improving recovery of active organophosphate hydrolase from a plant comprising introducing into the corn plant nucleotide sequences encoding organophosphate hydrolase and exposing the organophosphate hydrolase to a metal cofactor.

33. The method of claim 32 wherein the metal is one or more of the group of zinc, nickel, cobalt or manganese.

34. The method of claim 32 wherein the metal is zinc, nickels cobalt or manganese and the metal and extracted organophosphate hydrolase are incubated for at least 15 minutes up to 24 hours at a temperature of at least 20° and at a temperature up to 27° C.

35. The method of claim 32 comprising adding a bicarbonate ion salt.

36. The method of claim 32 comprising extracting the organophosphate hydrolase from the plant and exposing or treating the organophosphate hydrolase with the metal cofactor during extraction or after extraction.

37. The method of claim 32 comprising spraying the plant with a solution containing the metal cofactor.

* * * * *